United States Patent
Geijsen et al.

(10) Patent No.: US 12,209,252 B2
(45) Date of Patent: Jan. 28, 2025

(54) TRANSDUCTION BUFFER

(71) Applicant: Koninklijke Nederlandse Akademie van Wetenschappen, Utrecht (NL)

(72) Inventors: Niels Geijsen, Utrecht (NL); Peng Shang, Utrecht (NL); Diego D'Astolfo, Utrecht (NL)

(73) Assignee: Koninklijke Nederlandse Akademie van Wetenschappen, Utrecht (NL)

( * ) Notice: Subject to any disclaimer, the term of this patent is extended or adjusted under 35 U.S.C. 154(b) by 389 days.

(21) Appl. No.: 15/775,791

(22) PCT Filed: Nov. 30, 2016

(86) PCT No.: PCT/EP2016/079294
§ 371 (c)(1),
(2) Date: May 11, 2018

(87) PCT Pub. No.: WO2017/093326
PCT Pub. Date: Jun. 8, 2017

(65) Prior Publication Data
US 2018/0327783 A1    Nov. 15, 2018

(30) Foreign Application Priority Data

Nov. 30, 2015 (GB) .................................. 1521101

(51) Int. Cl.
| | |
|---|---|
| *C12N 15/87* | (2006.01) |
| *A61K 9/00* | (2006.01) |
| *A61K 33/14* | (2006.01) |
| *A61K 38/18* | (2006.01) |
| *A61K 38/45* | (2006.01) |
| *A61K 45/06* | (2006.01) |
| *A61K 47/02* | (2006.01) |
| *A61K 47/06* | (2006.01) |
| *A61K 47/10* | (2017.01) |
| *A61K 47/18* | (2017.01) |
| *A61K 47/22* | (2006.01) |
| *A61K 47/26* | (2006.01) |
| *A61K 47/54* | (2017.01) |
| *A61K 48/00* | (2006.01) |
| *C12N 5/0735* | (2010.01) |
| *C12N 9/22* | (2006.01) |
| *C12N 15/11* | (2006.01) |

(52) U.S. Cl.
CPC ............ *C12N 15/87* (2013.01); *A61K 9/0019* (2013.01); *A61K 33/14* (2013.01); *A61K 38/1808* (2013.01); *A61K 38/1825* (2013.01); *A61K 38/45* (2013.01); *A61K 45/06* (2013.01); *A61K 47/02* (2013.01); *A61K 47/06* (2013.01); *A61K 47/10* (2013.01); *A61K 47/183* (2013.01); *A61K 47/22* (2013.01); *A61K 47/26* (2013.01); *A61K 47/54* (2017.08); *A61K 48/0033* (2013.01); *C12N 5/0606* (2013.01); *C12N 9/22* (2013.01); *C12N 15/11* (2013.01); *C12N 2310/20* (2017.05); *C12N 2501/727* (2013.01); *C12N 2800/80* (2013.01)

(58) Field of Classification Search
CPC .............. C12N 5/0606; C12N 2800/80; C12N 2501/727; C12N 2310/20; C12N 15/87; C12N 15/11; C12N 9/22; A61K 47/54; A61K 47/06; A61K 33/14; A61K 9/0019; A61K 45/06; A61K 38/1808; A61K 38/1825; A61K 38/45; A61K 47/22; A61K 48/0033; A61K 47/183; A61K 47/02; A61K 47/10; A61K 47/26
USPC .................................................. 435/325, 455
See application file for complete search history.

(56) References Cited

U.S. PATENT DOCUMENTS

| | | | |
|---|---|---|---|
| 5,627,159 | A | 5/1997 | Shih et al. |
| 6,124,207 | A | 9/2000 | Robinson et al. |
| 6,124,270 | A | 9/2000 | Haensler |
| 6,258,792 | B1 | 7/2001 | Deshmukh et al. |
| 7,906,109 | B2 | 3/2011 | Menart et al. |
| 9,526,784 | B2 | 12/2016 | Liu et al. |
| 10,883,116 | B2 * | 1/2021 | Geijsen ................ A61K 35/545 |
| 2008/0145442 | A1 | 6/2008 | Yarmush et al. |
| 2008/0171023 | A1 | 7/2008 | Salgaller et al. |
| 2008/0193498 | A1 | 8/2008 | Hausheer |
| 2011/0016522 | A1 | 1/2011 | Sheppard |
| 2012/0258046 | A1 * | 10/2012 | Mutzke .................. A61K 47/26 424/9.1 |

(Continued)

FOREIGN PATENT DOCUMENTS

| | | | | |
|---|---|---|---|---|
| EP | 0834572 | A2 * | 4/1998 | ............... C07K 7/06 |
| EP | 1046394 | A2 | 10/2000 | |

(Continued)

OTHER PUBLICATIONS

D'Astolfo et al. (Apr. 23, 2015; Cell, 161, pp. 674-690). (Year: 2015).*

(Continued)

*Primary Examiner* — Janet L Epps-Smith
(74) *Attorney, Agent, or Firm* — Wolf, Greenfield & Sacks, P.C.

(57) ABSTRACT

The invention relates to transduction compounds, buffers and methods for introducing molecules into cells. The invention also relates to methods of treatment, pharmaceutical compositions and other uses of the transduction compounds and buffers. The invention also relates to modified cells obtainable by the transduction compounds, buffers and methods of the invention.

16 Claims, 11 Drawing Sheets

(56) References Cited

U.S. PATENT DOCUMENTS

| | | | |
|---|---|---|---|
| 2013/0206234 | A1 | 8/2013 | Maruyama |
| 2014/0120135 | A1 | 5/2014 | Mombarg |
| 2014/0301990 | A1 | 10/2014 | Gregory et al. |
| 2016/0273001 | A1 | 9/2016 | Geijsen et al. |
| 2018/0282713 | A1* | 10/2018 | Van Der Oost .......... C12N 9/22 |
| 2021/0087585 | A1 | 3/2021 | Geijsen et al. |

FOREIGN PATENT DOCUMENTS

| | | | |
|---|---|---|---|
| EP | 1103259 A1 | 5/2001 | |
| GB | 1506509.7 | 4/2015 | |
| JP | 2000-143486 A | 5/2000 | |
| JP | 2007-516281 A | 6/2007 | |
| JP | 2011-523643 A | 8/2011 | |
| WO | WO 97/06794 A1 | 2/1997 | |
| WO | WO 99/21591 A1 | 5/1999 | |
| WO | WO 01/72280 A2 | 10/2001 | |
| WO | WO 2006/065960 A2 | 6/2006 | |
| WO | WO 2008/093982 A2 | 6/2006 | |
| WO | WO 2008/148223 A1 | 12/2008 | |
| WO | WO 2009/141738 A2 | 11/2009 | |
| WO | WO 2012/050140 A1 | 4/2012 | |
| WO | WO 2012/110010 A1 | 8/2012 | |
| WO | WO 2013/090734 A1 | 6/2013 | |
| WO | WO-2015028969 A2 * | 3/2015 | ............... C12N 9/16 |
| WO | WO 2015/028969 * | 5/2015 | ............. C12N 15/88 |
| WO | WO 2017/093326 A1 | 6/2017 | |

OTHER PUBLICATIONS

Castellot et al. (Proc Natl Acad Sci. USA Jan. 1978;75(1):351-5;See IDS: Aug. 29, 2018)) (Year: 1978).*

Gruber et al. (BioTechniques, Jul. 2004; 37(1): 96-102; See IDS: Aug. 29, 2018) (Year: 2004).*

Lee et al. (Cytometry 14:265-270 (1993) (Year: 1993).*

European Office Action mailed Dec. 12, 2018 for Application No. EP 14784521.8.

Chae et al., Metabolic engineering of *Escherichia coli* for the production of 1,3-diaminopropane, a three carbon diamine. Sci Rep. Aug. 2015;5:13040(1-13).

Dawson et al., Organic osmolytes and embryos: Substrates of the Gly and Beta transport systems protect mouse zygotes against the effects of raised osmolarity. Biol Reproduct. 1997;56:1550-8.

Dega-Szafran et al., $^1$H and $^{13}$C NMR spectra of betaines, $>N^+(CH_2)_n COO^-$, and their hydrogen halides. Additivity rules for carbon-13 chemical shifts. Magn Reson Chem. 2000;38:43-50.

Mock et al., Efficient lentiviral transduction and transgene expression in primary human B cells. Human Gene Therapy Methods. Dec. 2012;23:408-15.

Moore et al., Introduction of soluble protein into the Class I pathway of antigen processing and presentation. Cell. Sep. 1988;54:777-85.

Otto et al., Hyperosmotic stress enhances cytokine production and decreases phagocytosis in vitro. Critical Care. 2008;12:R107, accessed online http://ccforum.com/content/12/4/R107. 8 pages. Epub Aug. 18, 2008.

Sugiura et al., Novel thioredoxin-related transmembrane protein TMX4 has reductase activity. J Biol Chem. Mar. 5, 2010;285(10):7135-42.

[No Author Listed] Pubchem Compound [Online] Database accession No. CID 3085288. Created Aug. 9, 2005, last modified Aug. 1, 2019. 13 pages.

Kouprina et al., Human artificial chromosome-based gene delivery vectors for biomedicine and biotechnology. Expert Opin Drug Deliv. Apr. 2014;11(4):517-35. doi: 10.1517/17425247.2014. 882314. Epub Jan. 30, 2014.

Nam et al., Cas5d protein processes pre-crRNA and assembles into a cascade-like interference complex in subtype I-C/Dvulg CRISPR-Cas system. Structure. Sep. 5, 2012;20(9):1574-84. doi: 10.1016/j.str.2012.06.016. Epub Jul. 26, 2012.

Urnov et al., Genome editing with engineered zinc finger nucleases. Nat Rev Genet. Sep. 2010;11(9):636-46. doi: 10.1038/nrg2842.

Zhou et al., Current methods for loading dendritic cells with tumor antigen for the induction of antitumor immunity. J Immunother. Jul.-Aug. 2002;25(4):289-303.

Zou et al., Roles of Argonaute Proteins in RNA interference. J. Med Mol Biol. 2006;3(1):55-7.

International Search Report and Written Opinion mailed Feb. 7, 2017 for Application No. PCT/EP2016/079294.

International Preliminary Report on Patentability mailed Jun. 14, 2018 for Application No. PCT/EP2016/079294.

International Search Report and Written Opinion mailed May 20, 2015 for Application No. PCT/IB2014/064127.

International Preliminary Report on Patentability mailed Mar. 10, 2016 for Application No. PCT/IB2014/064127.

[No Author Listed] Pubchem Compound [Online] Database accession No. CID 24860518. Jul. 30, 2008. Last accessed Dec. 1, 2015. 6 pages.

Alexander et al., Tethering, recycling and activation of the epithelial sodium-proton exchanger, NHE3. J Exp Biol. Jun. 2009;212(Pt 11):1630-7. doi: 10.1242/jeb.027375.

Al-Quobaili et al., Pancreatic duodenal homeobox factor-1 and diabetes mellitus type 2 (review). Int J Mol Med. Apr. 2008;21(4):399-404.

Beard et al., Efficient method to generate single-copy transgenic mice by site-specific integration in embryonic stem cells. Genesis. Jan. 2006;44(1):23-8.

Berridge, Cell Signalling Pathways. Cell Signalling Biology (2014). 138 pages. doi: 10.1042/csb0001002. Submitted in 7 parts.

Bitler et al., Anti-cancer therapies that utilize cell penetrating peptides. Recent Pat Anticancer Drug Discov. Jun. 2010;5(2):99-108.

Boch, TALEs of genome targeting. Nat Biotechnol. Feb. 2011;29(2):135-6. doi: 10.1038/nbt.1767.

Castellot et al., Animal cells reversibly permeable to small molecules. Proc Natl Acad Sci U.S.A. Jan. 1978;75(1):351-5.

Chadwick et al., MeCP2 in Rett syndrome: transcriptional repressor or chromatin architectural protein? Curr Opin Genet Dev. Apr. 2007;17(2):121-5. Epub Feb. 20, 2007.

Chiang et al., EGF upregulates Na+/H+ exchanger NHE1 by post-translational regulation that is important for cervical cancer cell invasiveness. J Cell Physiol. Mar. 2008;214(3):810-9.

D'Astolfo et al., Efficient intracellular delivery of native proteins. Cell. Apr. 23, 2015;161(3):674-90.

Dawson et al., Organic osmolytes and embryos: substrates of the Gly and beta transport systems protect mouse zygotes against the effects of raised osmolarity. Biol Reprod. Jun. 1997;56(6):1550-8.

Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.

Fawell et al., Tat-mediated delivery of heterologous proteins into cells. Proc Natl Acad Sci U.S.A. Jan. 18, 1994;91(2):664-8.

Frankel et al. Cellular uptake of the tat protein from human immunodeficiency virus. Cell. Dec. 23, 1988;55(6):1189-93.

Garcia et al., Constitutive activation of Stat3 by the Src and JAK tyrosine kinases participates in growth regulation of human breast carcinoma cells. Oncogene. May 3, 2001;20(20):2499-513.

Goldberg et al., Non-detergent sulphobetaines: a new class of molecules that facilitate in vitro protein renaturation. Fold Des. 1995/1996;1(1):21-7.

Green et al., Autonomous functional domains of chemically synthesized human immunodeficiency virus tat trans-activator protein. Cell. Dec. 23, 1988;55(6):1179-88.

Grier et al., The pathophysiology of HOX genes and their role in cancer. J Pathol. Jan. 2005;205(2):154-71.

Gruber et al., RNA interference by osmotic lysis of pinosomes: liposome-independent transfection of siRNAs into mammalian cells. Biotechniques. Jul. 2004;37(1):96-102.

Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014. Author Manuscript, 17 pages.

(56) References Cited

OTHER PUBLICATIONS

Hsieh et al., R11, a novel cell-permeable peptide, as an intravesical delivery vehicle. BJU Int. Nov. 2011;108(10):1666-71. doi: 10.1111/j.1464-410X.2011.10185.x. Epub Mar. 31, 2011.
Ishibashi, et al., Perforated Whole-Cell Patch Clamp Technique: A User's Guide. Chapter 4 in Patch Clamp Techniques: From Beginning to Advanced Protocols. Springer Protocols Handbooks, 2012, pp. 71-83.
Iwakuma et al., Li-Fraumeni syndrome: a p53 family affair. Cell Cycle. Jul. 2005;4(7):865-7. Epub Jul. 4, 2005.
Jenkins et al., Intracellular pH regulation by $Na^+/H^+$ exchanger-1 (NHE1) is required for growth factor-induced mammary branching morphogenesis. Dev Biol. May 1, 2012;365(1):71-81. doi: 10.1016/j.ydbio.2012.02.010. Epub Feb. 17, 2012.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Koivusalo et al., Amiloride inhibits macropinocytosis by lowering submembranous pH and preventing Rac1 and Cdc42 signaling. J Cell Biol. Feb. 2010;188(4):547-63. doi: 10.1083/jcb.200908086. Epub Feb. 15, 2010.
Kültz et al., Hyperosmolality causes growth arrest of murine kidney cells. Induction of GADD45 and GADD153 by osmosensing via stress-activated protein kinase 2. J Biol Chem. May 29, 1998;273(22):13645-51.
Lennon et al., Deletion of 7q31.1 supports involvement of FOXP2 in language impairment: clinical report and review. Am J Med Genet A. Apr. 15, 2007;143A(8):791-8.
Lundberg et al., Is VP22 nuclear homing an artifact? Nat Biotechnol. Aug. 2001;19(8):713.
Luo et al., Hyperosmolarity-induced apoptosis in human corneal epithelial cells is mediated by cytochrome c and MAPK pathways. Cornea. May 2007;26(4):452-60.
Maejima et al., Autophagy sequesters damaged lysosomes to control lysosomal biogenesis and kidney injury. EMBO J. Aug. 28, 2013;32(17):2336-47. doi: 10.1038/emboj.2013.171. Epub Aug. 6, 2013.
Maestro et al., Distinct roles of HNF1beta, HNF1alpha, and HNF4alpha in regulating pancreas development, beta-cell function and growth. Endocr Dev. 2007;12:33-45.
Makarova et al., Prokaryotic homologs of Argonaute proteins are predicted to function as key components of a novel system of defense against mobile genetic elements. Biol Direct. Aug. 25, 2009;4(29):1-15. doi: 10.1186/1745-6150-4-29.
Mali et al., RNA-guided human genome engineering via Cas9. Science. Feb. 15, 2013;339(6121):823-6. doi: 10.1126/science.1232033. Epub Jan. 3, 2013.
Mali et al., Supplementary Materials for RNA-guided human genome engineering via Cas9. Science. Feb. 15, 2013;339(6121):823-6. doi: 10.1126/science.1232033. Epub Jan. 3, 2013.
Mandal et al., Reprogramming human fibroblasts to pluripotency using modified mRNA. Nat Protoc. Mar. 2013;8(3):568-82. doi: 10.1038/nprot.2013.019. Epub Feb. 21, 2013.
Mann et al., Endocytosis and targeting of exogenous HIV-1 Tat protein. EMBO J. Jul. 1991;10(7):1733-9.
Moretti et al., MeCP2 dysfunction in Rett syndrome and related disorders. Curr Opin Genet Dev. Jun. 2006;16(3):276-81. Epub May 2, 2006.
Moscou et al., A simple cipher governs DNA recognition by TAL effectors. Science. Dec. 11, 2009;326(5959):1501. doi: 10.1126/science.1178817.
Nagahara et al., Transduction of full-length TAT fusion proteins into mammalian cells: TAT-p27Kip1 induces cell migration. Nat Med. Dec. 1998;4(12):1449-52.
Okada et al., Introduction of macromolecules into cultured mammalian cells by osmotic lysis of pinocytic vesicles. Cell. May 1982;29(1):33-41.
Paz et al., Galectin-3, a marker for vacuole lysis by invasive pathogens. Cell Microbiol. Apr. 1, 2010;12(4):530-44. doi: 10.1111/j.1462-5822.2009.01415.x. Epub Feb. 9, 2010.

Reinehr et al., Hyperosmolarity triggers CD95 membrane trafficking and sensitizes rat hepatocytes toward CD95L-induced apoptosis. Hepatology. Sep. 2002;36(3):602-14.
Rigor et al., Phosphorylation and activation of the plasma membrane Na+/H+ exchanger (NHE1) during osmotic cell shrinkage. PLoS One. Dec. 2011;6(12):e29210(1-11). doi: 10.1371/journal.pone.0029210. Epub Dec. 28, 2011.
Swarts et al., DNA-guided DNA interference by a prokaryotic Argonaute. Nature. Mar. 13, 2014;507(7491):258-61. doi: 10.1038/nature12971. Epub Feb. 16, 2014.
Symons et al., Vaccinia virus encodes a soluble type I interferon receptor of novel structure and broad species specificity. Cell. May 19, 1995;81(4):551-60.
Takai et al,. DNA transfection of mouse lymphoid cells by the combination of DEAE-dextran-mediated DNA uptake and osmotic shock procedure. Biochim Biophys Acta. Jan. 30, 1990;1048(1):105-9.
Tattersall et al., Modulation of H+ transport mechanisms by interleukin-1 in isolated bovine articular chondrocytes. Cell Physiol Biochem. 2005;16(1-3):43-50.
Tattersall et al., Modulation of Na+-H+ exchange isoforms NHE1 and NHE3 by insulin-like growth factor-1 in isolated bovine articular chondrocytes. J Orthop Res. Nov. 2008;26(11):1428-33. doi: 10.1002/jor.20617. Epub Apr. 10, 2008.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.
Van Der Vliet et al., IPEX as a result of mutations in FOXP3. Clin Dev Immunol. 2007;2007:89017(1-5). doi: 10.1155/2007/89017.
Voncken et al., Genetic modification of the mouse: general technology—pronuclear and blastocyst injection. Chapter 2 in Transgenic Mouse Methods and Protocols, Methods in Molecular Biology. Second Edition, Springer, 2011;693:11-36. doi: 10.1007/978-1-60761-974-1_2.
Vuillard et al., A new additive for protein crystallization. FEBS Lett. Oct. 24, 1994;353(3):294-6.
Vuillard et al., Halophilic protein stabilization by the mild solubilizing agents nondetergent sulfobetaines. Anal Biochem. Sep. 20, 1995;230(2):290-4.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Westra et al., Cascade-mediated binding and bending of negatively supercoiled DNA. RNA Biol. Sep. 2012;9(9):1134-8. doi: 10.4161/rna.21410. Epub Sep. 1, 2012.
Wright et al., Immunization with the recombinant PorB outer membrane protein induces a bactericidal immune response against *Neisseria meningitidis*. Infection and Immunity. Aug. 2002;70(8):4028-34.
Wu et al., Neutron Capture Therapy of Cancer: Nanoparticles and High Molecular Weight Boron Delivery Agents. Ch. 6. Nanotechnology for Cancer Therapy. 2006; 77-103.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
U.S. Appl. No. 14/914,527, filed Feb. 25, 2016, Published, US 2016-0273001.
PCT/EP2016/079294, Feb. 7, 2017, International Search Report and Written Opinion.
PCT/EP2016/079294, Jun. 14, 2018, International Preliminary Report on Patentability.
PCT/IB2014/064127, May 20, 2015, International Search Report and Written Opinion.
PCT/IB2014/064127, Mar. 10, 2016, International Preliminary Report on Patentability.
[No Author Listed], Calbiochem. NDSB-201—CAS15471-17-7. Millipore Sigma. https://www.sigmaaldrich.com/catalog/product/mm/480005?lang=en&region=US. Accessed Apr. 5, 2021. 4 pages.

(56) References Cited

OTHER PUBLICATIONS

[No Author Listed], Pubchem Compound [Online] Database accession No. CID 247. Sep. 16, 2004. Last accessed Apr. 20, 2021. https://pubchem.ncbi.nlm.nih.gov/compound/Betaine. Accessed Apr. 20, 2021.

Schwarze et al., Protein transduction: unrestricted delivery into all cells? Trends Cell Biol. Jul. 2000;10(7):290-5. doi: 10.1016/s0962-8924(00)01771-2.

[No Author Listed], Dulbecco's Modified Eagle's Medium (DMEM), 30-2002 Product Sheet. 5 pages. < https://www.atce.org/products/30-2002> Accessed: Jul. 8, 2022.

* cited by examiner

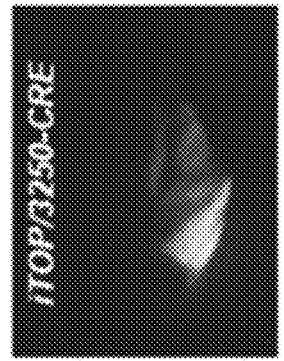
FIG. 2A
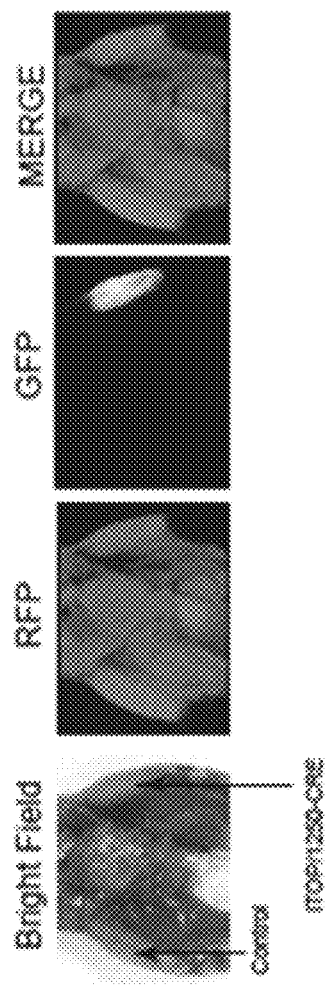
FIG. 2B
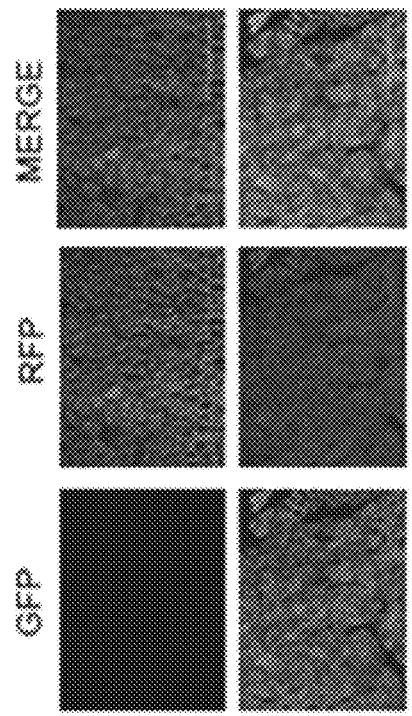
FIG. 2D
FIG. 2C

| Code # | Structure | Transduction (%) | Cell proliferation (%) |
|---|---|---|---|
| 42 | (HOOC-propyl)-N-methylpiperazinium-(butanoic acid), OH⁻ | 255 | 77 |
| 31 | Cl⁻ ⁺H₃N-propyl-C(O)-N(CH₃)₂ | 242 | 81 |
| 45 | Cl⁻, N-methylpiperidinium-propyl-tetrazole | 230 | 111 |
| 43 | Br⁻, N-pyridinium-propyl-C(O)NH₂ | 189 | 108 |
| 34 | OH⁻, N-methylpiperidinium-propyl-C(O)NH-methyl | 185 | 97 |
| 41 | (HOOC-propyl)-N,N-dimethylpiperazinium-(butanoic acid), 2Br⁻ | 163 | 29 |
| 40 | HOOC-propyl-N⁺(CH₃)₂-propyl-COOH, OH⁻ | 160 | 37 |
| 39 | Cl⁻, (CH₃)₃N⁺-propyl-COOH | 144 | 71 |
| 33 | OH⁻, N-methylpiperidinium-CH₂-COOH | 142 | 67 |
| 44 | Br⁻, N-pyridinium-propyl-COOH | 140 | 101 |
| 22 | H₂N-(CH₂)₅-COOH | 135 | 69 |
| 20 | H₂N-(CH₂)₃-COOH | 133 | 95 |
| 03 | N-methylpiperidinium-propyl-SO₃⁻ | 127 | 82 |

FIG. 6A

| Code # | Structure | Transduction (%) | Cell proliferation (%) |
|---|---|---|---|
| 30 | Cl⁻ ⁺H₃N-(CH₂)₃-C(=O)-NH- | 124 | 81 |
| 17 | H₂N-(CH₂)₃-C(=O)-OH | 123 | 90 |
| 15 | OH⁻ piperidinium-(CH₂)₃-C(=O)-NH₂ | 114 | 107 |
| 38 | Cl⁻ (CH₃)₃N⁺-CH₂-CH(OH)-CH₂-C(=O)-OH | 111 | 75 |
| 35 | Br⁻ pyridinium-(CH₂)₃-SO₃H | 110 | 70 |
| 11 | OH⁻ piperidinium-(CH₂)₃-C(=O)-OH | 107 | 97 |
| 10 | pyridinium-(CH₂)₃-C(=O)-O⁻ | 105 | 97 |
| 28 | HO-(CH₂)₃-OH | 104 | 89 |
| 37 | CH₃-C(=O)-NH-(CH₂)₃-C(=O)-OH | 102 | 92 |
| 01 | pyridinium-(CH₂)₃-SO₃⁻ | 100 | 85 |
| 25 | H₂N-(CH₂)₃-NH₂ | 98 | 0 |
| 29 | Cl⁻ ⁺H₃N-(CH₂)₃-C(=O)-NH₂ | 94 | 86 |
| 02 | HO-CH₂-CH₂-N⁺(CH₃)₂-(CH₂)₃-SO₃⁻ | 93 | 84 |

FIG. 6B

| Code # | Structure | Transduction (%) | Cell proliferation (%) |
|---|---|---|---|
| 21 | H₂N-(CH₂)₄-COOH | 93 | 107 |
| 36 | Cl⁻ piperidinium-CH₂CH₂CH₂-COOH | 88 | 75 |
| 26 | H₂N-(CH₂)₃-OH | 84 | 71 |
| 16 | OH⁻ N-methylmorpholinium-(CH₂)₃-COOH | 80 | 75 |
| 06 | ethyl-dimethyl-N⁺-(CH₂)₃-SO₃⁻ | 77 | 85 |
| 04 | benzyl-dimethyl-N⁺-(CH₂)₃-SO₃⁻ | 75 | 75 |
| 19 | H₂N-CH₂CH₂-COOH | 66 | 115 |
| 23 | CH₃(CH₂)₃-COOH | 43 | 88 |
| 24 | H₂N-(CH₂)₃-CH₃ | 39 | 64 |
| 12 | OH⁻ N-methylpiperidinium-(CH₂)₃-COOH | 36 | 92 |
| 14 | OH⁻ N-methylpiperidinium-(CH₂)₃-COOEt | 36 | 80 |
| 13 | OH⁻ N-methylpiperidinium-CH₂-COOH | 32 | 86 |
| 05 | 4-tert-butylpyridinium-(CH₂)₃-SO₃⁻ | 30 | 50 |

FIG. 6C

| Code # | Structure | Transduction (%) | Cell proliferation (%) |
|---|---|---|---|
| 08 | 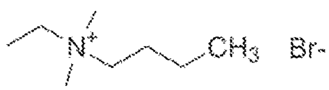 | 30 | 60 |
| 27 | 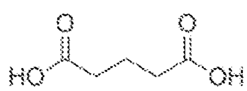 | 22 | 104 |
| 07 | 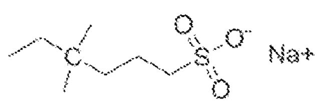 | 16 | 40 |
| 18 | 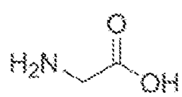 | 9 | 86 |
| 09 | 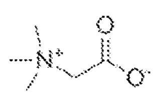 | 5 | 105 |
| 32 | 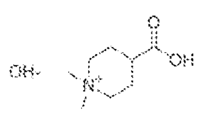 | 0 | 0 |
| 46 | 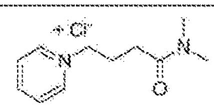 | | |

TRANSDUCTION BUFFER

RELATED APPLICATIONS

This application is a national stage filing under 35 U.S.C. § 371 of international application number PCT/EP2016/079294, filed Nov. 30, 2016, which was published under PCT Article 21(2) in English and claims the benefit of United Kingdom patent application number 1521101.4, filed Nov. 30, 2015, each of which is herein incorporated by reference in its entirety.

TECHNICAL FIELD

This invention relates to transduction buffers and methods for introducing molecules into cells.

BACKGROUND ART

The ability to introduce small- or macromolecules into cells finds important applications in research and medicine. Unfortunately, the cell membrane presents a major obstacle for the introduction of many biologically active molecules.

The ability to introduce proteins into cells has many applications in research and medicine, and more reliable, non-toxic and efficient methods are needed.

Castellot J J Jr et al., (Proc Natl Acad Sci USA. 1978 January; 75(1):351-5) contemplated a method for introducing small molecules into cells using a medium containing 4.2% (w/v) sodium chloride. They demonstrated trypan blue uptake by immortalised hamster BHK cells upon hypertonic treatment. However, the authors did not demonstrate that the trypan blue was released into the cytoplasm or other cellular compartments following uptake. Furthermore, trypan blue is a small molecule and as demonstrated in WO2015/028969, the method described by Castellot and colleagues cannot be applied for the transduction of macromolecules into primary cells and/or stem cell lines.

In 1982, Okada and Rechsteiner demonstrated that hypertonic treatment induced by 0.5M Sucrose and 10% PEG1000 followed by a brief hypotonic treatment induced the intracellular uptake of macromolecules and proteins into immortalized cell lines[1]. However, this technique proved limited to immortalized cell lines, and yields poor protein transduction efficiencies in primary cells (see WO2015/028969).

A few years later, independent discoveries from Green[3] and Frankel[4-5] for the first time demonstrated that the HIV TAT protein can transduce itself across the cell membrane. The peptide sequence mediating this self-transduction was subsequently identified and shown to drive cell transduction when chemically fused to heterologous proteins[6]. Finally, Nagahara and colleagues demonstrated that TAT-peptide mediated protein transduction also worked when the TAT peptide was cloned as an in-frame fusion to the 'cargo' protein of interest[7]. A clear advantage of TAT-peptide mediated protein transduction is that the method appears to work with all cell types, including primary cells, and is generally non-toxic. However, the strong positive charge of the TAT peptide severely hampers the production of native recombinant TAT-fusion proteins in *E. coli*, with much of the recombinant protein ending up in inclusion bodies. In addition, subsequent research demonstrated that some earlier reports on self-transducing proteins were in fact the result of experimental artefact introduced during fixation of the cells[8]. In addition, this technology requires the TAT peptide to be fused to the recombinant protein and therefore limits the type and number of proteins that can be transduced. The TAT peptide itself can disrupt the function or localization of the recombinant protein leading to unexpected or unwanted results. Finally, and perhaps most importantly, the transduction efficiency of TAT-fusion proteins is quite variable and dependent on the nature and physical properties of the protein cargo.

Significant effort has capitalized on the introduction of nucleotides (DNA, RNA, siRNA) and/or therapeutic molecules into cells, and while primary cells still pose a challenge, progress has been made using cationic lipids, nanoparticles or viral vectors as transmembrane carriers. For example, U.S. Pat. No. 6,124,207 describes the use of a cationic amphipathic transfection agent with fusogenic properties to create liposomes (detergent micelles). These liposomes are subsequently mixed with DNA to form liposome-DNA complexes prior to transfection into cells. When performed in vivo, "physiological" saline (aqueous NaCl solution at 9 g/l), also known as "normal" saline and a close approximation to osmolality of NaCl in blood, is added to the transfection formulation. This application explains that transfection efficiency of "naked" DNA is low.

Such "carrier" methods have also been used for targeted gene modification, wherein DNA or mRNA encoding the genetic modification proteins, e.g. TALENs, CRISPR/CAS and other gene editing systems, is transfected into cells. Usually such gene modification is performed by viral transduction. These methods result in significant risk of adverse reactions, including acute immune rejection due to the high dose of injected virus and tumor formation resulting from viral integration position effects. Furthermore, the nucleic acid is expressed within the cell for several days resulting in high expression of enzymes and greater likelihood of off-target effects, e.g. genetic modification of non-target sequences within the cell. Viral transduction also remains inefficient for certain cell types. These difficulties hamper clinical application of the gene editing systems mentioned above.

The development of better technologies for the efficient intracellular delivery of proteins and other macromolecules, particularly in primary cells, is therefore much needed.

It was recently described that a combination of salt-induced hypertonicity, a small molecule compound and osmoprotectants drives the robust and efficient introduction of small- and macromolecules into primary cells, without affecting cell viability (see WO2015/028969). However, the incubation time required can sometimes be too long, for example in situations where prolonged in vitro maintenance of primary cells is not possible, due to the length of a medical procedure, problems with ex vivo cell survival or situations of in vivo transduction where it is difficult to maintain local concentrations of the transduction buffer. In addition, whilst transduction efficiency was found to be directly related to the concentration of extracellularly applied protein, some small- and macromolecules are relatively insoluble in a hydrophilic buffer (e.g. Cas9 protein), and so the amount of such small- and macromolecules that can be transduced can be undesirably low.

Thus there is a need for more efficient methods for transducing proteins, and other molecules, into cells. Transduction of molecules into cells is desirable for a number of therapeutic and scientific purposes, including gene therapy.

The present invention relates to improved methods and transduction buffers which increase the speed, efficiency and quality of transduction. The improved methods are particularly useful for transduction of large proteins including, for example, gene editing tools, and have been shown to work both in vitro and in vivo.

SUMMARY OF THE INVENTION

The invention provides a method for transducing a molecule of interest into a cell, wherein the method comprises contacting said cell with the molecule of interest and a transduction buffer, wherein the transduction buffer comprises:
  (i) a transduction compound,
  (ii) one or more salt, wherein the salt is selected from a sodium, rubidium, lithium, potassium or caesium salt, and is preferably at a total concentration of between about 250 mM and about 2500 mM;
  (iii) a further osmolality-inducing component, which is added at a concentration to make a buffer osmolality of between about 500 mOsmol/kg and about 5000 mOsmol/kg, preferably about 1500 mOsmol/kg and about 5000 mOsmol/kg, more preferably between about 3000 mOsmol/kg and about 5000 mOsmol/kg; and
  (iv) preferably an osmoprotectant.

The invention further provides a method for transducing a molecule of interest into a cell, wherein the method comprises contacting said cell with the molecule of interest and a transduction buffer, wherein the transduction buffer comprises:
  (i) a transduction compound,
  (ii) one or more salt, wherein the salt is selected from a sodium, rubidium, lithium, potassium or caesium salt;
  (iii) one or more protein solubilizing agent, wherein the protein solubilizing agent is (a) a rubidium salt, (b) one or more amino acids and/or (c) a carbohydrate; and
  (iv) preferably an osmoprotectant;
and wherein the total salt concentration is preferably between about 250 mM and about 2500 mM.

The "method for transducing a molecule of interest into a cell" is also referred to herein as the "transduction method" or "method for transduction". These terms are used interchangeably to refer to the same methods.

The invention also provides a transduction buffer comprising:
  (i) a transduction compound,
  (ii) one or more salt, wherein the salt is selected from a sodium, rubidium, lithium, potassium or caesium salt and is preferably at a total concentration of between about 250 mM and about 2500 mM;
  (iii) a further osmolality-inducing compound, which is added at a concentration to make a buffer osmolality of about 500 mOsmol/kg and about 5000 mOsmol/kg, preferably between about 1500 mOsmol/kg and about 5000 mOsmol/kg, preferably between about 3000 mOsmol/kg and about 5000 mOsmol/kg; and
  (iv) preferably an osmoprotectant.

The invention also provides a transduction buffer of the invention for use in therapy.

The invention also provides the use of a transduction buffer of the invention for transducing a molecule of interest into a cell.

The invention also provides a pharmaceutical composition comprising a transduction buffer of the invention.

The invention also provides a method for modifying a nucleic acid, such as a genetic sequence, in a cell, wherein the method comprises contacting said cell with a protein capable of modifying a nucleic acid and a transduction buffer of the invention.

The invention also provides a modified cell obtainable by a method of the invention.

The invention also provides a method for transducing a molecule of interest into a cell, wherein the method comprises contacting said cell with the molecule of interest and a transduction buffer, wherein the transduction buffer comprises
  (iv) GABA and NDSB-201 (e.g. 200 mM GABA and 50 mM NDSB-201) as transduction compounds,
  (ii) sodium chloride and rubidium chloride as salts at a total concentration of between 250 mM and 2500 mM, preferably between 500 mM and 1500 mM,
  (iii) sucrose as a further osmolality inducing component at a concentration such that the final osmolality is at least 500 mOsmol/kg, at least 1000 mOsmol/kg, at least 1500 mOsmol/kg, at least 2000 mOsmol/kg, at least 2500 mOsmol/kg, at least 3000 mOsmol/kg or at least 3250 mOsmol/kg,
  (iv) glycine and glycerol (e.g. 15 mM glycine and 30 mM glycerol) as osmoprotectants, and optionally
  (v) a basal medium.

The invention also provides the use of a transduction buffer of the invention for genetic modification, for example genetic modification of specific target sequences (also referred to herein as "gene editing").

DETAILED DESCRIPTION OF THE INVENTION

Transduction is the internalisation of molecules into a cell, from the external environment. A small number of proteins and peptides have the inherent property of being able to penetrate the cell membrane.

Other proteins can have this transducing property conferred upon them by altering the environmental conditions of the cell or by modifying the protein of interest for transduction.

The invention provides improved methods and buffers for transduction of molecules into cells. In particular the invention provides an improved buffer composition that allows efficient transduction of molecules into cells, without the need to modify the molecule and with minimal loss of cell viability.

The inventors previously showed that a transduction buffer comprising a salt, a transduction compound and, preferably, an osmoprotectant, allows surprisingly efficient uptake of proteins, and other molecules, into cells. It was known that the speed and efficiency of this transduction process depends on the extracellularly applied salt concentration, with higher osmolarities resulting in faster and more efficient uptake. Only sodium-related salts were shown to work in this context. At 1250 mOsm/Kg, efficient protein transduction takes between 45 and 200 minutes. Further elevation of salt-induced hypertonicity can in theory enhance the transduction rate, but the maximum transduction rate is limited by the tolerance of the cells or tissues to the hypertonicity. In addition, protein folding, activity and solubility are very much dependent on salt concentration. Too low or too high salt concentrations can have a detrimental effect on protein stability or solubility.

Surprisingly, the inventors discovered that provided the hypertonicity was generated at least in part by a sodium-related salt, further non-salt osmolality-inducing component could be added to increase the osmolality of the buffer and to increase the efficiency of transduction, without increasing the salt load and damaging cells or negatively affecting protein folding, activity and solubility. Introducing this change to the transduction buffer allowed higher osmolalities, e.g. of 2500 mOsmKg or 3250 mOsmKg, thus accelerating protein transduction and significantly shortening the time needed for uniform transduction of a cell population to e.g. 15 minutes, both in vitro and in vivo (see Example 1). Significantly, this allowed for transduction of larger proteins, and proteins which are more sensitive to salt concentration, and so can be used for transduction of gene editing proteins and for genetic manipulation.

In addition, it was known that the speed and efficiency of this transduction process depends on the extracellularly applied concentration of proteins and other molecules of interest, with higher concentrations resulting in faster and more efficient uptake. However, there are many small- and macromolecules that are relatively insoluble in a hydrophilic buffer. Therefore, the amount of such small- and macromolecules that can be transduced can be undesirably low. The inventors unexpectedly found that whilst some solubilizing agents are compatible with, or even enhance, the transduction process, other solubilizing agents were detrimental to the transduction process.

Surprisingly, the inventors discovered that addition of particular solubilizing agents to a transduction medium permits higher amounts of small- and macromolecules that are relatively insoluble in a hydrophilic buffer to be delivered intracellularly. In addition, some of these compounds also shorten transduction time. Without wishing to be bound by any theory, the reduction in transduction time is thought to occur as a result of the solubilizing agents raising buffer osmolarity.

Examples of gene editing systems that can be introduced into cells using transduction compounds, buffers and methods of the invention generally involve a protein with nuclease activity, for example endonuclease or exonuclease activity. The nuclease activity may be present in the wild type version of the protein or it may be added, e.g. by recombinant methods, to generate a fusion protein. Examples of gene editing systems that can be introduced into cells using transduction compounds, buffers and methods of the invention include proteins that "inherently" target a particular sequence, such as zinc finger nucleases (ZFNs) and TALENS, and also proteins that are "guided" to target sequences using nucleic acids (e.g. small guide RNAs [sgRNAs] or guide DNA [gDNA]), for example as part of the CRISPR-Cas9 system, the Cascade system, TtAgo and other Argonaute systems, and other FOKI-nuclease associated proteins. By "inherently" it is meant that the protein does not require an additional guide molecule to reach its target sequence.

Methods for Transduction

The invention provides a method for transducing a molecule of interest into a cell, wherein the method comprises the steps of contacting said cell with the molecule of interest and contacting said cell with a transduction buffer of the invention.

The molecule of interest and the transduction buffer are contacted with the cell in combination, either simultaneously, sequentially, or separately in any order. In a preferred embodiment, they are administered simultaneously (e.g. from a container containing the combination). Thus, in some embodiments, the transduction buffer comprises the molecule of interest. In some embodiments, the method involves the step of mixing the transduction buffer and the molecule of interest.

In some embodiments, the method comprises the step of obtaining and/or maintaining the cells in culture medium prior to transduction. In some embodiments, the cell is plated in a culture medium, suitable for the particular cell, prior to transduction. In some embodiments, the method further comprises contacting the cell with a culture medium during transduction. In some embodiments, the method includes the step of mixing the transduction buffer with a culture medium.

In some embodiments, the method comprises the steps of obtaining the cells and maintaining the cells in culture medium prior to transduction and contacting the cell with culture medium during transduction. In some embodiments, the method includes the step of mixing the transduction buffer with a culture medium prior to contacting the cell with the transduction buffer. In some embodiments, after transduction, the transduction buffer is aspirated and/or the cells are washed, e.g. once or twice. Typically, a regular culture medium, suitable for the particular cell type, will be added to the cells at this stage. In some embodiments, the method comprises the step of obtaining the cells and/or maintaining the cells in culture medium after transduction.

In some embodiments, the osmolality of the final transduction buffer is adjusted to the desired osmolality by addition of the sodium-related salt and/or by addition of the further osmolality-inducing component. In a preferred embodiment, the final transduction buffer has an osmolality of at least 1250 mOsm/Kg, more than 1250 mOsm/Kg, at least 2500 mOsm/Kg, or at least 3250 mOsm/Kg. In a preferred embodiment, the final transduction buffer that the cell is contacted with, e.g. including the molecule of interest and/or the culture medium, is hypertonic with respect to the cell cytosol.

The method for transduction may be performed in vivo or in vitro.

In some embodiments, the transduction method does not involve a transmembrane carrier, for example selected from a viral plasmid, a nanoparticle, a liposome or other lipid vesicle (including micelles). In some embodiments, the transduction method is non-viral, meaning that it does not rely on a viral transfection system and/or does not involve a viral plasmid, for example as a transmembrane carrier. In some embodiments the transduction method does not involve cationic lipids, for example as transmembrane carriers. In some embodiments, the transduction method does not involve liposomes, for example as transmembrane carriers. In some embodiments, the transduction method does not involve nanoparticles, for example as transmembrane carriers. In some embodiments, the transduction method does not involve outer membrane vesicles (OMVs), for example as transmembrane carriers. In some embodiments the methods does not involve cell penetrating peptides. In a preferred embodiment, the transduction method does not involve exposure of the cell to a hypotonic environment, e.g. a hypotonic buffer.

In some embodiments, the method involves activating or enhancing macropinocytosis and/or enhancing endosomal lysis, thus enhancing uptake of molecules, particularly the molecule of interest, into the cell. In the context of this application, it is to be understood that "endosomes", which are internal invaginations of the cell membrane involved in macropinocytosis, and comprising a complex mixture of lipids, differ from "liposomes" or "micelles", which are synthetic lipid vesicles typically formed from a fewer types of lipid molecule, and from "OMVs", which are bacterial vesicles which may be modified to make them suitable as transmembrane carriers.

In one embodiment (iTOP 2500), the transduction buffer has a final osmolality of about 2500 mOsm/Kg. This transduction buffer preferably comprises: NDSB-201 (e.g. 50 mM) and GABA (e.g. 200 mM) as transduction compounds;

NaCl (e.g. 862 mM) and RbCl (e.g. 125 mM) as salts; sucrose (e.g. 64 mM) as a further osmolality-inducing component; and glycine (e.g. 15 mM) and glycerol (e.g. 30 mM) as osmoprotectants. In addition, the transduction buffer may comprise culture medium components, such as glutamine, non-essential amino acids, N2, B27, growth factors (e.g. FGF2 and EGF), and a basal medium (e.g. a reduced serum medium, e.g. Optimem). Transduction with this buffer is effective for transduction of 10 uM CRE recombinase into hESCs in vitro in about 15 to about 60 minutes.

In another embodiment (iTOP 3250), the transduction buffer has a final osmolality of about 3250 mOsm/Kg. This transduction buffer preferably comprises: NDSB-201 (e.g. 50 mM) and GABA (e.g. 200 mM) as transduction compounds; NaCl (e.g. 1125 mM) and RbCl (e.g. 200 mM) as salts; sucrose (e.g. 100 mM) as a further osmolality-inducing component; and glycine (e.g. 15 mM) and glycerol (e.g. 30 mM) as osmoprotectants. In addition, the transduction buffer may comprise culture medium components, such as glutamine, non-essential amino acids, N2, B27, growth factors (e.g. FGF2 and EGF), and a basal medium (e.g. a reduced serum medium, e.g. Optimem). Transduction with this buffer is effective for transduction of 10 uM CRE recombinase into hESCs in vitro in about 15 minutes or less.

In some embodiments, the day before (e.g. about 12 to 24 hours before) transduction, cells are plated in the appropriate culture media without antibiotics. The following day (the day of transduction), the transduction buffer is prepared with the molecule of interest. The transduction buffer and the molecule of interest are mixed with cell culture medium to obtain a transduction buffer with the desired osmolality.

This mixture of media/transduction buffer/molecule of interest is added to the cell. The cell is incubated with the molecule of interest in the transduction buffer for at least the necessary time period for transduction to occur, after which time, the transduction media is removed and exchanged for regular culture media.

In another embodiment, transduction is performed at multiple stages with different osmolalities. For example the osmolality may be adjusted part way through transduction, e.g. by addition of salt or a further osmolality-inducing component to increase the osmolality, or by dilution to reduce the osmolality.

For the avoidance of any doubt, it is to be understood that these methods and protocols are compatible and combinable with the transduction compounds, salts, further osmolality-inducing components, osmoprotectants, and other additional components, and concentrations thereof, of the transduction buffer described in detail below. These protocols and methods can be used to transduce various molecules of interest, including combinations of molecules of interest into cells, as described in detail below.

Transduction Compound for Transduction

Inclusion of a transduction compound in the transduction buffer is required for efficient transduction. Thus the transduction buffer of the invention comprises at least one transduction compound as described herein.

The inventors have found that various compounds, when used in the context of the transduction buffer of the invention, allow efficient transduction of a molecule of interest into a cell. Thus a "transduction compound" as used herein, refers to any compound that enhances transduction of a molecule of interest into a cell, when used in the context of a transduction buffer of the invention. The beta-lactamase assay, as described in the examples, can be used to determine whether or not a compound is a transduction compound. If a further assay is required to test the efficacy of a transduction compound, particularly to demonstrate the involvement of the macropinocytosis mechanism, the Gal3-GFP assay described in WO2015/028969 can be used.

The first transduction compound that the inventors discovered was a non-detergent sulfobetaine (NDSB; e.g. NDSB-201). The inventors tested derivatives of this compound (such as non-detergent carbobetaines [NDCBs] and found a number of other related compounds that are also transduction compounds. Although there are a variety of compound structures that work, there are a number of common features that can be drawn from the various different compounds, as described in more detail below.

The inventors have found that transduction compounds generally comprise at least one hydrophilic functional group. In some embodiments the transduction compound has only one hydrophilic functional group; examples of such compounds include pentanoic acid (example compound #23 in FIGS. 6A-6D) and n-butylamine (example compound #24 in FIGS. 6A-6D). In some embodiments, the transduction compound has more than one hydrophilic functional group, e.g. 2, 3, 4, 5 or more.

While the transduction compound allows substantial freedom at its termini, it appears that a hydrophilic group is preferred at either end of the carbon chain. Therefore, in preferred embodiments, the transduction compound is a compound having at least two hydrophilic groups, each separated by a short hydrophobic group, such as C1-6 alkylene. In some embodiments, the transduction compound is a compound having at least two hydrophilic groups, each separated by a C4-6 alkylene. An alkylene with 7 or more carbons in the chain is likely to be toxic to the cells. The hydrophilic groups may be the same or different.

In some embodiments, a combination of transduction compounds described herein is used. For example, (i) a compound having at least two hydrophilic groups, each separated by a C4-6 alkylene, and (ii) a compound having at least two hydrophilic groups, each separated by a C3 alkylene. The hydrophilic groups may be the same or different.

In some embodiments, the transduction compound is a betaine. As used herein, the term "betaine" refers to any neutral chemical compound with a cationic functional group, which bears no hydrogen atom, and with an anionic functional group. Non-limiting examples of cationic functional groups include quaternary ammonium cations. Non-limiting examples of anionic functional groups include carboxylate, sulfonate and phosphate anions.

In some embodiments, the transduction compound is not a detergent. In some embodiments, the transduction compound is a non-detergent betaine. The term "non-detergent betaine" (NDB) refers to a betaine which does not form micelles in solution. Thus transduction compounds that are not detergents do not form liposomes or micelles in solution.

For example, in some embodiments, the transduction compound is a non-detergent sulfobetaine (NDSB). NDSBs are betaines having a sulfonate group separated from a quaternary nitrogen group, by a short hydrophobic group, such as C1-6 alkylene.

In some embodiments, the transduction buffer comprises a combination of: (i) a betaine having a sulfonate group separated from a quaternary nitrogen group by a C4-6 alkylene and (ii) a compound having at least two hydrophilic groups, each separated by a C3 alkylene (e.g. a betaine having a sulfonate group separated from a quaternary nitrogen group by a C3 alkylene).

In some embodiments, the transduction compound is a small molecule compound. In some embodiments, the transduction compound has fewer than 50 carbon atoms, fewer than 30 carbon atoms, fewer than 25 carbon atoms or fewer than 20 carbon atoms. In some embodiments, the transduction compound has a mass of less than 1000 g/mol, less than 500 g/mol, less than 400 g/mol, less than 360 g/mol, less than 300 g/mol, less than 200 g/mol.

Without wishing to be bound by theory, the inventors hypothesise that these compounds can fold towards each other creating a hydrophobic and a hydrophilic side of the molecule allowing the compound to function particularly well as a transduction compound, for example as shown below.

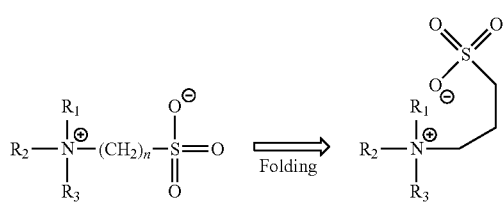

In some embodiments, the quaternary nitrogen atom is part of an aliphatic or aromatic ring structure. In some embodiments, the transduction compound is an NDSB selected from dimethylethyl-(3-sulphopropyl)-ammonium salt (NDSB-195, Vuillard et al (1994) FEBS Letters, 353, 294-296; Goldberg et al (1995/1996) Folding & Design, 1, 21-27), 3-(1-pyridino)-1-propanesulfonate (NDSB-201), dimethylbenzylammonium propanesulfonate (NDSB-256), dimethyl-t-butyl-(3-sulphopropyl) ammonium salt (NDSB-222t), 3-(1-methylpiperidine)-1-propanesulfonate (NDSB221), dimethyl-(2-hydroxyethyl)-(sulphopropyl)-ammonium salt (NDSB-211; Vuillard et al (1995) Anal Biochem, 230, 290-294). In a preferred embodiment, the transduction compound is NDSB-201.

It has also been found that non-detergent carboxybetaines (NDCBs) function as transduction compounds. Thus in some embodiments, the transduction compound is an NDCB. NDCBs are betaines having a carboxylate group separated from a quaternary nitrogen group, by a short hydrophobic group, such as C1-6 alkylene. NDCBs may be able to fold up in solution as described above for NDSBs, enhancing their transduction promoting capability. The inventors found that substitution of the sulfonate group of an NDSB for a carboxylate group to form an NDCB does not negatively affect the transduction efficiency. As shown in the examples below, many NDCBs work with a greater efficiency and with reduced impact on cell viability and/or cell proliferation than NDSBs.

In some embodiments, the transduction buffer comprises a combination of: (i) a betaine having a carboxylate group separated from a quaternary nitrogen group by a C4-6 alkylene and (ii) a compound having at least two hydrophilic groups, each separated by a C3 alkylene (e.g. a betaine having a carboxylate group separated from a quaternary nitrogen group by a C3 alkylene).

Non-betaine compounds which are zwitterionic in solution across a broad range of pHs also function as transduction compounds. For example, some amino acids, such as GABA (gamma-aminobutyric acid), which are zwitterionic in solution, also function as transduction compounds. Zwitterionic compounds often comprise at least one acidic and at least one basic functional group, which may become ionised in solution. Acidic groups include carboxylic acid, sulfonic acid and phosphonic acid functional groups. Basic groups include amino groups. Thus, in some embodiments, the transduction compound is a zwitterion, for example, a non-detergent zwitterion, preferably comprising at least one acidic functional group and at least one basic functional group. In certain preferred embodiments the acidic functional group is separated from the at least one basic group, by a short hydrophobic group, such as C1-6 alkylene.

In some embodiments, the transduction buffer comprises a combination of (i) a zwitterion comprising at least one acidic functional group and at least one basic functional group, wherein the acidic functional group is separated from the at least one basic group by a C4-6 alkylene and (ii) a compound having at least two hydrophilic groups, each separated by a C3 alkylene (e.g. a zwitterion comprising at least one acidic functional group and at least one basic functional group, wherein the acidic functional group is separated from the at least one basic group by a C3 alkylene).

It has also been surprisingly found that non-zwitterionic compounds operate as transduction compounds. Instead of having a negatively charged functional group (such as carboxylate or sulfonate as described above), compounds comprising bioisosteric groups such as an amide or tetrazole also function as transduction compounds. Thus, in some embodiments the transduction compound comprises an amide or tetrazole functional group. In certain preferred embodiments the transducing promoting agent (the transduction compound) comprises an amide or tetrazole functional group separated from another hydrophilic group, preferably amino or ammonium, by a short hydrophobic group, such as C1-6 alkylene.

Thus in some embodiments, the transduction compound is a zwitterion or a non-zwitterionic compound with a group that is bioisosteric to a negatively charged functional group. It is thought that owing to the bioisosteric group, in combination with a positively charged functional group, these non-zwitterionic compounds have some "zwitterionic properties", e.g. to allow the folding mechanism described above. Groups that can be bioisosteric to a negatively charged functional group include, but are not limited to, amide and tetrazole functional groups (for example, see compounds #43, #15, #29, #34, #30, #31 and #45).

In accordance with the above, the transduction compound may be a compound of formula I

wherein:
X is selected from NR$^1$R$^2$, NR$^1$R$^2$R$^3$+, OH and COOR$^4$;
Y is selected from SO$_3$H, SO$_3^-$, COO$^-$, CONH$_2$, COOR$^{12}$, CONR$^5$R$^6$, tetrazole, OH, NR$^{10}$R$^{11}$, and H;
n is 1, 2, 3, 4, 5 or 6;
R$^1$, R$^2$ and R$^3$, are each independently selected from H, C1-6 alkyl, C5-10 aryl, C6-15 aralkyl, COR$^9$; C1-6 alkyl, C5-10 aryl and C6-15 aralkyl may optionally be substituted with R$^Y$, OH or COOH;
or R$^1$ and R$^2$ may come together with the nitrogen to which they are attached to form heterocyclyl;
or when X is NR$^1$R$^2$R$^3$+, R$^3$ may be absent and R$^1$ and R$^2$ may come together with the nitrogen to which they are attached to form heteroaryl;

$R^4$, $R^5$, $R^6$, $R^9$, $R^{10}$, $R^{11}$, $R^{12}$ are independently selected from H and C1-6 alkyl;

$R^7$ and $R^8$ are independently selected from H, C1-6 alkyl and OH; or $R^7$ may come together with $R^1$ to form heterocyclyl;

heterocyclyl is a monocyclic ring which is saturated or partially unsaturated, containing where possible 1 or 2 ring members independently selected from N, $NR^{13}$, $NR^{13}R^{14}+$ and O, and 2 to 5 carbon atoms; heterocyclyl may optionally be substituted with C1-C6 alkyl, C1-C6 carboxylic acid or C1-C6 alkyl substituted with $R^Y$;

heteroaryl is a 5 or 6 membered aromatic ring containing, where possible, 1, 2 or 3 ring members independently selected from N, $NR^{13}$, $NR^{13}R^{14}+$ and O; heteroaryl may optionally be substituted with C1-C6 alkyl, C1-C6 carboxylic acid or C1-C6 alkyl substituted with $R^Y$;

$R^{13}$ and $R^{14}$ are independently selected from H, C1-6 alkyl, C1-C6 carboxylic acid and C1-C6 alkyl substituted with $R^Y$;

alkyl is a linear or branched saturated hydrocarbon;

$R^Y$ is selected from $SO_3H$, $SO_3^-$, $COO^-$, $CONH_2$, $COOR^{12}$, $CONR^5R^6$, tetrazole, OH and $NR^{10}R^{11}$;

C1-6 carboxylic acid means —COOH or a C1-5 alkyl chain substituted with COOH and tautomers, solvates, zwitterions and salts thereof.

Transduction compounds may in some embodiments comprise a quaternary or basic nitrogen group. Thus in some embodiments the transduction compound is a compound of formula I wherein X is $NR^1R^2R^3+$ or $NR^1R^2$.

In some embodiments $R^1$, $R^2$ and $R^3$, are each independently selected from H and C1-6 alkyl which may optionally be substituted with $R^Y$, OH or COOH; or $R^1$ and $R^2$ may come together with the nitrogen to which they are attached to form heterocyclyl, preferably piperidine, piperazine or morpholine, which may be optionally substituted; or $R^3$ may be absent and $R^1$ and $R^2$ may come together with the nitrogen to which they are attached to form heteroaryl, preferably pyridyl, which may be optionally substituted.

In some embodiments the transduction compound is a compound of formula I wherein Y is selected from $SO_3H$, $SO_3^-$, $COO^-$, $COOR^{12}$, $CONR^5R^6$ and tetrazole, preferably selected from $SO_3H$, $SO_3^-$, $COO^-$, $COOR^{12}$ and $CONR^5R^6$, and more preferably selected from $COO^-$, COOH and $CONR^5R^6$.

In some embodiments $R^Y$ is selected from $SO_3H$, $SO_3^-$, $COO^-$, $COOR^{12}$, $CONR^5R^6$ and tetrazole, preferably $R^Y$ is selected from $SO_3H$, $SO_3^-$, $COO^-$, $COOR^{12}$ and $CONR^5R^6$, and more preferably $R^Y$ is selected from $COO^-$, COOH and $CONR^5R^6$.

It has been found that when the carbon chain separating X and Y is three carbon atoms long transduction is promoted more efficiently. Thus in some embodiments, the transduction compound is a compound of formula I wherein n is 3. In other embodiments, n is 1, 2, 3, 4, 5 or more. In some embodiments, n is 6 or less, 5 or less, 4 or less, 3 or less or 2 or less. In some embodiments, n is between 4 and 6.

In some embodiments, the transduction buffer comprises a combination of more than one transduction compounds. For example, (i) a compound of formula I wherein n is 3 and (ii) a compound of formula I wherein n is 4, 5 or 6.

In some preferred embodiments, the transduction compound is a compound belonging to a subset of formula I, according to formula II

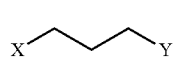

(II)

wherein

X is selected from $NR^1R^2$ and $NR^1R^2R^3+$;

Y is selected from $SO_3H$, $SO_3^-$, $COO^-$, $CONH_2$, $COOR^{12}$ and $CONR^5R^6$;

$R^1$, $R^2$ and $R^3$, are each independently selected from H and C1-6 alkyl which may optionally be substituted with OH or COOH; or $R^1$ and $R^2$ may come together with the nitrogen to which they are attached to form heterocyclyl, preferably piperidine, piperazine or morpholine, which may be optionally substituted; or when X is $NR^1R^2R^3+$, $R^3$ may be absent and $R^1$ and $R^2$ may come together with the nitrogen to which they are attached to form heteroaryl, preferably pyridyl, which may be optionally substituted;

and all other groups are as defined in formula I above.

In some embodiments, the transduction compound contains a quaternary nitrogen group. Thus, in some embodiments the transduction compound is a compound of formula I or II wherein X is $NR^1R^2R^3+$. In some embodiments the transduction compound is a compound of formula I or II wherein X is $NH_3+$.

In some embodiments, the quaternary nitrogen may be part of an aliphatic or aromatic ring structure. Thus, in some embodiments the transduction compound is a compound of formula I or II wherein X is

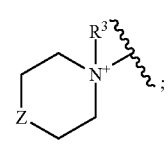

(a)

Z is selected from $C(R^{15})_2$, $NR^{13}$, $NR^{13}R^{14}+$ and O;

each $R^{15}$ is independently selected from H, C1-6 alkyl, C1-C6 carboxylic acid and C1-C6 alkyl substituted with $R^Y$;

$R^3$ is selected from H, C1-6 alkyl, C5-10 aryl, C6-15 aralkyl, $COR^9$; C1-6 alkyl, C5-10 aryl and C6-15 aralkyl may optionally be substituted with $R^Y$, OH or COOH. Preferably $R_3$ is —$CH_3$;

$R^{13}$ and $R^{14}$ are independently selected from H, C1-6 alkyl, C1-C6 carboxylic acid and C1-C6 alkyl substituted with $R^Y$.

In some embodiments the transduction compound is a compound of formula I or II wherein X is (a), Z is $NR^{13}$ or $NR^{13}R^{14}+$ and $R^{13}$ is —$CH_2CH_2CH_2R^Y$. Alternatively, in other embodiments the transduction compound is a compound of formula I or II wherein X is (a), Z is $CH_2$ and $R^3$ is —$CH_3$.

In other embodiments the transduction compound is a compound of formula I or II wherein X is

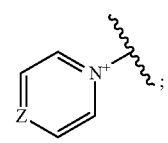

(b)

Z is selected from $CR^5$ and $NR^{13}+$;

$R^{15}$ is selected from H, C1-6 alkyl and C1-C6 carboxylic acid and C1-C6 alkyl substituted with $R^Y$;

$R^{13}$ is selected from H, C1-6 alkyl, C1-C6 carboxylic acid and C1-C6 alkyl substituted with $R^Y$.

In some embodiments the transduction compound is a compound of formula I or II wherein X is (b), Z is $NR^{13}$ and $R^{13}$ is —$CH_2CH_2CH_2R^Y$. Alternatively, in other embodiments the transduction compound is a compound of formula I or II wherein X is (b) and Z is CH.

In some embodiments the transduction compound is a compound selected from the compounds in FIGS. 6A-6D. "Compound #" as used herein, refers to the compounds in FIGS. 6A-6D using the compounds numbers (#) in the left-hand column.

In some embodiments the transduction compound is selected from compound #10, #11, #16, #42, #34, #41, #40, #39, #33, #15, #11, #29, #46 and #36.

In some embodiments the transduction compound is not compound #32. In some embodiments, the transduction compound is not any of the compounds selected from compounds #27, #07, #18, #09 and #32. These compounds all display less than 30% transduction compared to control compound #1. Where statements refer to "the compounds in FIGS. 6A-6D" it is understood that in some embodiments, this refers to all compounds in FIGS. 6A-6D except for compound #32, or all compounds in FIGS. 6A-6D except for compounds #27, #07, #18, #09 and #32.

In some embodiments the transduction compound is selected from putrescine, 5-aminovaleric acid, 6-aminocaproic acid and 6-aminohexanoic acid.

In some embodiments, the transduction compound is a small molecule compound and is not a detergent. In some embodiments, the transduction compound is a small molecule compound and is not a detergent and is a zwitterion or a non-zwitterionic compound with a group that is bioisoteric to a negatively charged functional group. In some embodiments, the transduction compound is a small molecule compound and is not a detergent and is a zwitterion. In some embodiments the transduction compound is a small molecule compound and is a zwitterion or a non-zwitterionic compound with a group that is bioisoteric to a negatively charged functional group.

In some embodiments, the concentration of the transduction compound is between about 0.1 mM and about 500 mM, between about 1 mM and about 400 mM, between about 1 mM and about 300 mM, between about 1 mM and about 200 mM, between about 1 mM and about 100 mM, between about 2 mM and about 200 mM, between about 2 mM and 100 mM, between about 2 mM and about 80 mM, between about 3 mM and about 75 mM, between about 4 mM and about 70 mM, between about 5 mM and about 60 mM, between about 10 mM and about 50 mM, between about 25 mM and 40 mM, or about 30 mM. In some embodiments, the concentration of the transduction compound is about 25 mM, for example the concentration of the transduction compound is, in some embodiments, between about 10 and about 25 mM, or about 25 mM. In some embodiments, the concentration of the transduction compound is at least 1 mM, at least 2 mM, at least 3 mM, at least 4 mM, at least 5 mM, at least 10 mM, at least 20 mM, at least 30 mM, at least 40 mM, at least 50 mM, at least 60 mM, at least 70 mM or at least 80 mM, at least 90 mM, at least 100 mM, at least 150 mM, at least 200 mM, at least 300 mM, at least 400 mM or 500 mM.

In some embodiments, the concentration of the transduction compound is about 100 mM to about 500 mM, about 200 mM to about 400 mM, 200 mM to about 300 mM, or about 250 mM. These higher concentration ranges are particularly useful, for example, when transducing proteins of low solubility, such as Cas9. It is to be understood that the optimum concentration of transduction compound will also depend on the compound and its efficiency, but can be determined readily by the person skilled in the art, for example using the experiments and assays described in the examples.

In some embodiments, the transduction compound is compound #15 (BU-2026-05). This compound is advantageous because it results in high efficiency of transduction, whilst maintaining good cellular viability, even when used at high concentrations (see FIGS. 6A-6D).

In some embodiments, the transduction compound is compound #10. In some embodiments, the transduction compound is compound #11. In some embodiments, the transduction compound is compound #16. In some embodiments, the transduction compound is compound #42. In some embodiments, the transduction compound is compound #34. In some embodiments, the transduction compound is compound #41. In some embodiments, the transduction compound is compound #11. In some embodiments, the transduction compound is compound #40. In some embodiments, the transduction compound is compound #39. In some embodiments, the transduction compound is compound #33. In some embodiments, the transduction compound is compound #29. In some embodiments, the transduction compound is compound #15. In some embodiments, the transduction compound is compound #36. In some embodiments, the transduction compound is compound #46. In some embodiments, the transduction compound is compound #20. Compound #20 has been shown to result in particularly good cell survival rates compared to other transduction compounds.

In some embodiments, the transduction compound is any compound that has 20% or more, 30% or more, 40% or more, 50% or more, 60% or more, 70% or more, 80% or more, 90% or more, 100% or more, 110% or more, 120% or more, 150% or more, 200% or more, 300% or more, 400% or more, 500% or more, 600% or more, 700% or more, 800% or more, 1000% or more transduction efficiency compared to reference compound #1 in FIGS. 6A-6D (NDSB-201), as determined by the methods described in Example 1.

Similarly, in some embodiments, the transduction method (as a whole) has 20% or more, 30% or more, 40% or more, 50% or more, 60% or more, 70% or more, 80% or more, 90% or more, 100% or more, 110% or more, 120% or more, 150% or more, 200% or more, 300% or more, 400% or more, 500% or more, 600% or more, 700% or more, 800% or more, 1000% or more transduction efficiency, using the method comprising compound #1 as shown in FIGS. 6A-6D as a control (i.e. as 100% transduction efficiency).

Non-limiting examples of transduction compounds with more than 100% transduction efficiency compared to reference compound #1 in FIGS. 6A-6D include reference compounds #30, #17, #15, #38, #35, #11, #10, #28 and #37. These compounds are particularly effective transduction compounds. Thus in some embodiments that transduction compound is selected from compounds #30, #17, #15, #38, #35, #11, #10, #28 and #37.

Other preferred transduction compounds include #42, #1, #45, #43, #44, #15, #10, #11, #28, #37 and #46. Thus in some embodiments the transduction compound is selected from compounds #42, #1, #45, #43, #44, #15, #10, #11, #28, #37 and #46. These are compounds that have or are expected to have transduction efficiency of 50% or more relative to control compound #1 and/or 75% or more viability relative to control compound #1.

In some situations it may be advantageous to use a transduction compound in the buffer that causes a reduction in cell proliferation or viability. For example, in the case of vaccine development, some toxicity may be an advantage. Antigens transduced into cells are displayed to the immune system. If the displaying cells are ill or dying, the immune response can be enhanced. Transduction compounds suitable for such purposes include compounds #40, #41, #25, #35 and #38. Thus in some embodiments, the transduction compound is selected from compounds #40, #41, #25, #35 and #38.

In other embodiments, the transduction compound is selected from the compounds #10, #11, #16, #42, #34, #41, #40, #39, #33, #15, #11, #29, #36 and #46.

The transduction compounds described herein can exist as monomers, dimers or multimers. For example, compound #42 is active as a dimer. Thus in some embodiments, the transduction compound is used in its monomeric, dimeric or multimeric form. In some embodiments, the transduction compound is the dimeric form of compound #42.

One of the compounds found to be a transduction compound was a gamma-aminobutyric acid (GABA, compound #20) which an important neurotransmitter in the brain. GABA acts by stimulating the activation of GABA-receptors, of which three classes have been identified: GABA-A, GABA-B and GABA-C. GABA receptors are stimulated by a remarkably wide range of chemical structures ranging from simple structures like ethanol and GABA itself, to seemingly unrelated benzodiazepines, muscimol, baclofen. As the chemical structure of effective protein transduction compounds also displays a degree of freedom, the inventors hypothesise that GABA signalling might play an active role in the transduction effect. Indeed, the inventors found that addition of GABA agonists to the transduction buffer comprising a salt and a transduction compound (such as NDSB-201), resulted in increased transduction of 0-lactamase into mouse embryonic fibroblast (MEFs). Thus in some embodiments the transduction compound is a GABA agonist.

Methods for identifying GABA agonists are known in the art. For example, GABA agonists suitable for use in the transduction buffer can be identified by an assay which measures activation of GABA receptors by a given compound by measuring changes in membrane potential using patch clamp technology on brain slices (Patch Clamp Techniques, Springer Protocols Handbooks, 2012, pp 71-83). There are also commercial assays available for identifying GABA-B agonists (e.g. "Ready-to-assay" by Millipore). Suitable GABA agonists for use in the transduction buffers described herein can be identified using such assays.

Thus, in some embodiments, the transduction buffer further comprises a GABA agonist. A GABA agonist includes any compound that activates the GABA signalling pathway, for example any compound that binds to and/or activates a GABA receptor (e.g. GABA-A, GABA-B and/or GABA-C receptors), for example, as identified using the patch clamp assay or the Millipore assay referenced above. Examples of GABA agonists include, but are not limited to, SKF-97541, acamprosate, barbiturates, benzodiazepines, ethanol, methaqualone, muscimol, nonbenzodiazepines (zaleplon, zolpidem, zopiclone), picamilon, progabide, tiagabine, baclofen, 1,4-Butanediol, GBL (γ-Butyrolactone), GHB (γ-Hydroxybutyric acid), GHV (γ-Hydroxyvaleric acid), GVL (γ-Valerolactone), lesogaberan, phenibut, (Z)-4-Amino-2-butenoic acid, (+)-cis-2-aminomethylcyclopropane carboxylic acid, N4-Chloroacetylcytosine arabinoside, GABOB (γ-Amino-beta-hydroxybutyric acid), and progabide.

In some embodiments, the transduction buffer comprises muscimol and/or SKF-97541.

In some embodiments, the GABA agonist is included in the transduction buffer at concentrations in micro- or nano-molar ranges. For example, in some embodiments, the GABA agonist has a concentration of about 0.1 µM and about 100 µM, between about 1 µM and about 90 µM, between about, 2 µM and about 80 µM, between about 3 µM and about 75 µM, between about 4 µM and about 70 PM, between about 5 µM and about 60 µM, between about 10 µM and about 50 µM, between about 25 µM and 40 µM, or about 30 µM. In some embodiments, the GABA agonist has a concentration of about 10 PM, of about 25 µM or of about 50 µM. In other embodiments, the GABA agonist has a concentration of between about 0.1 nM and about 100 nM, between about 1 nM and about 90 nM, between about 2 nM and about 80 nM, between about 3 nM and about 75 nM, between about 4 nM and about 70 nM, between about 5 nM and about 60 nM, between about 10 nM and about 50 nM, between about 25 nM and 40 nM, or about 30 nM. In some embodiments, the GABA agonist has a concentration of about 10 nM, of about 25 nM or of about 50 nM.

Other neurotransmitters may similarly enhance transduction. Therefore, in some embodiments, the transduction buffer additionally comprises a neurotransmitter.

In some embodiments, the transduction buffer comprises one transduction compound. In some embodiments, the transduction buffer comprises two or more (e.g. 2, 3, 4, 5, 6 or more) transduction compounds, for example two or more of the recited transduction compounds, in any possible combination. In some embodiments, the transduction buffer comprises compound #1 and compound #18. In some embodiments, the transduction buffer comprises compound #1 and compound #34. In some embodiments, the transduction buffer comprises compound #1 and compound #20.

In a preferred embodiment, the transduction buffer comprises an NDSB and a GABA agonist as transduction compounds. In another embodiment, the transduction buffer comprises an NDCB and a GABA agonist as transduction compounds. For example, in one embodiment, the transduction buffer comprises NDSB-201 and GABA as transduction compounds.

Salt for Use in the Transduction Buffer

The inventors found that presence of a "sodium-related" salt, i.e. a salt containing a metal in group 1 of the periodic table, was necessary for the invention. Therefore, the salt for use in the transduction buffer is a sodium, lithium, potassium, caesium, or a rubidium salt. In a preferred embodiment, the salt is a sodium and/or rubidium salt.

In some embodiments, the salt is a chloride, gluconate, carbonate, sulphonate, sulphate, sulphide, bromide, iodide or fluoride, preferably the chloride or gluconate. Non-limiting examples of salts suitable for use in the transduction buffer include sodium chloride, sodium gluconate, lithium chloride, lithium gluconate, potassium chloride, potassium gluconate, caesium chloride, caesium gluconate, rubidium chloride and rubidium gluconate.

In some embodiments, one salt is included in the transduction buffer. In some embodiments, more than one salt is included in the transduction buffer, for example, two, three, four or five salts.

In a preferred embodiment, the transduction buffer comprises sodium chloride and rubidium chloride as salts.

The concentration of salt used depends on the desired osmolality of the transduction buffer—higher salt concentration leads to higher osmolality. However, the viability of the cells and the molecule of interest for transduction should also be taken into consideration: in some circumstances, high salt concentrations may harm cells or cause proteins to denature or to precipitate out of solution. Therefore, the concentration of salt should be neither too high nor too low.

In some embodiments the total salt concentration in the transduction buffer is more than 250 mM, more than 300 mM, more than 400 mM, more than 500 mM, more than 600 mM, more than 700 mM, more than 800 mM, more than 900 mM, more than 1000 mM, more than 1100 mM, more than 1200 mM, more than 1300 mM, more than 1400 mM, more than 1500 mM, more than 1600 mM, more than 1700 mM, more than 1800 mM, more than 1900 mM, more than 2000 mM, more than 2100 mM, more than 2200 mM, more than 2300 mM, more than 2400 mM or more than 2500 mM.

In some embodiments the total salt concentration in the transduction buffer is 2500 mM, less than 2500 mM, less than 2400 mM, less than 2300 mM, less than 2200 mM, less than 2100 mM, less than 2000 mM, less than 1900 mM, less than 1800 mM, less than 1700 mM, less than 1600 mM, less than 1500 mM, less than 1400 mM, less than 1300 mM, less than 1200 mM or less than 1000 mM.

In some embodiments the total salt concentration in the transduction buffer is between 250 mM and 2500 mM, between 300 mM and 2250 mM, between 400 mM and 2000 mM, between 500 mM and 1900 mM, between 600 mM and 1800 mM, between 700 mM and 1700 mM, between 800 mM and 1600 mM, between 1000 mM and 1500 mM.

In some embodiments the salt is NaCl and the concentration is between 250 mM and 2500 mM, between 300 mM and 2250 mM, between 400 mM and 2000 mM, between 500 mM and 1900 mM, between 600 mM and 1800 mM, between 700 mM and 1700 mM, between 800 mM and 1600 mM, between 1000 mM and 1500 mM.

In some embodiments the salt is RbCl and the concentration is between 250 mM and 2500 mM, between 300 mM and 2250 mM, between 400 mM and 2000 mM, between 500 mM and 1900 mM, between 600 mM and 1800 mM, between 700 mM and 1700 mM, between 800 mM and 1600 mM, between 1000 mM and 1500 mM.

In some embodiments, the transduction buffer comprises NaCl at a concentration of between 600 mM and 2000 mM, between 600 mM and 1800 mM, between 700 mM and 1700 mM, or between 800 mM and 1600 mM and RbCl at a concentration of between 50 mM and 1000 mM, between 100 mM and 500 mM, or between 100 mM and 200 mM.

In some embodiments, the transduction buffer comprises NaCl at a concentration of approximately 850 mM and RbCl at a concentration of approximately 125 mM. In some embodiments, the transduction buffer comprises NaCl at a concentration of approximately 1125 mM and RbCl at a concentration of approximately 200 mM.

In general the salt cannot freely diffuse across a cell membrane and thus can increase tonicity across a cell membrane when brought into contact with a cell, i.e. to generate hypertonicity. Tonicity is explained in more detail below.

Activator and/or Enhancer of a Sodium/Hydrogen Transporter

Protein transduction is strongly inhibited by specific inhibitors of Na+/H+ exchange such as EIPA or DMA, specific inhibitors of a family of sodium-hydrogen antiporter (Nhe) proteins, suggesting that the transduction process involves active cellular uptake of exogenously applied compounds through macropinocytosis. Without wishing to be bound by theory, the inventors hypothesise that activation of such Nhe transporters leads to activation of the macropinocytosis pathway, which is the first step in the transduction process. Thus, in some embodiments, the salt is any salt able to bind to and/or activate a sodium/hydrogen (Na+/H+) transporter, such as an Nhe transporter, for example an Nhe1 transporter. Nhe1 is a ubiquitous membrane-bound enzyme involved in volume- and pH-regulation of vertebrate cells.

In some embodiments, the transduction buffer further comprises an activator and/or enhancer of a sodium/hydrogen transporter, such as the Nhe1 transporter, as a replacement for, or in addition to the salt. For example, several growth factors have been shown to induce macropinocytosis by activating Nhe1 and enhancing Na+/H+ exchange. Accordingly, in some embodiments, the activator or enhancer of an sodium/hydrogen transporter is a cytokine or growth factor. In some embodiments, the activator or enhancer of a sodium/hydrogen transporter is epidermal growth factor (EGF), Fibroblast growth factor (FGF), Platelet-derived growth factor (PDGF), Insulin, Insulin-like growth factor (IGF). Small molecule agonists of cytokine or growth factor signalling can also induce Nhe1 activity. Other examples of activators of NHE1 include, but are not limited to, small molecule agonists of cytokine or growth factor signalling, angiotensin II, glucocorticoids and hormones (Alexander R T, J Exp Biol 212, 1630-1637, 2009). In some embodiments, the transduction buffer comprises more than one activator and/or enhancer of a sodium/hydrogentransporter, for example one, two, three, four or five. Any combination of the above activators and/or enhancers is contemplated, with or without a salt, as described above.

Other activators and/or enhancers of macropinocytosis or endosomal lysis can also be useful in the context of the invention. For example, a short dTAT-HA2 fusion peptide, previously shown to enhance macropinosome escape of proteins, was demonstrated by the present inventors to enhance protein transduction, and was particularly effective in mouse embryonic stem cells (mESCs). Therefore, in some embodiments, the transduction buffer additionally comprises an activator and/or enhancer of macropinocytosis or a facilitator of macropinosomal escape. In some embodiments, the transduction buffer additionally comprises dTAT-HA2 fusion peptide. In some embodiments, the transduction buffer additionally comprises a lysogenic peptide. For example, in some embodiments, the transduction buffer additionally comprises an activator and/or enhancer of endosomal lysis.

There is also provided the use of a lysogenic peptide for enhancing transduction of a molecule of interest into a cell, preferably as part of a transduction buffer described herein.

Inhibition of Transduction

The inventors have shown that transduction by the methods described herein occurs via macropinocytosis and requires actin remodelling. Thus, specific inhibitors of these processes can prevent transduction.

In some embodiments, the transduction methods can be inhibited by Cytochalasin D or Latrunculin A, or other specific inhibitors of actin polymerization and vesicle transport. Similarly, the transduction methods can be inhibited by specific inhibitors of Na+/H+ exchange by Nhe transporters, such as EIPA or DMA.

Further Osmolality-Inducing Components

The inventors previously tested whether increasing osmolality using non-salt compounds would also trigger protein transduction but found that sucrose, lactulose, sorbitol and mannitol all failed to induce protein transduction at 700 mOsm/Kg. It was concluded that the transduction method is specifically dependent on hypertonicity induced by sodium or sodium-related salts, perhaps because of the involvement of Nhe transporters, as described above (see also WO2015/028969).

Surprisingly, the inventors have now discovered that provided there are sodium-related salts present in the transduction buffer, osmolality can be further increased using a further non-salt osmolality inducing component and, moreover, that this increase can enhance efficiency of transduction. For example, when sucrose was added to the transduction buffer in addition to one or more sodium-related salt, it was found that osmolality could be increased to 3250 mOsmol/Kg or more without damaging the molecule for interest for transduction and without significant loss of cell viability. For example, the transduced CRE protein in FIGS. 2A-2D is still active. Moreover, transduction at this higher osmolality was found to be much faster (e.g. 6× faster). For more details, see Example 1. This was surprising in view of the previously held belief that only sodium-related salts could be used to raise osmolality and induce transduction.

The further osmolality-inducing component can be any component which increases osmolality without increasing salt load. In general the further osmolality-inducing component is any solute that cannot freely diffuse across a cell membrane and thus can increase tonicity across a cell membrane when brought into contact with a cell, i.e. to generate hypertonicity. Tonicity is explained in more detail below. In some embodiments, the further osmolality-inducing component is one or more of the osmoprotectants listed in Table A.

Exemplary further osmolality-inducing components suitable for use in the transduction buffer and methods of the invention include simple sugars (such as monosaccharides or disaccharides), sugar alcohols, and polyethylene glycols (e.g. PEG). Examples of suitable monosaccharides include glucose, fructose, galactose and ribose. Examples of suitable disaccharides include sucrose, lactose, maltose, trehalose, cellobiose and lactulose. Sugar alcohols are a known class of polyols that are well known for their use as sugar replacements in food. In one embodiment, sugar alcohols have the general formula $HOCH_2(CHOH)nCH_2OH$. Specific examples of suitable sugar alcohols include sorbitol, mannitol, xylitol and erythritol.

Thus, in some embodiments, the further osmolality-inducing component is selected from sucrose, lactose, maltose, trehalose, cellobiose, lactulose, glucose, fructose, galactose, ribose, sorbitol, mannitol, xylitol, myo-inositol and erythritol. In a preferred embodiment, the further osmolality-inducing component is selected from sucrose, sorbitol and mannitol. In a most preferred embodiment, the further osmolality-inducing component is sucrose.

In some embodiments, the further osmolality-inducing component is selected from one or more amino acids. In some embodiments, the one or more amino acids are selected from the following: amino acid, for example, selected from glycine, histidine, alanine, isoleucine, arginine, asparagine, leucine, aspartic acid, lysine, glutamic acid, cysteine, methionine, phenylalanine, glutamine, threonine, tryptophan, proline, valine, ornithine, selenocysteine, serine, tyrosine and proline.

In some embodiments, the further osmolality-inducing component is also a protein solubuilizing agent. For example, in some embodiments, one or more amino acids (e.g. a combination of L-Glu and L-Arg) may be present in a transduction buffer of the invention as further osmolality-inducing components and as protein solubilizing agents.

The concentration of osmolality-inducing components used depends on the desired osmolality of the transduction buffer—higher concentration leads to higher osmolality and greater transduction efficiency. The further osmolality-inducing component may be at a concentration of at least 10 mM, at least 20 mM, at least 30 mM, at least 40 mM, at least 50 mM, at least 60 mM, at least 70 mM, at least 80 mM, at least 90 mM, at least 100 mM or more than 100 mM. The further osmolality-inducing component may be at a concentration of less than 500 mM, less than 400 mM, less than 300 mM, less than 200 mM or less than 100 mM. In some embodiments, the further osmolality-inducing component is at a concentration of between 10 mM and 500 mM, between 20 mM and 400 mM, between 30 mM and 300 mM, between 50 mM and 200 mM, or approximately 100 mM.

In a preferred embodiment, the further osmolality-inducing component is sucrose. Preferred concentrations of sucrose are between 50 mM and 150 mM, for example, but not limited to, 63 mM (e.g. to achieve an osmolality of 2500 mOsm/kg) or 100 mM (e.g. to achieve an osmolality of 3250 mOsm/kg).

Osmolality Ranges

The salt and further osmolality-inducing component, as defined above, are added to the transduction buffer in appropriate quantities to achieve the desired osmolality. The osmolality of the transduction buffer can be determined by methods known in the art using an osmometer or can be calculated, e.g. if the osmolar pressure of the media which makes up the remaining volume of the buffer is known. Thus, the salt or further osmolality-inducing component can be added to adjust the osmolality of the buffer to the desired level.

Osmolality is the concentration of a solution in terms of osmoles of solutes per kilogram of solvent. It differs from osmolarity which is the concentration of osmoles of solutes per volume of solvent. Osmolarity is temperature dependent because water changes its volume with temperature. Therefore, osmolality is the preferred measure because it is not temperature dependent. If the concentration of solutes is very low, osmolarity and osmolality are considered equivalent.

Tonicity, by contrast, is defined by the concentration of all solutes that do not cross a cell membrane, i.e. the concentration of solutes that result in osmotic pressure across a cell membrane. In the context of the transduction buffer, hyperosmolality is achieved using hypertonic salts in combination with a further non-salt hypertonic component, as described above. For the transduction method to work, it is important that there is osmotic pressure across the cell membrane. Thus, whilst the transduction buffer can be defined by osmolality (in isolation of the cell), the method of transduction requires the transduction buffer to be hypertonic with respect to the cell cytosol. A cell placed in a hypertonic solution, such as a transduction buffer described herein, will lose water by osmosis. This causes the cell to shrink and tends to increase the space in between cells in a population. To compensate for the loss in cell volume, the cells activate macropinocytosis, i.e. the influx of macromolecules from the extracellular environment. It is to be understood that the optimum osmolality of the transduction buffer is cell-type specific and is defined, in part, by the osmolality of the culture media used to maintain the cell prior to transduction and/or the osmolality of the cell cytosol.

Thus in some embodiments, the method for transducing a molecule of interest into a cell involves the step of increasing the osmotic pressure outside of the cell. In some embodiments, there is osmotic pressure across the cell membrane. In some embodiments, the transduction buffer is hypertonic with respect to the culture media in which the cell was maintained prior to transduction and/or with respect to the cell cytosol. In other words, in some embodiments, the osmolality of the transduction buffer is greater than the osmolality of the culture media in which the cell was maintained prior to transduction and/or greater than the cell cytosol.

Normal osmolality of human serum is about 275-295 mOsm/kg. While temporary elevation of serum osmolality has been used to reduce brain edema in stroke patients, prolonged elevated global osmolality in a human can lead to complications and in serious cases can be fatal. For this reason, pharmaceutical compositions are typically isotonic (have approximately the same osmolality as serum). Individual cells, however, can survive at much higher osmolalities (e.g. up to about 1000 mOsm/kg). Thus, live organisms are able to tolerate moderate elevation of osmolality for several days and temporary high osmolalities locally.

Hyperosmolality refers to an abnormal increase in the osmolality of a solution, especially a body fluid or culture medium. The osmolality at which human cells are maintained is typically about 275-295 mOsm/Kg but, for example, preimplantation embryos are grown at an osmolality of about 250-260 mOsm/Kg. Therefore, in the context of a typical human cell, hyperosmolality refers to an osmolality of more than about 250 mOsm/kg. Thus a transduction buffer with an osmolality of more than about 295 mOsm/kg is likely to be hypertonic with respect to a typical human cell, whereas a transduction buffer with an osmolality of more than about 260 mOsm/kg is likely to be hypertonic with respect to early embryos. Hypo-osmolality refers to an abnormal decrease in the osmolality of a solution, especially a body fluid. Therefore, in the context of typical human cells hypo-osmolality refers to an osmolality of less than about 295 mOsm/kg. Thus a transduction buffer with a tonic salt-mediated osmolality of less than about 295 mOsm/kg is likely to be hypotonic with respect to a typical human cell. In the context of a typical embryo, hypo-osmolality refers to an osmolality of less than about 260 mOsm/kg. Thus a transduction buffer with a tonic salt-mediated osmolality of less than about 260 mOsm/kg is likely to be hypotonic with respect to a typical early embryo.

Osmotic shock is a sudden change in the solute concentration around a cell, causing a rapid change in the movement of water across its cell membrane. In a preferred embodiment, the method for transduction does not require or involve hypo-osmotic shock of the cells or a hypo-osmotic environment at any stage. In some embodiments, the method for transducing a cell involves hyperosmotic shock. However, any osmotic shock or stress is preferably kept to a minimum (see section below on osmoprotectants).

In some embodiments, the transduction buffer is not isotonic and/or not iso-osmolar with respect to the culture media in which the cell was maintained prior to transduction and/or with respect to the cell cytosol. In some embodiments, the transduction buffer is not hypotonic with respect to the culture media in which the cell was maintained prior to transduction and/or with respect to the cell cytosol. In a preferred embodiment, the transduction buffer is hypertonic and/or hyperosmolar with respect to the culture media in which the cell was maintained prior to transduction and/or with respect to the cell cytosol.

In a preferred embodiment, the transduction buffer has an osmolality of at least or more than 1250 mOsm/kg, at least 1300 mOsm/kg, at least 1400 mOsm/kg, at least 1500 mOsm/kg, at least 1600 mOsm/kg, at least 1700 mOsm/kg, at least 1800 mOsm/kg, at least 1900 mOsm/kg, at least 2000 mOsm/kg, at least 2100 mOsm/kg, at least 2200 mOsm/kg, at least 2300 mOsm/kg, at least 2400 mOsm/kg, at least 2500 mOsm/kg, at least 2600 mOsm/kg, at least 2700 mOsm/kg, at least 2800 mOsm/kg, at least 2900 mOsm/kg, at least 3000 mOsm/kg, at least 3100 mOsm/kg, at least 3200 mOsm/kg, or optionally approximately 3250 mOsm/kg.

In some embodiments, the transduction buffer has an osmolality of less than 5000 mOsm/kg. For example, the transduction buffer may have an osmolality of less than 4000 mOsm/kg, less than 3000 mOsm/kg or about 2500 mOsm/kg.

In some embodiments the osmolality is in the range of about 1250 mOsm/kg to about 5000 mOsm/kg, about 1300 mOsm/kg to about 5000 mOsm/kg, about 1350 mOsm/kg to about 5000 mOsm/kg, about 1400 mOsm/kg to about 5000 mOsm/kg, about 1500 mOsm/kg to about 5000 mOsm/kg, about 2000 mOsm/kg to about 5000 mOsm/kg, about 2500 mOsm/kg to about 5000 mOsm/kg, about 3000 mOsm/kg to about 5000 mOsm/kg, about 1250 mOsm/kg to about 4000 mOsm/kg, about 1300 mOsm/kg to about 4000 mOsm/kg, about 1350 mOsm/kg to about 4000 mOsm/kg, about 1400 mOsm/kg to about 4000 mOsm/kg, about 1500 mOsm/kg to about 4000 mOsm/kg, about 2000 mOsm/kg to about 4000 mOsm/kg, about 2500 mOsm/kg to about 4000 mOsm/kg, about 3000 mOsm/kg to about 4000 mOsm/kg.

In preferred embodiments the osmolality is more than 1250 mOsm/kg, more than 2500 mOsm/kg or more than 3000 mOsm/kg.

Higher osmolalities may be preferable when the molecule of interest is a poorly soluble protein. For example, an osmolality of about 3250 mOsmol/Kg is preferred, for example, for poorly soluble proteins, e.g. for transduction of the Cas9 nuclease protein, e.g. in the context of CRISPR-Cas9 gene editing.

In general, the greater the osmolality of the transduction buffer, the more efficient the buffer is, i.e. the less time required for transduction. There is also a trade-off because high osmololalities can cause osmotic stress and reduce cell proliferation and/or viability. This can be mitigated by using a combination of a sodium salt and a further osmolality-inducing component to achieve high osmolalities. There are assays in the art that can be used by the skilled person to optimise the time for transduction (the "incubation time" or "transduction time"—see below) and the osmolality of the buffer.

Osmoprotectant for Transduction

The osmolality of the transduction buffer is such that during transduction methods the transduction buffer is hypertonic with respect to the cell. This can cause osmotic stress to cells and in certain circumstances this can reduce cell proliferation or viability (for example, as measured by BrdU incorporation). Addition of osmoprotectants can protect against these effects as disclosed in WO2015/028969.

Osmoprotectants are small molecules that act as osmolytes and help protect cells and organisms from osmotic stress. Chemically, osmoprotectants can be divided into three types: betaines and allied compounds, polyols and sugars (e.g. glycerol, mannitol and trehalose), and amino acids. Betaines are methyl derivatives of glycine in which the nitrogen atom is fully methylated, i.e. they are quaternary ammonium compounds. Other methyl derivatives of glycine useful in the context of this invention include, but are not limited to, sarcosine and dimethylglycine. It will be clear to the skilled person that some of the transduction compounds described herein can thus function as osmoprotectants. A non-limiting example of a transduction compound that also functions as an osmoprotectant is GABA.

However, not all osmoprotectants enhance transduction. Similarly, not all transduction compounds function as osmoprotectants. Therefore, in some embodiments an osmoprotectant is added to the transduction buffer in addition to the transduction compound (which may or may not function as an osmoprotectant in this context).

In some embodiments, the osmoprotectant is a betaine or allied compound, polyol or sugar, and/or an amino acid, for example, selected from glycine, histidine, alanine, isoleucine, arginine, asparagine, leucine, aspartic acid, lysine, glutamic acid, cysteine, methionine, phenylalanine, glutamine, threonine, tryptophan, proline, valine, ornithine, selenocysteine, serine, tyrosine and proline. In some embodiments the osmoprotectant is glycine or a derivative thereof. In some embodiments the osmoprotectant is a methyl derivative of glycine such as sarcosine, dimethylglycine or betaine.

In other embodiments, the osmoprotectant is selected from glycine, glycerol, taurine, glycinebetaine, myo-inositol, glutamine, glutamate, arginine, mannitol and trehalose. In a preferred embodiment, the osmoprotectant is glycine or glycerol.

In some embodiments, the transduction buffer comprises more than one type of osmoprotectant, for example, glycine and glycerol. Glycine and glycerol is paritcularly suitable for use with murine embryonic fibroblast cells, embryonic stem cells and human iPS cells. However, any combination of osmoprotectants may be suitable for use in the transduction buffer of the invention. For example, any combination of osmoprotectants described herein, for example any combination of 2, 3, 4, 5, 6, 7 or all of glycine, glycerol, taurine, glycinebetaine, myo-inositol, glutamine, glutamate, arginine, mannitol and trehalose.

The type (or combination of types) of osmoprotectant selected for use with the invention may depend upon the type of cell to be transduced. The suitability of an osmoprotectant can be easily determined by the skilled person by assays known in the art.

The concentration of osmoprotectant selected for use with the invention may depend upon the type of cell to be transduced but can be easily determined by the skilled person by methods well known in the art. In some embodiments, the osmoprotectant is at a concentration of between about 5 and about 500 mM, between about 1 and about 500 mM, between about 1 and about 400 mM, between about 1 and about 300 mM, between about 1 and about 200 mM, between about 1 and about 100 mM, between about 10 and about 50 mM, between about 15 and about 50 mM, between about 20 and about 40 mM. For example, in some embodiments, the osmoprotectant is used at a concentration of about 15 mM or about 20 mM or about 30 mM. In some embodiments, the osmoprotectant is used at a concentration of at least 15 mM, at least 20 mM, at least 30 mM, at least 40 mM, at least 50 mM at least 60 mM, at least 70 mM, at least 80 mM, at least 90 mM, at least 100 mM, at least 200 mM, at least 300 mM, at least 400 mM or about 500 mM. In some embodiments, the osmoprotectant is used at a concentration of 500 mM or less, 400 mM or less, 300 mM or less, 200 mM or less, 100 mM or less, 50 mM or less, 40 mM or less, 30 mM or less or 20 mM or less. For example, in a preferred embodiment, glycine and/or taurine are used at a concentration of about 15 mM and/or glycerol is used at a concentration of about 30 mM.

In some embodiments, the osmoprotectant is one of the osmoprotectants in Table A below.

TABLE A

| Name | Formula |
|---|---|
| dimethylsulfonioacetate | C4H8O2S1 |
| dimethyl sulfoxide | C2H6O1S1 |
| Ectoine | C6H10N2O2 |
| gamma-butyrobetaine | C7H15N1O2 |
| Hypotaurine | C2H7N1O2S1 |
| Taurine | $C_2H_7NO_3S$ |
| L-dehydro-ascorbate | C6H6O6 |
| L-pipecolate | C6H11N1O2 |
| methylnicotinate | C7H7N1O2 |
| N-acetyl-L-2,4-diaminobutanoate | C6H12N2O3 |
| L-Ndelta-acetylornithine | C7H14N2O3 |
| glutathione disulfide | C20H30N6O12S2 |
| quinine | C20H25N2O2 |
| dimethylsulfoniopropanoate | C5H10O2S1 |
| trimethylamine N-oxide | C3H9N1O1 |
| urea | C1H4N2O1 |
| 2-(beta-D-glucosyl)-sn-glycerol | C9H18O8 |
| 4-aminobutanoate | C4H9N1O2 |
| sym-homospermidine | C8H24N3 |
| alpha-D-galactosyl-(1,1')-sn-glycerol 3-phosphate | C9H17O11P1 |
| 2-(alpha-D-galactosyl)-sn-glycerol 3-phosphate | C9H17O11P1 |
| hexane-1,3,4,6-tetracarboxylate | C10H10O8 |
| stachydrine | C7H13N1O2 |
| 5-oxoproline | C5H6N1O3 |
| acetylcholine | C7H16N1O2 |
| guanidinium | C1H6N3 |
| betaine aldehyde | C5H12N1O1 |
| choline | C5H14N1O1 |
| citrate | C6H5O7 |
| creatine-phosphate | C4H8N3O5P1 |
| glycine betaine | C5H11N1O2 |
| dimethylglycine | C4H9N1O2 |
| arachidonate | C20H31O2 |
| palmitate | C16H31O2 |
| L-carnitine | C7H15N1O3 |
| trans-aconitate | C6H3O6 |
| L-aspartate | C4H6N1O4 |
| (S)-malate | C4H4O5 |
| salicylate | C7H5O3 |
| glycerol | C3H8O3 |
| D-mannitol | C6H14O6 |
| D-sorbitol | C6H14O6 |
| maltitol | C12H24O11 |
| erythritol | C4H10O4 |
| L-arabitol | C5H12O5 |
| xylitol | C5H12O5 |
| 1D-chiro-inositol | C6H12O6 |
| myo-inositol | C6H12O6 |
| galactinol | C12H22O11 |
| L-quebrachitol | C7H14O6 |
| D-pinitol | C7H14O6 |
| D-ononitol | C7H14O6 |
| L,L-di-myo-inositol 1,3'-phosphate | C12H22O14P1 |
| alpha-D-galactose | C6H12O6 |
| alpha-D-mannose | C6H12O6 |
| beta-D-mannose | C6H12O6 |
| beta-D-glucose | C6H12O6 |
| alpha-D-glucose | C6H12O6 |
| aldehydo-D-altrose | C6H12O6 |
| (S)-acetoin | C4H8O2 |
| (R)-acetoin | C4H8O2 |
| alpha-tocopherol | C29H50O2 |
| ubiquinone-8 | C49H74O4 |
| agmatine | C5H16N4 |
| spermidine | C7H22N3 |
| putrescine | C4H14N2 |
| L-citrulline | C6H13N3O3 |
| L-histidine | C6H9N3O2 |
| L-methionine | C5H11N1O2S1 |
| glycine | C2H5N1O2 |
| L-alanine | C3H7N1O2 |
| L-lysine | C6H15N2O2 |
| L-proline | C5H9N1O2 |
| L-asparagine | C4H8N2O3 |
| L-glutamate | C5H8N1O4 |
| L-isoleucine | C6H13N1O2 |

TABLE A-continued

| Name | Formula |
| --- | --- |
| L-leucine | C6H13N1O2 |
| L-arginine | C6H15N4O2 |
| L-threonine | C4H9N1O3 |
| L-glutamine | C5H10N2O3 |
| L-valine | C5H11N1O2 |
| 1-aminocyclopropane-1-carboxylate | C4H7N1O2 |
| L-ornithine | C5H13N2O2 |
| N6-acetyl-L-lysine | C8H16N2O3 |
| N-acetyl-L-aspartate | C6H7N1O5 |
| N-methyl-L-glutamate | C6H10N1O4 |
| D-octopine | C9H18N4O4 |
| sarcosine | C3H7N1O2 |
| S-methyl-L-methionine | C6H14N1O2S1 |
| D-alanine | C3H7N1O2 |
| creatine | C4H9N3O2 |
| beta-alanine | C3H7N1O2 |
| verbascose | C30H52O26 |
| raffinose | C18H32O16 |
| melibiose | C12H22O11 |
| beta-palatinose | C12H22O11 |
| beta-gentiobiose | C12H22O11 |
| beta-turanose | C12H22O11 |
| sucrose | C12H22O11 |
| beta-maltose | C12H22O11 |
| alpha-maltose | C12H22O11 |
| alpha,alpha-trehalose | C12H22O11 |
| stachyose | C24H42O21 |
| cyclic-GMP | C10H11N5O7P1 |
| 4-phenylbutyrate | C10H11O2 |
| flavone | C15H10O2 |
| 3-hydroxyflavone | C15H9O3 |
| genistein | C15H9O5 |
| daidzein | C15H10O4 |
| O-acetylcarnitine | C9H17N1O4 |
| 2,3-diphospho-D-glycerate | C3H3O10P2 |
| 2-O-alpha-mannosyl-D-glycerate | C9H15O9 |
| 2-[2-O-(alpha-D-mannopyranosyl)-alpha-D-glucopyranosyl]-3-phospho-D-glycerate | C15H24O17P1 |
| 2-O-(alpha-D-glucopyranosyl)-D-glycerate | C9H15O9 |
| L-1-glycero-3-phosphocholine | C8H20N1O6P1 |
| androsterone | C19H30O2 |
| 17beta-estradiol | C18H24O2 |
| progesterone | C21H30O2 |
| ethylene | C2H4 |
| gibberellin A3 | C19H21O6 |
| (−)-jasmonate | C12H17O3 |
| indole-3-acetate | C10H8N1O2 |
| 2-cis-abscisate | C15H19O4 |
| all-trans-beta-carotene | C40H56 |
| N-acetylglutaminylglutamine amide | C12H21N5O5 |
| taurine | C2H7N1O3S1 |
| 3-(N-morpholino)propanesulfonate | C7H14N1O4S1 |
| isethionate | C2H5O4S1 |
| glutathione | C10H16N3O6S1 |
| monodehydroascorbate radical | C6H7O6 |
| L-ascorbate | C6H7O6 |
| a poly-beta-hydroxybutyrate | |
| a 1,2-diacyl-sn-glycerol 3-phosphate | |
| 3-hydroxybutanoate | |
| D-fructose | |

The invention also provides the use of one or more (e.g. 1, 2, 3, 4, 5, 6, 7, 8 or more) osmoprotectants, such as any osmoprotectant or combination of osmoprotectants described herein, for transducing a molecule into a cell. For example, the invention provides the use of glycine and/or glycerol as osmoprotectants for transducing molecules into a cell.

Protein Solubilizing Agent

There are many proteins that are relatively insoluble in hydrophilic buffers (e.g. Cas9). This can limit the amount of protein that is present in the buffer, and so the rate and amount of transduction of the protein into cells. The addition of protein solubilizing agents can enable greater concentrations of such proteins to be achieved in hydrophilic buffers. However, some protein stabilizing agents can interfere with the transduction process and/or are detrimental to cell proliferation and/or viability. The inventors have found that the addition of certain protein stabilizing agents can enhance the solubility of proteins that are otherwise relatively insoluble in hydrophilic buffers without interfering with the transduction process and/or are detrimental to cell proliferation and/or viability.

Accordingly, The invention further provides a method for transducing a molecule of interest into a cell, wherein the method comprises contacting said cell with the molecule of interest and a transduction buffer, wherein the transduction buffer comprises:

(i) a transduction compound,
(ii) one or more salt, wherein the salt is selected from a sodium, rubidium, lithium, potassium or caesium salt;
(iii) one or more protein solubilizing agent, wherein the protein solubilizing agent is (a) a rubidium salt, (b) one or more amino acids and/or (c) a carbohydrate; and
(iv) preferably an osmoprotectant;
and wherein the total salt concentration is preferably between about 400 mM and about 2000 mM.

Accordingly, the invention provides a method for transducing a molecule of interest into a cell, wherein the method comprises contacting said cell with the molecule of interest and a transduction buffer, wherein the transduction buffer comprises:

(i) a transduction compound,
(ii) one or more salt, wherein the salt is selected from a sodium, rubidium, lithium, potassium or caesium salt;
(iii) one or more protein solubilizing agent, wherein the protein solubilizing agent is (i) a rubidium salt and/or (ii) a combination of acidic and basic amino acids and/or (iii) a carbohydrate; and
(v) preferably an osmoprotectant;
wherein the total salt concentration is preferably between about 400 mM and about 2000 mM.

In some embodiments, the protein solubilizing agent is a rubidium salt (e.g. rubidium chloride). In some embodiments, the rubidium salt (e.g. rubidium chloride) is present at a concentration of about 50 mM to about 2 M, about 50 mM to about 1 M, about 50 mM to about 700 mM, about 50 to about 500 mM, about 50 to about 375 mM or about 50 to about 250 mM. Accordingly, in some embodiments, the rubidium salt (e.g. rubidium chloride) is present at a concentration of about 0.7 M, about 0.2 M or about 75 mM. In some embodiments, the rubidium salt (e.g. rubidium chloride) is present at a concentration of less than 0.2 M.

In some embodiments, the protein solubilizing agent is one or more amino acids. In some embodiments, the one or more amino acids are selected from the following: amino acid, for example, selected from glycine, histidine, alanine, isoleucine, arginine, asparagine, leucine, aspartic acid, lysine, glutamic acid, cysteine, methionine, phenylalanine, glutamine, threonine, tryptophan, proline, valine, ornithine, selenocysteine, serine, tyrosine and proline. In some embodiments, the total concentration of amino acids is between about 50 mM and about 1 M, about 50 mM and about 500 mM, between about 50 mM and about 200 mM, between about 50 mM and about 100 mM or between about 100 mM and about 200 mM.

In some embodiments, the protein solubilizing agent is a combination of one or more acidic amino acids (e.g. L-Glu, L-Asp) and one or more basic amino acids (e.g. L-Arg, L-His, L-Lys). In some embodiments, the protein solubilizing agent is a combination of L-Glu and L-Arg. In some embodiments, the total concentration of amino acids is between about 50 mM and about 1 M, about 50 mM and about 500 mM, between about 50 mM and about 200 mM, between about 50 mM and about 100 mM or between about 100 mM and about 200 mM. Accordingly, in some embodiments, the protein solubilizing agent is a combination of L-Glu and L-Arg, wherein the L-Glu is present at a concentration of about 30 to about 50 mM (e.g. about 40 mM) and the L-Arg is present at a concentration of about 40 to about 60 mM (e.g. about 50 mM).

Protein solubilizing agents suitable for use in the transduction buffer and methods of the invention include simple sugars (such as monosaccharides or disaccharides), sugar alcohols, and polyethylene glycols (e.g. PEG). Examples of suitable monosaccharides include glucose, fructose, galactose and ribose. Examples of suitable disaccharides include sucrose, lactose, maltose, trehalose, cellobiose and lactulose. Sugar alcohols are a known class of polyols that are well known for their use as sugar replacements in food. In one embodiment, sugar alcohols have the general formula $HOCH_2(CHOH)nCH_2OH$. Specific examples of suitable sugar alcohols include sorbitol, mannitol, xylitol and erythritol.

Thus, in some embodiments, the protein solubilizing agent is selected from sucrose, lactose, maltose, trehalose, cellobiose, lactulose, glucose, fructose, galactose, ribose, sorbitol, mannitol, xylitol, myo-inositol and erythritol. In a preferred embodiment, the further protein solubilizing agent is selected from sucrose, sorbitol and mannitol. In a most preferred embodiment, the further osmolality-inducing component is sucrose.

In some embodiments, the protein solubilizing agent is one or more sugars (e.g. trehalose, laculose, sorbitol and/or sucrose), one or more amino acids (e.g. L-Arg and/or L-Glu), one or more salts (e.g. sodium, lithium, potassium, rubidium and/or caesium salts), and combinations thereof.

Accordingly, in some embodiments, the protein solubilizing agent comprises sucrose (e.g. about 1%, about 2%, about 3%, about 4%, about 5%, about 6%, about 7%, about 8%, about 9%, about 10%, about 11%, about 12%, about 13%, about 14%, about 15%, about 20% or about 25% sucrose).

In some embodiments, the protein solubilizing agent comprises sorbitol (e.g. about 1%, about 2%, about 3%, about 4%, about 5%, about 6%, about 7%, about 8%, about 9%, about 10%, about 11%, about 12%, about 13%, about 14%, about 15%, about 20% or about 25% sorbitol).

In some embodiments, the protein solubilizing agent comprises a rubidium salt (e.g. at a concentration of about 10 mM to about 2 M, about 10 mM to about 1 M, about 10 mM to about 700 mM, about 10 to about 500 mM, about 10 to about 375 mM or about 10 to about 250 mM) and sucrose (e.g. at a concentration of about 1%, about 2%, about 3%, about 4%, about 5%, about 6%, about 7%, about 8%, about 9%, about 10%, about 11%, about 12%, about 13%, about 14%, about 15%, about 20% or about 25%). Accordingly, in some embodiments, the protein solubilizing agent is a combination of a rubidium salt (e.g. rubidium chloride) and sucrose, wherein the rubidium salt is present at a concentration of about 10 mM to about 250 mM (e.g. 75 mM or 200 mM) and the sucrose is present at a concentration of about 1% to about 10% (e.g. about 5%).

In some embodiments, the transduction buffer further comprises a further osmolality-inducing component, which is added at a concentration to make a buffer osmolality of between about 1500 mOsmol/kg and about 5000 mOsmol/kg.

In some embodiments, the transduction compound, the salt, the further osmolality-inducing component and/or the osmoprotectant is one of the transduction compounds, the salts, the further osmolality-inducing components and/or the osmoprotectants described herein.

In some embodiments, the protein solubilizing agent is also an osmoprotectant. Accordingly, in some embodiments, the protein solubilizing agent is one of the compounds in Table A.

The invention also provides the use of one or more (e.g. 1, 2, 3, 4, 5, 6, 7, 8 or more) protein solubilizing agents, such as any protein solubilizing agent or combination of protein solubilizing agents described herein, for transducing a molecule into a cell. For example, the invention provides the use of a combination of basic and acidic amino acids (e.g. L-Arg and L-Glu) as protein solubilizing agents for transducing molecules into a cell.

Other Components of the Transduction Buffer

It is to be understood that the any of the additional components of the transduction buffer described herein may be part of the transduction buffer. Alternatively, they may be added simultaneously or sequentially to the cells in any combination as a step in the method of transduction.

The transduction buffer may additionally comprise components that make it particularly suitable for use with live cells or live cell culture or application in vivo. For example, in some embodiments the transduction buffer comprises one or more of (e.g. 2, 3, 4, 5, 6 or 7) of a biological pH buffer, a viscosity enhancer, and/or one or more growth factor(s), salts, amino acids, vitamins and nutrients.

A transduction buffer of the invention will normally be formulated in deionized, distilled water, although suitable alternatives may be used including, but not limited to cell culture media or therapeutic solutions. It will typically be sterilized prior to use to prevent contamination, e.g. by ultraviolet light, heating, irradiation or filtration. It may be frozen (e.g. at between −20° C. or −80° C., for examples at −20° C. or at −80° C.) for storage or transport. The transduction buffer may contain one or more antibiotics, such as doxycycline or tetracycline, to prevent contamination. However, some antibiotics, particularly non cell-permeable antibiotics (such as penicillin and/or streptomycin), can be toxic to the cells when transduced into the cells. Therefore, in some embodiments, the transduction buffer does not comprise an antibiotic, for example the transduction buffer does not comprise a non cell-permeable antibiotic. In some embodiments, the transduction buffer does not comprise penicillin.

The transduction buffer may be buffered by a biological pH buffer at a pH of between about 6 and about 8, for example a pH of between about 7.2 and about 7.6 or a pH of about 7.4. A pH outside of this range (i.e. higher than 8 or lower than 6) might be appropriate for administration to particular tissues, as would easily be determined by the person skilled in the art. For example, stomach pH can drop to as low as 1 or 2. Therefore, a transduction buffer for administration to the stomach may have a pH of less than 7, less than 6, less than 5, less than 4, less than 3, less than 2, for example a pH of 7, 6, 5, 4, 3, 2 or 1. A biological pH buffer is a pH buffer that is suitable for use with live cells, i.e. which has minimal negative impact on cell viability. The biological pH buffer may be a carbonate based buffer or any other suitable buffer. A number of biological pH buffers are known in the art (see for example the biological buffers provided in Plant Microtechnique and Microscopy, Oxford University Press, Steven E. Ruzin, ISBN: 0-19-508956-1; and www.sigmaaldrich.com/life-science/core-bioreagents/biological-buffers/biological-buffer-products.html). Examples of biological pH buffers include, but are not limited to PBS, TES, TRIS, PIPES, MOPS, MES, Good's buffers, Trizma or HEPES. Thus in some embodiments the transduction buffer additionally comprises PBS, TES, TRIS, PIPES, MOPS, MES, Good's buffers, Trizma or HEPES. Some of the transduction compounds are also excellent buffering compounds, so can act as buffers instead of, or in addition to, the biological buffer.

The transduction buffer may be supplemented with purified, natural, recombinant, semi-synthetic and/or synthetic growth factors. Any suitable growth factor or combination of growth factors may be used. Non-limiting examples of suitable growth factors include EGF, FGF, HGF, PDGF, BDNF, VEGF or IGF. Any combination of suitable growth factors may be used. Non-limiting examples of growth factor combinations include any one or more (e.g. 1, 2, 3, 4, 5 or 6) of the growth factors in the list consisting of: EGF, FGF (e.g. FGF2, FGF7 or FGF10), HGF, PDGF, BDNF, VEGF or IGF. The growth factors added may, in some circumstances depend on the cell to be transduced, and it is known in the art how to select appropriate growth factors for a particular cell.

The growth factor or growth factors is preferably added at a concentration of between about 1 and about 500 ng/ml or of at least 5 and not higher than 500 ng/ml. A preferred concentration is at least 1, 2, 5, 10, 20, 25, 30, 40, 45, 50, 60, 70, 80, 90, 100, 200, 300, 400 ng/ml and not higher than 600, 500, 450, 400, 350, 300, 250, 200, 150, or 100 ng/ml. A more preferred concentration is at least 10 ng/ml and not higher than 500 ng/ml. An even more preferred concentration is about 50 ng/ml or about 100 ng/ml. The skilled person will be aware that the optimal concentration of a growth factor is both dependent upon the growth factor and the cell to be transduced. The optimal concentration can be determined by methods known in the art and by the methods described in the examples herein.

In some embodiments, the transduction buffer is supplemented with a cytokine. Similarly, to growth factors, different cytokines are suitable for the culture of different cell types and suitable cytokines are known in the art. Other cell type specific factors known in the art can also be added to the transduction buffer, such as, but not limited to LIF (for maintaining the stem cell state of embryonic stem cells) and GM-CSF for dendritic cells.

The invention also provides the use of growth factors, cytokines and/or neurotransmitters and/or small molecule agonists of those signalling pathways for enhancing transduction of a molecule of interest into cell, preferably when used in or with a transduction buffer as described herein.

In some embodiments the transduction buffer additionally comprises a viscosity enhancer. This is particularly preferred when the transduction buffer is for use in vivo because it prevents unwanted dispersion of the transduction buffer. This, therefore, helps to keep the buffer in contact with the cells being transduced. In some embodiments, the viscosity enhancer is polyvinylpyrrolidone (PVP), polyvinyl alcohol, methylcellulose, hydroxypropylmethylcellulose, hydroxyethylcellulose, sodium carboxymethyl cellulose (NaCMC), propylene glycol alginate (PGA) or sodium alginate (SA). A preferred viscosity enhancer is non-toxic and suitable for use with live cells and/or in vivo.

In some embodiments, the transduction buffer additionally comprises an antioxidant, such as ethylenediaminetetraacetic acid (EDTA), sodium bisulfite, sodium metabisulfite, ascorbic acid or thiourea.

In some embodiments, the transduction buffer additionally comprises a basal culture medium. Suitable culture media are available commercially, and include, but are not limited to, Optimem, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, and RPMI 1640 Media.

In some embodiments, the transduction buffer additionally comprises serum. However, in a preferred embodiment, the transduction buffer does not comprise an undefined component such as fetal bovine serum or fetal calf serum. Various different serum replacement formulations are commercially available and are known to the skilled person. Where a serum replacement is used, it may for example be used at between about 0.1% and about 50% by volume of the medium, according to conventional techniques.

Transduction is typically performed in culture medium that is appropriate for the regular maintenance of the particular cell type. As with any of the factors described herein, this culture medium may be part of the transduction buffer or it may be added to the cells separately in the transduction method. In a preferred embodiment, there is no serum or a reduced concentration of serum in the culture medium used during transduction.

The concentration ranges provided for all components of the buffer are final concentrations when the buffer is in use for transduction (e.g. concentrations when the buffer is formulated in deionized, distilled water, cell culture medium or a therapeutic composition).

Proteins for transduction are typically provided in a 5× or 10× concentrate, which when added to the cell culture media gives the concentrations described herein.

Molecule of Interest for Transduction

In a preferred embodiment, more than one molecule of interest (i.e. multiple copies of the molecule of interest) is transduced into a cell. For example, at least 2, at least 10, at least 20, at least 50, at least 100, at least 500, at least 1000, at least 2000, at least 5000, at least 10,000 molecules of interest, at least $10^4$, at least $10^5$, at least $10^6$, at least $10^7$, or more than $10^7$ molecules of interest are transduced into the cell.

The transduction buffer and methods of the invention can be used to transduce many different types of biological and synthetic molecules into cells. For example, the molecule of interest may be a protein (including peptides and polypeptides), nucleic acid, polysaccharide (such as dextran), vesicle (such as an exosome), nanoparticle, small molecule, virus or other organism.

In some embodiments one or more (e.g. 1, 2, 3, 4, 5, 6, 7, 8, 9, 10 or more) different types of molecules of interest are transduced into a cell. In some embodiments, multiple molecules of interest are transduced into the cell, for example in the form of complex mixtures. Non-limiting examples of complex mixtures include cell and/or tissue extracts. For example, extracts from murine embryonic stem cells have been shown to initiate partial reprogramming of the transformed 293T cell line, which was permeabilised using Streptolysin, which creates large pores in the cell membrane. While this method is obviously not well tolerated by cells, it does allow the diffusion of molecules into the cells. The inventors hypothesise that the efficient transduction of cell- or nuclear extracts of murine embryonic stem cells or human pluripotent stem cells into somatic cells such as for example skin fibroblasts, will allow efficient and complete reprogramming of these cells into pluripotent stem cells. Similarly, extracts of other cell types or tissues may confer the identity or functional properties of those cells or tissues onto the transduced cell type.

Accordingly, the invention provides a method for reprogramming a cell, such as a somatic cell, to a pluripotent cell (i.e. an iPS cell). This is also an important tool for identifying new pathways or transcription factors that mediate cell fate or function. Thus in some embodiments, there is provided a method for identifying new pathways or transcription factors that mediate cell fate or function, wherein the method comprises transducing cell and/or tissue extracts into a cell using the transduction methods described herein.

In some embodiments, the molecule of interest is a macromolecule.

In some embodiments, the molecule of interest is a protein. Non-limiting examples of proteins include monoclonal antibodies, cytokines, tissue growth factors and therapeutic proteins. In some embodiments, the molecule of interest is a biological drug (also known as a biologic).

In some embodiments, the protein is an enzyme. For example, the enzyme may be an enzyme that targets and modifies nucleic acids, such as a restriction enzyme, an endonuclease, Cre-recombinase or flippase. In some embodiments the endonuclease is a modified endonuclease, such as a TAL effector nuclease (TALEN) (Boch, J "TALEs of genome targeting". *Nature Biotechnology* 29 (2): 135-6, 2011). Such endonucleases can be used to modify nucleic acids in the cell. For example, they can be designed to target specific DNA sequences to introduce mutations or deletions for gene silencing or activation (e.g. by exon skipping). TALENs can be transduced into cells and that they can introduce genetic mutations, including insertions and deletions. In addition, TALE-DNA binding domains can be coupled to other effector domains, such as a DNA methyltransferase domain (which will methylate cytosine residues in DNA at specific sites), histone modifying domains, such as for example methyltransferase- or acyltransferase domains, which modify histones around the TALE target site, or other protein effector domains. Beta-lactamase is another example of an enzyme which can be transduced by the buffers and methods described herein. Thus in some embodiments, the molecule of interest is beta-lactamase.

In some embodiments, the protein is a transcription factor. Transduction of transcription factors into cells can be used to drive gene expression and to rewire cell fate, phenotype or identity. For example, OCT2, OCT3, OCT4, SOX2, KLF4, C-MYC, N-MYC, NANOG, ESRRB and LIN28 have all been used for the generation of induced pluripotent stem (iPS) cells. Typically, they are introduced into cells by viral vectors. However, the transduction method of the invention could replace this method. Thus, in some embodiments the molecule of interest for transduction is a transcription factor involved in the regulation, definition or change in the cell cycle and/or cell identity. In other embodiments, the transcription factor is a transcription factor involved in the maintenance or differentiation of stem cells. For example, in some embodiments, the transcription factor is selected from OCT2, OCT3, OCT4, SOX2, KLF4, C-MYC, N-MYC, NANOG, ESRRB and LcN28.

A number of transcription factors are also associated with certain diseases and disorders (see table B).

TABLE B

| Condition | Description | References |
|---|---|---|
| Rett syndrome | Mutations in the MECP2 transcription factor are associated with Rett syndrome, a neurodevelopmental disorder. | Moretti P, Zoghbi HY (June 2006). *Curr. Opin. Genet. Dev.* 16 (3): 276-81. Chadwick LH, Wade PA (April 2007). *Curr. Opin. Genet. Dev.* 17 (2): 121-5. |
| Diabetes | A rare form of diabetes called MODY (Maturity onset diabetes of the young) can be caused by mutations in hepatocyte nuclear factors (HNFs) or insulin promoter factor-1 (IPF1/Pdx1). | Maestro MA, Cardalda C, Boj SF, Luco RF, Servitja JM, Ferrer J (2007). *Endocr Dev* 12: 33-45. Al-Quobaili F, Montenarh M (April 2008). *Int. J. Mol. Med.* 21 (4): 399-404. |
| Developmental verbal dyspraxia | Mutations in the FOXP2 transcription factor are associated with developmental verbal dyspraxia, a disease in which individuals are unable to produce the finely coordinated movements required for speech. | Lennon PA, Cooper ML, Peiffer DA, Gunderson KL, Patel A, Peters S. Cheung SW, Bacino CA (April 2007). *Am. J. Med. Genet.* A 143A (8): 791-8. |
| Autoimmune diseases | Mutations in the FOXP3 transcription factor cause a rare form of autoimmune disease called IPEX. | van der Vliet HJ, Nieuwenhuis EE (2007). *Clin. Dev. Immunol.* 2007: 89017. |
| Li-Fraumeni syndrome | Caused by mutations in the tumor suppressor p53. | Iwakuma T, Lozano G, Flores ER (July 2005). *Cell Cycle* 4 (7): 865-7. |
| Breast cancer | The STAT family is relevant to breast cancer. | Garcia, Roy, et al. "Constitutive activation of Stat3 by the Src and JAK tyrosine kinases participates in growth regulation of human breast carcinoma cells." *Oncogene* 20.20 (2001): 2499-2513. |
| Multiple cancers | The HOX family are involved in a variety of cancers. | Grier, D. G., et al. "The pathophysiology of HOX genes and their role in cancer." *The Journal of pathology* 205.2 (2005): 154-171. |
| Muscle disease | Dystrophin mutations lead to Duchenne Muscular Dystrophy. Dux4 expression leads to FSHD | |

Replacement of errant transcription factors by transduction could be useful for therapy or research purposes.

Therefore, in some embodiments, the transcription factor is a transcription factor associated with a disease or disorder. In some embodiments the disease or disorder is selected from a cancer, a metabolic disease, a cardiovascular disease, a neurodegenerative disease, an autoimmune disease. In some embodiments, the disease or disorder is an inherited disease. For example, in some embodiments, the transcription factor is selected from MECP2, HNFs, IPF1/Pdx1, FOXP2, FOXP3, p53, STAT and HOX.

In some embodiments, two or more (e.g. 2, 3, 4, 5, 6, 7 or more) transcription factors are included in the transduction buffer or methods of the invention, for example 2, 3, 4, 5, 6, 7 or all of the transcription 10 factors in the list consisting of MECP2, HNFs, IPF1/Pdx1, FOXP2, FOXP3, p53, STAT and HOX. In some embodiments, when the molecule of interest is a protein, it is protein that can modify nucleic acids, e.g. part of a gene editing system. Examples of gene editing systems include: Zinc finger nucleases (ZFNs), Transcription Activator-Like Effector Nucleases (TALENs), the CRISPR/Cas system, and engineered meganuclease re-engineered homing endonucleases. Proteins that can modify nucleic acids typically have nuclease enzyme activity, for example endonuclease or exonuclease activity. Thus in some embodiments, the molecule of interest has nuclease enzyme activity or is a nuclease. The nuclease activity may be present in the wild type version of the protein or it may be added, e.g. by recombinant methods, to generate a fusion protein. Thus in some embodiments, the molecule of interest is a fusion protein, for example a fusion protein with nuclease activity, for example a transcription factor fused to a domain with nuclease activity. In some embodiments, the molecule of interest is a gene editing system or is part of a gene editing system. In some embodiments, gene editing systems comprise a protein that can modify a nucleic acid as discussed above and optionally comprise further molecules, such as guide molecules. In some embodiments the gene editing system comprises or consists of proteins that target a specific sequence, such as zinc finger nucleases (ZFNs) or TALENS. In some embodiments, the gene editing system comprises a protein that is guided to its target sequences by a (separate) guide molecule. Examples of such proteins that are guided to their target sequence include but are not limited to Cas9 nuclease, proteins from the Cascade system, TtAgo and other Argonaute proteins, and other FOKI-nuclease associated proteins.

In some embodiments, the guide molecule is a guide nucleic acid, such as an sgRNAs or gDNA. Guide nucleic acids, such as sgRNA or gDNA can be designed by methods known in the art to target a specific sequence in the target nucleic acid (see for example, Mali, P., et al., RNA-guided human genome engineering via Cas9. Science, 2013. 339 (6121): p. 823-6 for sgRNA; and Swarts, D. et al, DNA-guided DNA interference by a prokaryotic Argonaute. Nature, 2014. 507, 258-261 for gDNA). Thus, in some embodiments, the molecule of interest is a guide nucleic acid, for example an sgRNA or a gDNA (see further comments below in connection with nucleic acids).

In some embodiments, the protein is a signalling molecule. In some embodiments, the protein activates or inhibits a specific signalling pathway or a network of signalling pathways. For example, in some embodiments the protein activates or inhibits a growth factor-induced signalling pathway, a cytokine signalling pathway or a hormone-induced signalling pathway. In some embodiments the protein activates or inhibits a signalling pathway selected from Wnt, Hedgehog, BMP, SMAD, Hippo, Notch, JAK/STAT, NF-kB, cAMP, PLC or other signalling pathway known in the art (e.g. see Cell Signalling Biology, Michael J. Berridge, Module 2, Cell Signalling Pathways, Portland Press Limited 2012).

In some embodiments, the molecule of interest is an antibody. Typically, antibodies are extracellular molecules. Therefore, when found associated with targets within cells they are targeted for destruction, together with any target molecule that they are bound to. Thus, the inventors hypothesise that by targeting antibodies to intracellular targets and transducing them into the cell using the transduction buffers and methods of the present invention, said intracellular targets could be specifically targeted for destruction. Antibodies targeting intracellular targets are sometimes called "intrabodies". Internalization of cancer-fighting antibodies may support cancer therapy by blocking of tumour-specific protein-protein interactions (Bitler, B. G. and Schroeder, J. A. Recent Patents on Anti-Cancer Drug Discovery, 5:99-108, 2010).

In some embodiments, the protein of interest is less than 10, less than 20, less than 40, less than 70, less than 100, less than 150, less than 200, less than 300, less than 750, less than 1000, less than 1500, less than 2000, less than 5000, less than 10,000 amino acids in length. In other embodiments, the protein of interest is 5 or more, 10 or more, 20 or more, 40 or more, 70 or more, 100 or more, 150 or more, 200 or more, 300 or more, 750 or more, 1000 or more, 2000 or more, 5000 or more amino acids in length. In some embodiments, the protein of interest may be any range in length selected from any of the above values. In some embodiments, the protein is 10-5000, 12-1800, 30-1200, 35-800, 40-500, 5-200, 5-50, 5-30, 5-20, 5-12, 2-50, 2-30, 2-20, or 2-12 amino acids in length.

In a preferred embodiment of the invention, the transduction compound, buffer or method is suitable for transduction of a protein into a cell. In a further preferred embodiment, the transduction compound, buffer or method is suitable for transduction of a protein and nucleic acid into a cell, either simultaneously, sequentially or separately.

In embodiments in which the molecule of interest is a nucleic acid, the nucleic acid is DNA, cDNA, RNA, miRNA, siRNA or any modified version thereof. In some embodiment, the nucleic acid is an oligonucleotide or a polynucleotide. In some embodiments the nucleic acid is an antisense oligonucleotide. In some embodiments, the nucleic acid is a two-dimensional or three-dimensional nucleic acid structure, such as a DNA cage (e.g. for drug delivery). The DNA may be synthetic, recombinant, foreign or native to the cell that it is transduced into. In some embodiments the DNA is plasmid DNA. Plasmid DNA is usually taken up by endocytosis. However, the inventors have surprising shown that, using the transduction buffer, they can shift the mechanism of nucleic acid uptake from being primarily by endocytosis to primarily by macropinocytosis. This means that nucleic acids and enzymes targeting nucleic acids for recombination and modification can be transduced into cells simultaneously for genetic modification and gene therapy. In some embodiments, the nucleic acid has a region of homology to a sequence of interest with the cell, for example to allow homologous recombination. In some embodiments, the nucleic acid is small guide RNA (sgRNA), for example, for use with the CRISPR/Cas9 gene editing system or other gene editing systems, or a small guide DNA (gDNA), for example, for use with the TtAgo gene editing system or other gene editing systems. In some embodiments, the molecule of interest is not a nucleic acid.

In some embodiments, the nucleic acid of interest is less than 10, less than 20, less than 40, less than 70, less than 100, less than 150, less than 200, less than 300, less than 750, less than 1000, less than 1500, less than 2000, less than 5000, less than 10,000 nucleotides, less than 15,000 nucleotides, less than 20,000 nucleotides, less than 50,000 nucleotides, less than 100,000 nucleotides, less than 200,000 nucleotides, less than 250,000 nucleotides (or equivalent bases) in length. In other embodiments, the nucleic acid of interest is 1 or more, 5 or more, 10 or more, 20 or more, 40 or more, 70 or more, 100 or more, 150 or more, 200 or more, 300 or more, 750 or more, 1000 or more, 2000 or more, 5000 or more, 10,000 or more, 20,000 or more, 50,000 or more, 100,000 or more, 200,000 or more, 250,000 or more nucleotides (or equivalent bases) in length. In some embodiments, the nucleic acid of interest may be any range in length selected from any of the above values. In some embodiments, the nucleic acid is 10-10,000, 10-5000, 12-1800, 30-1200, 35-800, 40-500, 2-50, 5-30, 5-20, or 5-12 nucleotides (or equivalent bases) in length. In some embodiments, the molecule of interest is a whole or a part of a chromosome.

In some embodiments, the molecule of interest is between about 30 kDa to about 500 kDa, for example between about 30 kDa and about 200 kDa. For example, in some embodiments, the molecule of interest is about 30, about 40, about 50, about 60, about 70, about 80, about 90, about 100, about 110, about 120, about 130, about 140, about 150, about 160, about 170, about 180, about 190, or about 200 kDa. The inventors have demonstrated that molecules ranging from about 30 kDa (e.g. Oct-4) to about 140 kDa (e.g. a TALEN protein) can be transduced into cells using the buffer and methods of the invention. In some embodiments, the molecule of interest is more than 30, more than 40, more than 50, more than 60, more than 70, more than 80, more than 90, more than 100, more than 110, more than 120, more than 130, more than 140, more than 150, more than 160, more than 170, more than 180, more than 190, or more than 200 kDa. These sizes are particularly applicable where the molecule of interest is a protein or peptide. Where the molecule of interest is a nucleic acid molecule, such as an oligonucleotide or a polynucleotide, the size is typically defined by the number of nucleotides. In some embodiments, the molecule of interest is a small molecule. A small molecule is typically a low molecular weight (<800 Daltons) organic compound that may serve as an enzyme substrate or regulator of biological processes.

Transduction of small molecules is useful for drug delivery.

In some embodiments, the molecule of interest is a macromolecule.

In some embodiments, the molecule of interest has a net positive charge. In another embodiment, the molecule of interest has a net negative charge. In some embodiments, the molecule of interest is zwitterionic. In some embodiments, the molecule of interest is polar. In another embodiment, the molecule of interest is non-polar. In some embodiments, the molecule of interest is predominantly hydrophobic. In another embodiment, the molecule is hydrophilic. In another embodiment, the molecule is neutral. In some embodiments, the molecule of interest is soluble at about pH 7. The solubility may be improved by the transduction buffer.

In some embodiments, the transduction buffer comprises the molecule of interest for transduction. In other embodiments the transduction buffer comprises more than one molecule of interest for transduction, for example two, three, four, five or more molecules of interest.

Any combination of molecules of interest described herein may be included in the transduction buffer or used in the methods for transduction disclosed herein. For example, in one embodiment, the transduction buffer comprises a nucleic acid and a protein, such as an endonuclease or Cre-recombinase (e.g. for genetic modification of said nucleic acid) as molecules of interest for transduction. In some embodiments, the transduction buffer comprises a protein and a polysaccharide as molecules of interest for transduction. In some embodiments, the transduction buffer comprises a nucleic acid and a lipid as molecules of interest for transduction. In some embodiments, the transduction buffer comprises a nucleic acid, a protein and a lipid as molecules of interest for transduction.

In some embodiments, the methods for transduction involve the following non-limiting examples of combinations of molecules of interest: two or more different proteins (such as TALEN pairs), two or more nucleic acid molecules, nucleic acid and protein (such as DNA and protein), polysaccharides (such as dextran) and protein, nucleic acid and lipid, protein and lipid, nucleic acid, and protein and lipid. Specific examples of nucleic acid and protein pairs include guide nucleic acids and proteins with nuclease activity, for example sgDNA and Cas9, or gDNA and TtAgo. In some embodiments, the nucleic acid and protein are present as nucleic acid-protein complexes.

The same principle applies for the methods of the invention, i.e. the cell may be contacted with two, three, four, five or more molecules of interest. For example, a TALEN protein and a nucleic acid and optionally a lipid may be transduced into a cell simultaneously.

The concentration of the molecule of interest for transduction depends upon the molecule of interest, the cell, and the purpose of transduction. The skilled person can determine the appropriate concentration. In some embodiments, the molecule of interest for transduction is added at millimolar, micromolar or nanomolar concentrations. In some embodiments, the molecule of interest is added to the transduction buffer at a concentration of between about 1 nM and about 1 mM, between about 10 nM and about 500 μM, between about 10 nM and about 100 μM, between about 10 nM and about 50 μM, between about 10 nM and about 10 μM, between about 10 nM and about 1 μM, between about 10 nM and about 500 nM, between about 10 nM and about 100 nM, between about 50 nM and about 100 nM, between about 100 nM and about 500 nM, between about 100 nM and about 1 μM, between about 100 nM and about 5 μM, between about 100 nM and about 10 μM, between about 100 nM and about 50 μM, or between about 100 nM and about 100 μM. Where the molecule of interest is a protein, the concentration may be between about 10 nM and about 1 mM, for example between 10 nM and 100 μM, or between about 100 nM and about 1 μM. In some embodiments, the concentration of the molecule of interest is between about 1 μM and about 5 μM, for example about 1 μM or about 5 μM.

In some embodiments, the molecule of interest is not modified. For example, in some embodiments, the molecule of interest is not associated with a carrier molecule and/or does not comprise a tag, wherein the tag facilitates transduction into the cell. For example, in one embodiment, the protein of interest is not tagged with a cell penetrating peptide or TAT protein. In a further example, in one embodiment nucleic acid is naked nucleic acid. It is surprising that using methods of the invention, any molecule of interest can be transduced into a cell without modification. In some embodiments, the molecule of interest is not in a complex with the transduction compound. In some embodiments, the molecule of interest is not in or associated with a micelle or a liposome. In some embodiments, the molecule of interest is not in a complex with the transduction compound. In some embodiments, the molecule of interest is not in or associated with a viral vector.

The methods and buffers described herein can be used to transduce viruses into cells (for example, as described in WO 2015/028969). Therefore, in some embodiments, the invention provides a method for transducing a virus into a cell or population of cells, wherein the method comprises contacting a cell or population of cells with a transduction buffer and contacting the cell or population of cells with a virus. In one embodiment, the invention provides a method for transducing a virus into a cell or population of cells, wherein the method comprises contacting a cell or population of cells with a transduction buffer according to the present invention and contacting the cells with a virus. The transduction buffer may be mixed with the virus before administration to the cells or may be administered simultaneously, sequentially or separately from the virus.

In addition, it has been observed that in the presence of transduction buffer a population of cells shrinks creating space between the cells and making the cells more accessible. This could further enhance the transduction of viruses into cells. Thus, in some embodiments, the method of transducing a molecule of interest into cells involves reduction in the size of the cells and/or increase in space between cells. Without wishing to be bound by theory, the inventors hypothesise that the shrinking is a result of the hyperosmolality in the transduction buffer. Nevertheless, the macropinocytosis mechanism already described above is still likely to play an important role in enhancing transduction of viruses into cells.

Cell for Transduction

The transduction method can be used to transduce a molecule of interest into any cell, including a primary cell or a stem cell (including their derivatives, such as progenitor cells), a normal healthy cell or a diseased cell.

In a preferred embodiment, the cell involved in the transduction method is a mammalian cell. This is because the transduction buffer and method are thought to be particularly well suited to the mammalian macropinocytosis system (see below for more details). However, it is also envisaged that in some embodiments, the methods might be useful for transducing molecules into other animal cells, plant cells, yeast cells, insect cells, or bacterial cells. Thus, in some embodiments, the cell is an animal cell, a plant cell, a yeast cell, an insect cell or a bacterial cell. In some embodiments, the cell is not a bacterial cell.

In preferred embodiments, the mammalian cell is a human, primate, rodent (e.g. mouse or rat), rabbit, dog, cat, horse, cow or pig cell. These mammals are useful for research purposes and/or may benefit from treatment or diagnosis comprising transduction buffers and methods of the invention. In some embodiments, the cell is a non-human cell.

In some embodiments the cell is in vivo, optionally in situ. For example, when treating or diagnosing a medical condition, the molecule of interest could be administered directly and locally in combination with the transduction buffer to an organism or tissue in need thereof.

In an alternative embodiment, the cell is in vitro. For example, the cell may be in a culture medium, wherein the culture medium optionally supports the maintenance, differentiation and/or expansion of the cell.

In some embodiments, the cell is derived from an established cell line, such as an established human cell line. In some embodiments, the established cell line is an immortalised cell line. In other embodiments the cell line is a primary cell line. Several prior art methods for transduction do not work in primary cells (see background section). Therefore, it is surprising that the transduction buffers and methods of the present invention can be used to transduce molecules into primary cells.

Examples of established human cell lines suitable for use in the context of the invention include but are not limited to HeLa, ESTDAB database, DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), COS7 (immortalised CV-1 cells from kidney tissue), U87 (glioblastoma), SHSY5Y human neuroblastoma cells, cloned from a myeloma, Saos-2 cells (bone cancer). The ESTDAB database (www.ebi.ac.uk/ipd/estdab/directory.html) and National Cancer Institute (NCI-60) provide further examples of cancer cell lines which are suitable for use with the present invention. In some embodiments, the established cell line is a primate cell line, such as Vero (African green monkey Chlorocebus kidney epithelial cell line initiated in 1962). In some embodiments, the established cell line is a rodent cell line, such as GH3 (pituitary tumor), PC12 (pheochromocytoma) or MC3T3 (embryonic calvarium). Other mammalian cell lines suitable for use with the transduction buffer and methods disclosed herein include the Madin-Darby canine kidney (MDCK) epithelial cell line, Chinese hamster ovary (CHO) cell line and Caco-2 cells. In some embodiments the cell is a KBM7 cell.

In some embodiments, the cell is a primary cell. A primary cell or cell line is derived from a cell taken directly from a living organism, and has not been immortalized. In other words, a primary cell or cell line is genetically and phenotypically stable.

In some embodiments, the cell is a stem cell or a cell derived by differentiation of a stem cell. In some embodiments the stem cell is a pluripotent stem cell, such as an embryonic stem cell, optionally a human embryonic stem cell. In some embodiments, the cell is not a human embryonic stem cell. In some embodiments, the stem cell is not obtained by methods that involve the use of human embryos for commercial or industrial purposes. In some embodiments, the stem cell is not obtained by methods that necessarily involve the destruction of a human embryo. In some embodiments the stem cell is a murine embryonic stem cell. In other embodiments, the stem cell is an adult stem cell, such as a neural, adipose or hematopoietic stem cell. In some embodiments the cell is a murine or human neural stem cell, neuron cell or glia cell. In some embodiments the stem cell is an induced pluripotent stem cell. In some embodiments the cell is a somatic cell or a germ cell.

In some embodiments, the cell is a cell belonging to the immune system, such as a T cell, B cell or leukocyte, including but not limited to a phagocyte (macrophage, neutrophil, or dendritic cell), mast cell, eosinophil, basophil, and natural killer cell. In some embodiments, the cell is a dendritic cell.

In some embodiments the cells for transduction are cultured in an atmosphere comprising between about 4% and about 10% $CO_2$, about 5% and about 9% $CO_2$, about 6% and about 8% $CO_2$, preferably about 5% $CO_2$.

In all embodiments, where the disclosure refers to a "cell", it refers to a single cell and also applies to a "cell population", for example of 2 or more, 10 or more, 100 or more, 1000 or more, $10^4$ or more, $10^5$ or more, $10^6$ or more, $10^7$ or more, $10^8$ or more cells.

Thus, the invention also provides a transduced cell or population of cells obtained or obtainable using the transduction buffer and/or the methods described herein. The invention provides a cell or population of cells comprising a molecule of interest wherein the molecule of interest has been transduced into the cell using the transduction buffer and/or methods described herein.

Cell Viability

In a preferred embodiment, the transduction buffer and methods of the invention have minimal impact on the viability of the cells. Cell viability is important for many applications of the transduced cells, including but not limited to transplantation of transduced cells; the use of transduced cells to generate genetically modified embryos for research models; and the use of transduced cells in research etc (see section on "Uses of the invention"). One measure of cell viability is cellular proliferation (e.g the BrdU incorporation assay). Continuing cellular proliferation demonstrates that the normal cell cycle is still functioning.

Assays to measure proliferation, viability and cytotoxicity are known in the art and available commercially (e.g. from Sigma Aldrich). Such assays can be used to monitor the response and health of cells in culture after treatment with various stimuli. The proper choice of an assay method depends on the number and type of cells used as well as the expected outcome. Assays for cell proliferation may monitor the number of cells over time, the number of cellular divisions, metabolic activity or DNA synthesis. Cell counting using viability dyes such as trypan blue or calcein-AM can provide both the rate of proliferation as well as the percentage of viable cells. 5(6)-Carboxyfluorescein diacetate N-succinimidyl ester (CFSE) is a popular choice for measuring the number of cellular divisions a population has undergone. Upon entering the cell, CFSE is cleaved by intracellular esterases to form the fluorescent compound and the succinimidyl ester group covalently reacts with primary amines on intracellular proteins. Upon division, the fluorescence intensity of each daughter cell is halved which allows for the simple detection of the number of cell divisions by flow cytometry. Assays that measure metabolic activity are suitable for analyzing proliferation, viability, and cytotoxicity. The reduction of tetrazolium salts such as MTT and XTT to coloured formazan compounds or the bioreduction of resazurin only occurs in metabolically active cells. Actively proliferating cells increase their metabolic activity while cells exposed to toxins will have decreased activity.

An example of an assay that measures proliferation is the BrdU incorporation assay, which measures BrdU incorporation into cellular DNA during cell proliferation.

In a preferred embodiment, when the cells being subjected to the transduction methods of the invention are subjected to the BrdU incorporation assay, more than 50%, more than 55%, more than 60%, more than 65%, more than 70%, more than 75%, more than 80%, more than 85%, more than 90%, more than 95%, more than 99% or all cells demonstrate incorporation of BrdU into cellular DNA of the cells.

Viability of cells can also be assessed by staining for markers of apoptosis (e.g. annexin V, caspases activators etc) or by assessing propidium iodide uptake as a sign of cell death. Cells that do not stain positive for such markers of apoptosis (e.g. AnnexinV, caspase activation) or that do not take up propidium iodide are viable cells.

In a preferred embodiment, more than 50%, more than 55%, more than 60%, more than 65%, more than 70%, more than 75%, more than 80%, more than 85%, more than 90%, more than 95%, more than 99% or all cells are viable after one, two, three, four or five rounds of transduction, as assessed using annexin V staining. In a preferred embodiment, more than 75% of the cells are viable after transduction, as assessed using annexin V staining.

Transduction of certain molecules can trigger cell death pathways in cells. For example, foreign DNA/RNA introduced into cells can trigger the interferon response pathway which can result in cell death. In some embodiments, the methods and/or transduction buffer of the invention uses/comprises one or more inhibitors of cell death. Inhibitors of cell death, such as inhibitors of the interferon response pathway, can help to prevent the apoptotic response and thus improve cell survival. Such inhibitors can act at several levels of the interferon response pathway, for example, they may be inhibitors of extracellular binding of interferon to its receptor, inhibitors of intracellular interferon signalling, inhibitors of downstream effectors of the Interferon response (e.g. RNaseL, PKR, Jak/STAT signalling, Mx inhibitors). Other types of inhibitors that may be used include proteins or small molecule compounds that can ameliorate detection of foreign RNA/DNA in the cell, such as the Influenza A NS1 protein. A combination of inhibitors can also be used. Examples of such inhibitors are known in the art. The inventors, for example, used interferon inhibitor protein B18R (Nat Protoc. 2013 March; 8(3):568-82. doi: 10.1038/nprot.2013.019. Epub 2013 Feb. 21. Reprogramming human fibroblasts to pluripotency using modified mRNA. Mandal PK1, Rossi D J; and Cell. 1995 May 19; 81(4):551-60. Vaccinia virus encodes a soluble type I interferon receptor of novel structure and broad species specificity. Symons JA1, Alcamí A, Smith G L.). Therefore, in some embodiments, the transduction buffer further comprises one or more inhibitor of cell death, preferably an inhibitor of the interferon response pathway. In some embodiments the inhibitor is added before, during and/or after transduction. In some embodiments the inhibitor is used at a concentration of about 10 ng/ml to about 1000 ng/ml, about 100 ng/m to about 500 ng/ml, about 200 ng/ml to about 400 ng/ml, about 200 ng/ml to about 300 ng/ml, or about 250 ng/ml. In some embodiments, the inhibitor is B18R, which is preferably used at about 250 ng/ml, before (e.g. 3 hours before) transduction, during transduction and after (e.g. 48 hours after) transduction. Such inhibitors are particularly useful when transducing nucleic acid molecules into cells (for example when transducing small inhibitory RNAs (siRNAs) or small guide nucleic acid molecules, such as sgRNAs or gDNAs, into cells with a nuclease, such as Cas9, in the context of a gene editing system) but may be useful for all types of molecules of interest, particularly those that might activate cell death pathways, particularly via the interferon response pathway. They are compatible with all transduction buffers and protocols described herein.

Efficiency/Time for Transduction

In order to transduce a molecule of interest into a cell, the molecule of interest and cell are in contact for a sufficient length of time for the molecule to transduce into the cell. In general a cell or population of cells will be contacted with many copies of the molecule of interest. Thus in a preferred embodiment, the molecules of interest and cell(s) are in contact for a sufficient length of time for at least 40%, at least 50%, at least 60%, at least 70%, at least 80%, at least 90% or 100% of the molecules to transduce into the cell(s).

Generally, the amount of uptake into the cell correlates with the amount of time the cell is in contact with the transduction buffer and molecule of interest. This is known herein as the "incubation time" or the "transduction time".

In some embodiments, the incubation time is less than 90 minutes, less than 80 minutes, less than 70 minutes, less than 60 minutes, less than 50 minutes, less than 40 minutes, less than 30 minutes, less than 25 minutes, less than 20 minutes, less than 15 minutes, less than 10 minutes, less than 5 minutes, or less than 1 minute. In some embodiments, the incubation time is much longer, e.g. in some embodiments the incubation time is at least 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours or more than 13 hours. In some embodiments, the incubation time is between about 1 minute and about 30 minutes, between about 5 minutes and about 25 minutes, between about 10 minutes and about 20 minutes, or about 15 minutes.

In some embodiments of the invention, the transduction buffer or method allows more than 50%, more than 60%, more than 70%, more than 80%, more than 90%, more than 95% incorporation of 10 μM CRE recombinase into human embryonic stem cells, as determined using a GFP reporter construct (see details in Example 1), in less than 90 minutes, less than 80 minutes, less than 70 minutes, less than 60 minutes, less than 50 minutes, less than 40 minutes, less than 30 minutes, less than 25 minutes, less than 20 minutes, less than 15 minutes, less than 10 minutes, less than 5 minutes, or less than 1 minute.

The rate of transduction will depend upon the cell type (and the efficiency of transduction mechanisms) and the molecule of interest to be transduced (its size, charge, hydrophobicity etc). The inventors have also shown that the higher the osmolality of the transduction buffer, the greater the rate of transduction. Thus, at higher osmolality, the rate of transduction is typically higher and shorter incubation times are required. Conversely, at lower osmolality, the rate of transduction is lower and longer incubation times are required to achieve equivalent levels of transduction.

However, as mentioned elsewhere in this disclosure, hyperosmolality can negatively affect cell viability and therefore, the incubation time must be balanced with osmolality and cell viability. By adding osmoprotectants, the cell viability is protected and thus higher osmolalities and shorter incubation times can be used. The optimum osmolality, incubation time and concentration of osmoprotectants can be determined by the skilled person using trial and error and optimisation tests.

Transduction can be detected qualitatively or quantitatively using reporter constructs known in the art and available commercially, e.g. a luciferase or a GFP reporter construct, wherein levels of fluorescence correspond to levels of expression (see the Examples section for more details).

In some embodiments, the method comprises one round of transduction. However, in other embodiments, multiple rounds of transduction may be desirable. For example, in some embodiments 2, 3, 4, 5, 6, 7, 8, 9, 10 or more rounds of transduction are carried out on the same cells. Each round of transduction may involve transduction of the same molecule or of different molecules of interest.

In between each round of transduction, there may be a "recovery period" of at least 1, at least 2, at least 3, at least 4, at least 5, at least 6, at least 7, at least 8, at least 9, at least 10, at least 11 or at least 12 hours. In some embodiments, the recovery period is at least 10, at least 20, at least 30, at least 40 or at least 50 minutes.

In some embodiments there is no recovery period, or there is a recovery period of less than 24 hours, less than 12 hours, less than 6 hours, less than 3 hours, less than 1 hour, less than 30 minutes or less than 10 minutes.

During the recovery periods, the transduction buffer is removed from the cells and the cells are typically cultured in cell culture medium suitable for the particular cell type.

Exemplary Transduction Buffers and Methods

Non-limiting examples of transduction buffers and methods are provided below. It is to be understood that any combination of compatible embodiments described herein can be used for a transduction buffer or method for transduction comprising a transduction buffer. Some examples of combinable embodiments are provided below.

In some embodiments, there is provided a method for transducing a molecule of interest into a cell, wherein the method comprises contacting the cell with a molecule of interest and contacting the cell with a transduction buffer comprising:
  (i) a transduction compound selected from FIGS. 6A-6D;
  (ii) one or more salt, wherein the salt is selected from a sodium, rubidium, lithium, potassium or caesium salt and is preferably at a total concentration of between about 400 mM and about 2000 mM;
  (iii) a further osmolality-inducing component, which is added at a concentration to make a buffer osmolality of between about 1500 mOsmol/kg and about 5000 mOsmol/kg; and
  (iv) preferably an osmoprotectant.

In some embodiments, there is provided a method for transducing a molecule of interest into a cell, wherein the method comprises contacting the cell with a molecule of interest and contacting the cell with a transduction buffer comprising:
  (i) a transduction compound selected from #42, #1, #45, #43, #44, #15, #10, #11, #28, #37 and #46;
  (ii) one or more salt, wherein the salt is selected from a sodium, rubidium, lithium, potassium or caesium salt and is preferably at a total concentration of between about 400 mM and about 2000 mM;
  (iii) a further osmolality-inducing component, which is added at a concentration to make a buffer osmolality of between about 1500 mOsmol/kg and about 5000 mOsmol/kg; and
  (iv) preferably an osmoprotectant.

In some embodiments, there is provided a method for transducing a molecule of interest into a cell, wherein the method comprises contacting the cell with a molecule of interest and contacting the cell with a transduction buffer comprising:
  (i) a transduction compound, wherein the transduction compound comprises an NDSB, such as NDSB-201, or an NDCB, and in addition comprises a GABA agonist, such as GABA (compound #20);
  (ii) one or more salt, wherein the salt is selected from a sodium, rubidium, lithium, potassium or caesium salt and is preferably at a total concentration of between about 400 mM and about 2000 mM;
  (iii) a further osmolality-inducing component, which is added at a concentration to make a buffer osmolality of between about 1500 mOsmol/kg and about 5000 mOsmol/kg; and
  (iv) preferably an osmoprotectant.

In some embodiments, there is provided a method for transducing a molecule of interest into a cell, wherein the method comprises contacting the cell with a molecule of interest and contacting the cell with a transduction buffer comprising:
  (i) a transduction compound selected from FIGS. 6A-6D, e.g. NDSB-201 and GABA;

(ii) one or more salt, wherein the salt is selected from a sodium, rubidium, lithium, potassium or caesium salt and is preferably at a total concentration of between about 400 mM and about 2000 mM;
(iii) a further osmolality-inducing component, preferably sucrose, which is added at a concentration to make a buffer osmolality of between about 1500 mOsmol/kg and about 5000 mOsmol/kg;
(iv) an osmoprotectant, such as glycine and/or glycerol;
(v) a basal culture medium, for example a reduced serum medium, such as Optimem; and
(vi) optionally one or more growth factor, for example selected from EGF, FGF, HGF, PDGF, BDNF, VEGF and IGF.

In some embodiments, there is provided a method for transducing a molecule of interest into a cell, wherein the method comprises contacting the cell with a molecule of interest and contacting the cell with a transduction buffer comprising:
(i) a transduction compound selected from FIGS. 6A-6D;
(ii) one or more salt, wherein the salt is selected from a sodium, rubidium, lithium, potassium or caesium salt;
(iii) one or more protein solubilizing agent, wherein the protein solubilizing agent is (a) a rubidium salt and/or (b) a combination of acidic and basic amino acids; and
(iv) preferably an osmoprotectant;
and wherein the total salt concentration is preferably between about 400 mM and about 2000 mM.

In some embodiments, there is provided a method for transducing a molecule of interest into a cell, wherein the method comprises contacting the cell with a molecule of interest and contacting the cell with a transduction buffer comprising:
(i) a transduction compound selected from #42, #1, #45, #43, #44, #15, #10, #11, #28, #37 and #46;
(ii) one or more salt, wherein the salt is selected from a sodium, rubidium, lithium, potassium or caesium salt;
(iii) one or more protein solubilizing agent, wherein the protein solubilizing agent is (a) a rubidium salt and/or (b) a combination of acidic and basic amino acids; and
(iv) preferably an osmoprotectant;
and wherein the total salt concentration is preferably between about 400 mM and about 2000 mM.

In some embodiments, there is provided a method for transducing a molecule of interest into a cell, wherein the method comprises contacting the cell with a molecule of interest and contacting the cell with a transduction buffer comprising:
(i) a transduction compound, wherein the transduction compound comprises an NDSB, such as NDSB-201, or an NDCB, and in addition comprises a GABA agonist, such as GABA (compound #20);
(ii) one or more salt, wherein the salt is selected from a sodium, rubidium, lithium, potassium or caesium salt;
(iii) one or more protein solubilizing agent, wherein the protein solubilizing agent is (a) a rubidium salt and/or (b) a combination of acidic and basic amino acids; and
(iv) preferably an osmoprotectant;
and wherein the total salt concentration is preferably between about 400 mM and about 2000 mM.

In some embodiments, there is provided a method for transducing a molecule of interest into a cell, wherein the method comprises contacting the cell with a molecule of interest and contacting the cell with a transduction buffer comprising:
(i) a transduction compound selected from FIGS. 6A-6D, e.g. NDSB-201 and GABA;
(ii) one or more salt, wherein the salt is selected from a sodium, rubidium, lithium, potassium or caesium salt;
(iii) one or more protein solubilizing agent, wherein the protein solubilizing agent is (a) a rubidium salt and/or (b) a combination of acidic and basic amino acids;
(iv) an osmoprotectant, such as glycine and/or glycerol;
(v) a basal culture medium, for example a reduced serum medium, such as Optimem; and
(vi) optionally one or more growth factor, for example selected from EGF, FGF, HGF, PDGF, BDNF, VEGF and IGF;
and wherein the total salt concentration is preferably between about 400 mM and about 2000 mM.

Genetic Modification of Nucleic Acids

In some embodiments, the transduction buffer and methods can be used for transduction of a protein that is capable of modifying a nucleic acid or of a gene editing system into cells. In some embodiments, there is provided a method for transducing a protein that is capable of modifying a nucleic acid or a gene editing system, such as a Cas9 nuclease and an sgRNA, into a cell, wherein the method comprises contacting the cell with the gene editing system and a transduction buffer of the invention.

The invention also provides a method for modifying a nucleic acid, such as a genetic sequence, in a cell, wherein the method comprises contacting said cell with a protein capable of modifying a nucleic acid and a transduction buffer and a transduction buffer of the invention.

In some embodiments, the protein capable of modifying a nucleic acid is targeted to a specific target sequence, for example wherein the protein is a zinc finger nucleaseor a TALEN, Cas9, a Cas9 analog, a DNA-targeted FokI-nuclease-associated protein, a Cascade complex, a TtAgo protein or other Argonaute protein or their derivatives. In some embodiments, the cell is further contacted with a guide molecule to direct the protein to a target genetic sequence. Comments elsewhere in this document about genetic modification and gene editing systems are applicable to the method for modifying a nucleic acid described in this section.

In some embodiments, the osmolality is adjusted to between about 2000 mOsm/kg and about 5000 mOsm/kg, preferably about 3250 mOsm/kg. In some embodiments, transduction is carried out for about 5 minutes to about 30 minutes or about 15 minutes.

In some embodiments, the transduction buffer further comprises an inhibitor of the interferon response pathway, for example, B18R. In some embodiments, the cell is a stem cell, such as an iPS cell or a stem cell line, including for example human stem cell lines. In some embodiments, the osmoprotectant is selected from selected from glycine, glycerol, taurine, glycinebetaine, myo-inositol, glutamine, glutamate, arginine, mannitol and trehalose.

In some embodiments, in the method for modifying a nucleic acid, such as a genetic sequence, in a cell, the protein capable of modifying a nucleic acid is present in the cell for less than 10 days, less than 5 days, less than 4 days, less than 3 days, less than 2 days, less than 1 day, less than 12 hours, less than 6 hours, or less than 1 hour. If the protein capable of modifying a nucleic acid is present in the cell for too long, it can start to have damaging off-target effects (i.e. modify non-target sequences). This is often a problem with traditional forms of transfection which involve expression of the protein from an expression plasmid over a number of days.

In some embodiments, the method for modifying a nucleic acid, such as a genetic sequence, in a cell, further comprises isolating or using the modified cell. The invention also provides a modified cell obtainable or obtained by these methods. In some embodiments the modified cell comprises a transduced gene editing system. In some embodiments, the modified cell does not comprise a viral vector. In some embodiments, the modified cell does not comprise a nanoparticle carrier. In some embodiments, the cell does not comprise a cell penetrating peptide.

Pharmaceutical Composition

In some embodiments, the invention provides a pharmaceutical composition comprising the transduction buffer of the invention and a molecule of interest for transduction. In some embodiments, the invention provides a pharmaceutical composition comprising the transduction buffer. In some embodiments, the molecule of interest and transduction buffer components are administered simultaneously or sequentially.

The pharmaceutical composition can include further components in addition to the transduction buffer and a molecule of interest. For example, a pharmaceutical composition will usually include a pharmaceutically acceptable carrier, which can be any substance that does not itself induce the production of antibodies harmful to the patient receiving the composition, and which can be administered without undue toxicity. Suitable pharmaceutically acceptable carriers are well known in the art. Pharmaceutically acceptable carriers can, for example, include liquids such as water, saline, glycerol and ethanol. Auxiliary substances, such as wetting or emulsifying agents, pH buffering substances, and the like, can also be present in pharmaceutical compositions (see Gennaro (2000) Remington: The Science and Practice of Pharmacy. 20th edition, ISBN: 0683306472).

In some embodiments, there is provided a pharmaceutical composition comprising a transduction compound or transduction compound and a protein capable of modifying a nucleic acid, such as a gene editing system.

The pharmaceutical composition may be sterile and/or pyrogen-free.

The invention also provides a container (e.g. vial) or delivery device (e.g. syringe) pre-filled with a pharmaceutical composition of the invention. The invention also provides a process for providing such a container or device, comprising introducing into the container or device a composition of the invention.

The appropriate dose may vary depending upon the health and physical condition of the individual to be treated, age, the taxonomic group of individual to be treated (e.g. human, non-human primate, primate, etc.), the degree of transduction desired, the formulation of the pharmaceutical composition, the treating doctor's assessment of the medical situation, and other relevant factors. The dose may fall in a relatively broad range that can be determined through routine trials.

Compositions of the invention may be prepared in various liquid forms. For example, the compositions may be prepared as injectables, either as solutions or suspensions. Injectables for local sub-cutaneous or intramuscular administration are typical. Injection may be via a needle (e.g. a hypodermic needle), but needle-free injection may alternatively be used.

Compositions may include an antimicrobial. Antimicrobials such as thiomersal and 2-phenoxyethanol are commonly found in pharmaceutical compositions, but it is preferred to use either a mercury-free preservative or no preservative at all.

Compositions may comprise detergent e.g. a Tween (polysorbate), such as Tween 80. Detergents are generally present at low levels e.g. <0.01%. In some embodiments, the buffer does not comprise a detergent. In some embodiments, the method for transduction does not involve the use of a detergent during transduction.

Effective dosage volumes can be routinely established, depending on the purpose of the composition. Typical human dose of the composition might be, for example about 0.5 ml e.g. for intramuscular injection (e.g. local injection into the muscle or tissue of interest). Similar doses may be used for other delivery routes.

The invention also provides a kit comprising a transduction buffer of the invention or a pharmaceutical composition of the invention. The kit may additionally comprise cells and/or molecules of interest for transduction. The kit may also comprise instructions for use. The kit may include the various components of the transduction buffer in one or more separate containers, e.g. 1, 2, 3, 4, 5, 6 or more separate containers. For example, the kit may comprise a container comprising a salt solution, a container comprising the transduction compound, a container comprising the molecule of interest, a container comprising the osmoprotectant and/or a container comprising a diluent or media. In addition the kit may comprise any one or more of the additional other components as described herein, wherein they are suitable for simultaneous, sequential or separate administration with the transduction buffer.

Uses of the Invention

The invention provides the use of the transduction buffer, for transducing a molecule of interest into a cell.

Transduction of molecules into a cell can be useful for both research and therapeutic reasons.

In some embodiments, the transduction buffers and methods of the invention can be used for genetic modification. For example, in some embodiments, transduction of certain enzymes into cells can result in modification of the cell's genome or modification of foreign nucleic acid sequences. For example, the transduced molecule (such as an enzyme) may result in insertion, deletion, substitution, translocation, inversion or modification of one or more (for example a sequence of 2, 3, 4, 5, 6, 7, 8, 9, 10, 20, 30, 40, 50, 60, 70, 80, 90, 100, 200, 300, 400, 500, 600, 700, 800, 900, 1000, 2000, $10^4$, $10^5$, $10^6$, $10^7$ or more) nucleic acids. For example, Cre-Lox recombination is a site-specific recombinase technology widely used to carry out deletions, insertions, translocations and inversions in the DNA of cells (Turan, S.; Galla, M.; Ernst, E.; Qiao, J.; Voelkel, C.; Schiedlmeier, B.; Zehe, C.; Bode, J. (2011). "Recombinase-mediated cassette exchange (RMCE): traditional concepts and current challenges". *J. Mol. Biol.* 407 (2): 193-221). It allows the DNA modification to be targeted to a specific cell type or be triggered by a specific external stimulus. It is implemented both in eukaryotic and prokaryotic systems. The system consists of a single enzyme, Cre recombinase, which recombines a pair of short target sequences called the Lox sequences. This system can be implemented without inserting any extra supporting proteins or sequences. The Cre enzyme and the original Lox site called the LoxP sequence are derived from a bacteriophage P1. Placing Lox sequences appropriately will allow genes to be activated, repressed, or exchanged for other genes. At a DNA level many types of manipulations can be carried out. The activity of the Cre enzyme can be controlled so that it is expressed in a particular cell type or triggered by an external stimulus, such as a chemical signal or a heat shock. These targeted DNA changes are useful in cell lineage tracing and when mutants are lethal if expressed globally. The Cre-Lox system is very similar in action and in usage to the FLP-FRT recombination system, which involves the recombination of sequences between short flippase recognition target (FRT) sites by the recombinase (Flp) derived from the 2 μm plasmid of *Saccharomyces cerevisiae*. Thus, in some embodiments, the invention provides the use of the transduction buffer in a Cre-Lox or a FLP-FRT recombination system for transducing Cre recombinase or flippase into a cell. The invention also provides a method for transducing a molecule of interest into a cell, wherein the molecule of interest is Cre recombinase or flippase.

In some embodiments, the transduction compound, buffer or method can be used for genetic modification of specific gene sequences, also referred to herein as "gene editing". In some embodiments, the invention also provides a method for modifying a genetic sequence in a cell, wherein the method comprises a transduction method of the invention, and wherein the molecule of interest is a protein capable of modifying a nucleic acid, preferably a specific gene sequence, and optionally is part of a gene editing system.

In recent years, two essentially different gene editing systems have been developed that differ in the way they find their specific genomic target sequence. One type, represented by zinc-finger nucleases (ZFNs) and TALENs, uses customizable domains within the nuclease protein itself to recognize specific target DNA sequence in the genome. The other type is represented by the Cas9/CRISPR, Cascade and TtAgo and other Argonaute protein systems, sometimes coupled as fusion protein to a nuclease domain, such as the FokI nuclease domain, which use a common protein (complex) that is the same regardless of the genomic target site, which is targeted to a specific target by an associated nucleotide sequence (such as an sgRNA or gDNA). Traditionally, these gene editing systems have been transfected into cells as nucleic acids encoding the protein/RNA machinery; the transfected nucleic acids are then expressed within the cells. Traditional methods for nucleic acid transfection involve viral vectors, electroporation or carrier nanoparticles or liposomes. These methods hamper clinical applications and are inefficient for certain cell types as explained elsewhere. By contrast, the transduction compounds, buffers and methods described herein are capable of directly delivering proteins and/or nucleic acids into cells (e.g. as part of gene editing systems) allowing rapid, non-viral and highly efficient gene editing. Thus in some embodiments, the transduction methods of the invention are used for genetic modification, wherein the transduction does not require or does not comprise the use of viral vectors (in particular, does not comprise the use of viral vectors for expressing proteins inside cells), does not require or does not comprise the use of electroporation, does not require or does not comprise the use of carrier nanoparticles and/or does not require or does not comprise the use of liposomes.

In some embodiments, the invention provides a cell obtainable or obtained by the transduction methods of the present invention, for example, wherein the cell does not comprise a viral vector (for example, does not comprise the viral vectors encoding proteins that can modify genes), or for example, wherein the cell does not comprise carrier nanoparticles, micelles or liposomes. In some embodiments, the cell is a genetically modified cell.

In some embodiments, the molecule to be transduced into a cell is an endonuclease. Endonucleases are enzymes that cut DNA strands at a specific sequence. Transcription activator-like effectors (TALEs) are engineered transcriptional regulators that have been designed to bind a particular desired DNA sequence (Moscou, J & Bogdanove, A J *Science* 326 (5959): 1501, 2009). By combining such an engineered TALE with an endonuclease domain (which cuts DNA strands), one can engineer endonucleases that are specific for any desired DNA sequence. When these restriction enzymes are introduced into cells, they can be used for genome editing in situ, a technique known as genome editing with engineered nucleases. Transcription activator-like endonucleases (TALENs) can be used to edit genomes by inducing double-strand breaks (DSB), which cells respond to with repair mechanisms (Zhang, F et. al. *Nature Biotechnology* 29 (2): 149-53, 2011). Thus, in some embodiments, the invention provides the use of the transduction buffer in restriction enzyme-based or endonuclease-based (such as TALEN-based) genetic engineering. Accordingly, in some embodiments the molecule of interest to be transduced into a cell is a TALEN. Foreign nucleic acid sequences may also be introduced into the cell by methods of the present invention or by alternative transduction methods. DNA may optionally be introduced into a genome through non-homologous exon joining in the presence of exogenous double-stranded DNA fragments. Homology directed repair can also introduce foreign DNA at the double-stranded break as the transfected double-stranded sequences are used as templates for the repair enzymes. Thus, TALENs have been used to generate stably modified human embryonic stem cell and induced pluripotent stem cell (iPS cell) clones, to generate knockout *C. elegans*, knockout rats, and knockout zebrafish. Therefore, in some embodiments, genetic modification by TALENs or other transduced molecules, could be used to replace injection techniques currently used for the modification of pre-implantation embryos or blastocysts for the generation of genetically-modified animals (e.g. for the generation of model organisms displaying particular traits or with particular genetic diseases or disorders) (Voncken J W. Methods Mol Biol. 2011; 693:11-36). By coupling other domains onto the TALE backbone, one can also modify or regulate DNA in other ways. For example, the addition of a transactivation domain instead of the endonuclease domain, turns a TALE into a transcriptional activator. The addition of a repressor domain results in a TALE that shuts gene transcription off. Addition of a methylation domain allows DNA methylation at specific sites. Similarly, addition of a histone modification domain (for example histone acetylase) allows histone modification at specific sites etc. These are all envisaged as molecules for use with the invention.

In some embodiments, a protein nuclease and a guide nucleic acid (such as an sgRNA or gDNA) are transduced into the cell simultaneously or sequentially, using transduction compounds, buffers and/or methods of the invention. For example, in some embodiments, a Cas9 nuclease and an sgRNA are transduced into the cell simultaneously or sequentially. Small guide RNAs and guide DNAs can be designed to target a specific DNA sequence and thus this combination can be used for specific gene editing. As mentioned above, this combination is known as the CRISPR/Cas9 system. Other similar systems and alternatives to Cas9 nuclease, include proteins from the Cascade system, TtAgo and other Argonaute proteins, and other FOKI-nuclease associated proteins.

Thus in some embodiments, the invention provides a method, for transducing a gene editing system, such as a TALEN system, a CRISPR/Cas9 system (preferably including systems involving Cas analogs from different species), a FokI nuclease system, a Cascade system, a TtAgo system or other Argonaute protein systems, into a cell. The transduction compounds and buffers described herein can be used for such methods and can allow gene editing in cells, without the need for viral transfection (see comments above).

In some embodiments the nucleic acid targeted by the gene editing system is endogenous nucleic acid, e.g. genomic DNA. In other embodiments, nucleic acid targeted by the gene editing system is exogenous nucleic acid, which may, for example, be transduced into the cell with the gene editing system as part of the transduction method.

In some embodiments, such gene editing systems can be used to generate targeted gene mutations including but not limited to monoallelic or biallelic gene knockouts. When transduced into the cells using the methods of the invention, (for example, instead of using prior art viral transfection methods), the gene editing systems result in highly efficient monoallelic or biallelic gene knockouts. Thus, in some embodiments, the methods of the invention result in at least 1%, at least 2%, at least 5%, at least 10%, at least 20%, at least 30%, at least 40%, at least 50%, at least 60%, or at least 70% monoallelic or biallelic gene modification (or knockout).

Gene editing can also be used to study gene functions in animals and for gene therapy in animals, including humans. It is also useful in the field of synthetic biology for engineering cells and organisms to perform novel functions. In addition, gene functions can be studied modified cell lines, such as stem cell lines. Therefore, in some embodiments, the transduction compounds, methods or buffers of the invention, particularly when used in combination with the gene editing embodiments, can be used to study gene function, for gene therapy or for synthetic biology.

In some embodiments, in such methods, enzymes such as those described above are transduced into the embryonic or blastocyst cell to genetically modify the cell, prior to implantation into the animal. Thus in some embodiments, the transduction buffer and methods of the invention could be used to generate model organisms, such as knockout organisms. In other embodiments, it is contemplated that the transduction buffer and methods of the invention could be used for treating genetically inherited disorders in humans, e.g. at the human embryo or blastocyst stage (e.g. pre-implantation genetics). The invention thus provides a method for transducing a molecule of interest into a cell wherein the molecules of interest are nucleic acids and/or enzymes which modify nucleic acids, and optionally wherein the cell is an embryonic or blastocyst cell.

In some embodiments, the genetic modification involves the integration of foreign DNA into the host genome, wherein the foreign DNA is the molecule of interest that is transduced into a cell using the methods of the present invention. However, to avoid aberrant integration and genome disruption, in some embodiments the genetic modification involves a non-integrative approach, i.e. the modified nucleic acid is not integrated into the genome.

The transduction buffer and methods of the invention could also be used to generate iPS cells, either by genetically modifying cells to express certain transcription factors involved in pluripotent stem cell maintenance, or by transducing the transcription factors directly into the cells. Examples of transcription factors involved in the induction of pluripotency include but are not limited to OCT2/3/4, SOX2, KLF4, C-MYC, N-MYC, NANOG, ESRRB and LIN28.

In some embodiments, the invention provides a transduction buffer or pharmaceutical composition, for use in therapy, prophylaxis or diagnosis. In some embodiments the therapy is gene therapy, e.g. for treatment of genetic disorders, including inherited disorders. Genetic disorders that can be treated in accordance with the invention include, but are not limited to the following common disorders: 22q11.2 deletion syndrome, Angelman syndrome, Canavan disease, Charcot-Marie-Tooth disease, Color blindness, Cri du chat, Cystic fibrosis, Down syndrome, Duchenne muscular dystrophy, Haemochromatosis, Haemophilia, Klinefelter syndrome, Neurofibromatosis, Phenylketonuria, Polycystic kidney disease, Prader-Willi syndrome, Sickle-cell disease, Tay-Sachs disease, Turner syndrome. In some embodiments, the method can be used to modify genes that pathogens use to cause disease, and thus can be used to treat infection. Therefore in some embodiments, the therapy is for treatment of infectious diseases, for example including but not limited to HIV, malaria, African Trypanosomiasis, Cholera, Cryptosporidiosis, Dengue, Hepatitis A/B/C, Influenza, Japanese Encephalitis, Leishmaniasis, Measles, Meningitis, Onchocerciasis ("river blindness"), Pneumonia, Rotavirus, Schistosomiasis, Shigellosis, Strep Throat, Tuberculosis, Typhoid, Typhoid.

The invention also provides methods for therapy or diagnosis comprising transducing a molecule of interest into a cell. The cell may be an in vivo cell, in which case the treatment is a direct treatment. Alternatively, the cell may be transduced in vitro, e.g. for in vitro diagnosis. Alternatively, the cell may be transduced in vitro prior to transplantation of the cell into a patient. The transplantation may be autologous or allogenic, i.e. the transduced cell may be transplanted back into the same patient that it was taken from (autologous) or into a different person (allogenic). In a preferred embodiment the transplantation is autologous.

Biological drugs (also known as biologics) including monoclonal antibodies, cytokines, tissue growth factors and therapeutic proteins are becoming increasingly important alternatives to chemical small molecules for use in therapy. However, there are a number of difficulties associated with biological drugs, in particular relating to their delivery to the target of interest. The transduction buffers and methods of the present invention could be used to improve delivery of biologics to cells. For example, in some embodiments the molecule of interest in the methods of the invention is a biologic, for example selected from a monoclonal antibody, cytokine, tissue growth factor and therapeutic protein. The cell of interest may be transduced in vitro and transplanted back into the patient, or the cell may be transduced in vivo.

In some embodiments there is provided a protein that modifies a nucleic acid, for example a gene editing system (such as ZNF, TALEN, CRISPR/Cas9, the Cascade system, TtAgo and other Argonaute systems, and other FOKI-nuclease associated proteins), for use in therapy. In some embodiments, said therapy comprises a method of transducing a molecule into a cell according to the invention. A number of diseases and conditions can be treated by transduction of proteins that modify a nucleic acid, for example gene editing systems, and it would be clear to the skilled person which diseases or conditions can be treated. Conditions and diseases treatable by transduction of a protein that modifies a nucleic acid, for example a gene editing system, include but are not limited to genetic diseases such as, sickle cell disease, Leber's congenital amaurosis, X-linked SCID, ADA-SCID, adrenoleukodystrophy, chronic lymphocytic leukemia (CLL), acute lymphocytic leukemia (ALL), multiple myeloma, haemophilia and Parkinson's disease. The therapy may be somatic or germline gene therapy, i.e. in some embodiments the cell in the transduction method is a somatic cell or a germ cell.

The transduction buffer and methods of the invention can also be used to load antigens into antigen-presenting cells for presentation to the immune system. This advantageously produces a novel vaccine manufacturing process. For example, antigens have been loaded into dendritic cells in vitro and then transplanted back into the body. However, the methods used up until now have damaged the dendritic cells, e.g. because they have forced the proteins into the cells using mechanisms such as endocytosis. Dendritic cells already have very active macropinocytosis pathways. Therefore, by using methods of the invention, the dendritic cells could be loaded with antigen via the macropinocytosis pathway, with negligible damage to the cell. This method could either be carried out in vitro prior to transplantation of the cells into the patient or the antigens could be transduced into dendritic cells (or other antigen presenting cells) in vivo, e.g. by sub-cutaneous injection.

Accordingly, there is provided the use of the transduction buffer for transducing antigens into antigen presenting cells. There is also provided a method for transducing antigens into antigen presenting cells. The invention also provides the use of the transduction buffer and/or methods of the invention for manufacturing a vaccine, for example, whereby the vaccine comprises antigen-presenting cells that have been transduced by the methods of the present invention, i.e. wherein the antigen of interest has been transduced into the cell. Similarly, the invention provides a method of vaccinating, treating or preventing a subject comprising administering a cell to the subject, wherein the cell has been transduced by a method of the present invention. Likewise the invention provides a cell for use in a method of vaccinating, treating or preventing a subject, wherein the method comprises comprising administering a cell to the subject, wherein the cell has been transduced by a method of the present invention.

In some embodiments, the invention provides the use of a transduction buffer described herein in a method for cationic lipid-mediated DNA transfection. The invention provides a method for transducing lipid and DNA into cell, wherein the method is as described herein.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%. It also refers specifically to the exact value, e.g in the above example, to exactly 10%. Where necessary, the word "about" may be omitted from the definition of the invention.

The term "a" or "an", unless specifically stated otherwise, means "one or more". For example, it can mean "only one" or it can mean "more than one", for example "two, three, four, five or more".

Unless specifically stated, a process comprising a step of mixing two or more components does not require any specific order of mixing. Thus components can be mixed in any order. Where there are three components then two components can be combined with each other, and then the combination may be combined with the third component, etc.

It will be understood that the invention will be described by way of example only and modifications may be made whilst remaining within the scope and spirit of the invention.

BRIEF DESCRIPTION OF DRAWINGS

(FIG. 1B) FACS analysis of hESCs transduced with CRE protein at different times with different iTOP transduction media with different osmolalities where iTOP-1250, iTOP-2500 and iTOP-3250 have a final calculated Osmolalities of 1250, 2500 and 3250 mOsmol/Kg, respectively. Control is cells incubated with iTOP transduction media without CRE protein. Total percentage GFP expressing cells is shown in the histogram plots. As shown, iTOP-2500 and iTOP-3250 conditions accelerate protein transduction and allow a more uniform transduction of the cell population.

FIGS. 2A-2D: iTOP-CRE transduction in vivo (FIG. 2A) Schematic representation of the CRE reporter mice. A single copy of a loxP-mRFP-loxP-mGFP reporter was inserted in the Rosa26 locus. Excision of the Stop cassette by Cre-recombinase protein induces GFP expression. Transduced CRE protein excises the loxP-flanked RFP-STOP cassette and switches fluorescence from red (RFP) to green (GFP).

(FIG. 2B) In vivo transduction of skeletal muscle of a loxP-mRFP-loxP-mGFP reporter mouse with recombinant CRE protein using the iTOP-1250 buffer. Fluorescence images of the CRE-transduced whole muscle. Control is cells incubated with iTOP-1250 transduction media without CRE protein.

(FIG. 2C) Microscopy fluorescence images of cross-sections of the muscles transduced in (B). Control is cells incubated with iTOP-1250 transduction media without CRE protein.

(FIG. 2D) Fluorescence image of whole muscle injected with recombinant CRE protein in iTOP-3250 buffer demonstrating efficient in vivo CRE transduction in high osmolarity transduction buffer.

10 microliter recombinant Cas9 protein in 5× Transduction buffer (25 mM $NaH_2PO_4$, pH8.0, 500 mM NaCl, 250 mM NDSB-201, 150 mM Glycerol, 75 mM Glycine, 1.25 mM $MgCl_2$, 1 mM Beta-mercapto-ethanol and 200 microM Cas9 protein) was mixed with 30 microliter dilution buffer: 375 mM NaCl and 250 mM GABA in OptiMEM and 10 microliter test compound solution as listed below. Test compounds were either amino acids, sugars, salts or combinations thereof as indicated.

List of used test buffers (numbers correspond with the images in the figure): 1: $H_2O$ (control); 2: 250 mM L-Arg in $H_2O$; 3: 200 mM L-Glu in $H_2O$; 4: 250 mM L-Arg+200 mM L-Glu in $H_2O$; 5: 10% Sucrose in $H_2O$; 6: 25% Sucrose in $H_2O$; 7: 10% Sorbitol in $H_2O$; 8: 25% Sorbitol in $H_2O$; 9: 375 mM RbCl in $H_2O$; 10: 1M RbCl in $H_2O$; 11: 3.5M RbCl in $H_2O$; 12: 25% Sucrose+1M RbCl in $H_2O$.

Figure 4A:
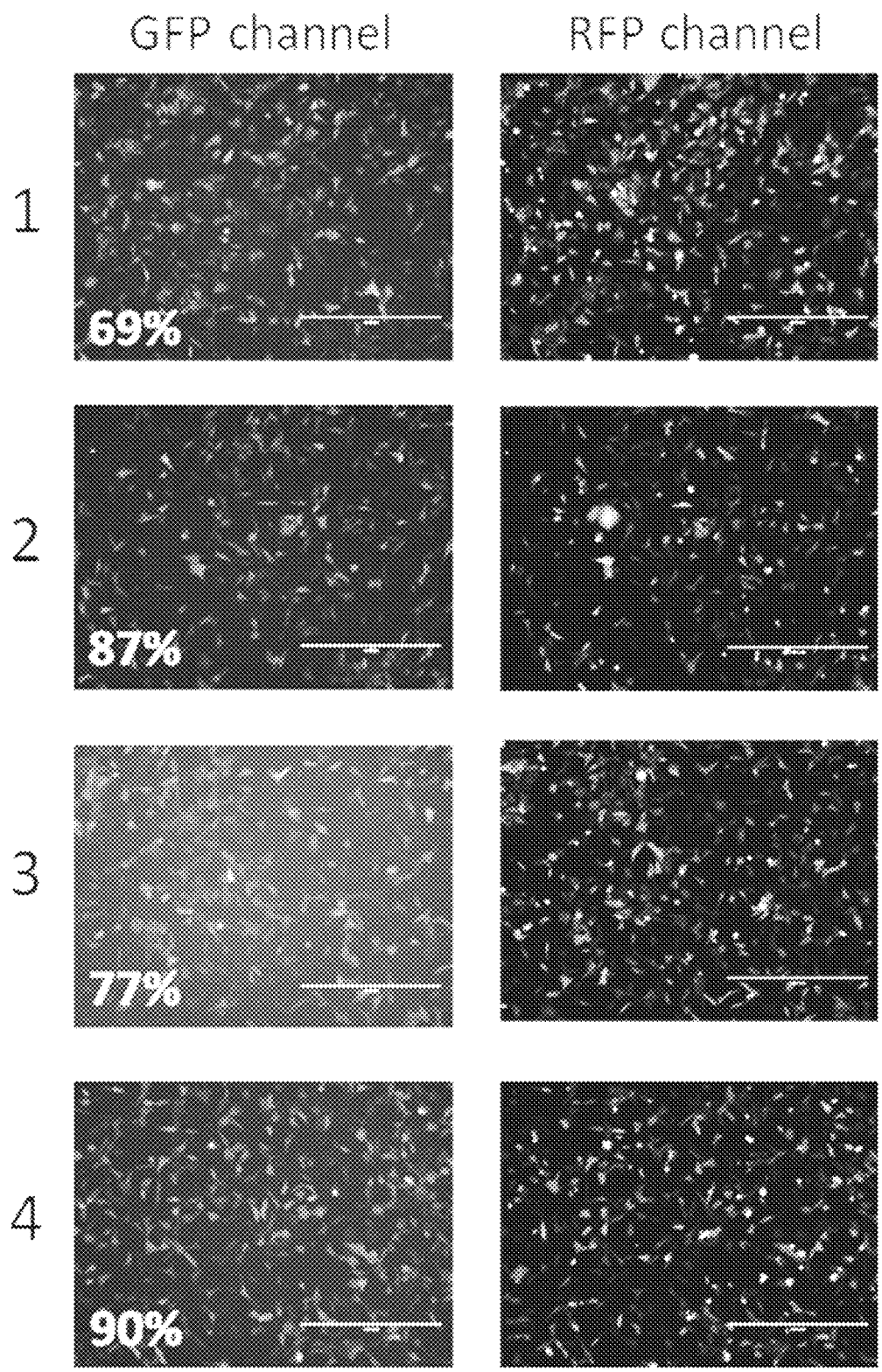
Figure 4B:
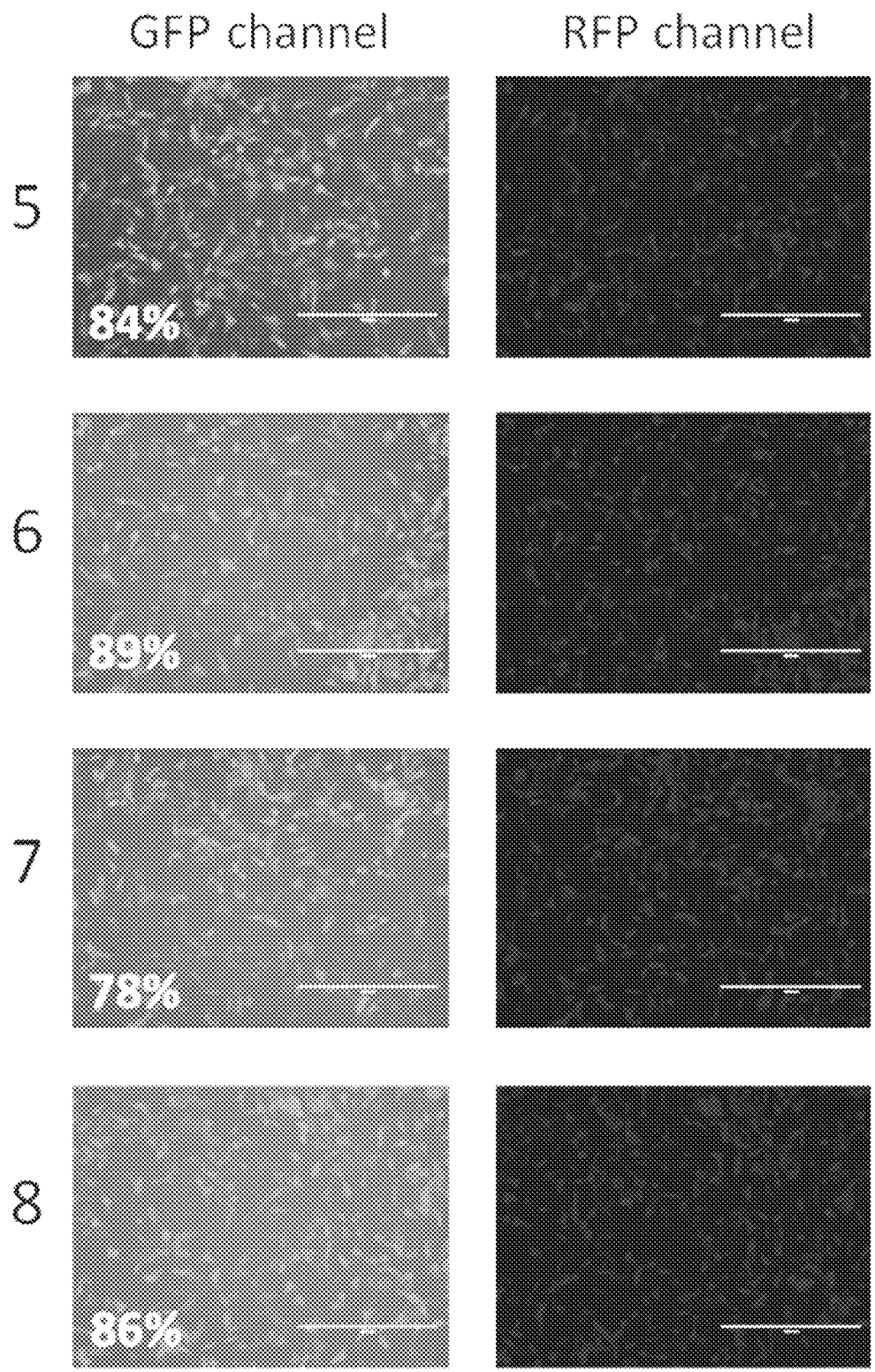
Figure 4C:
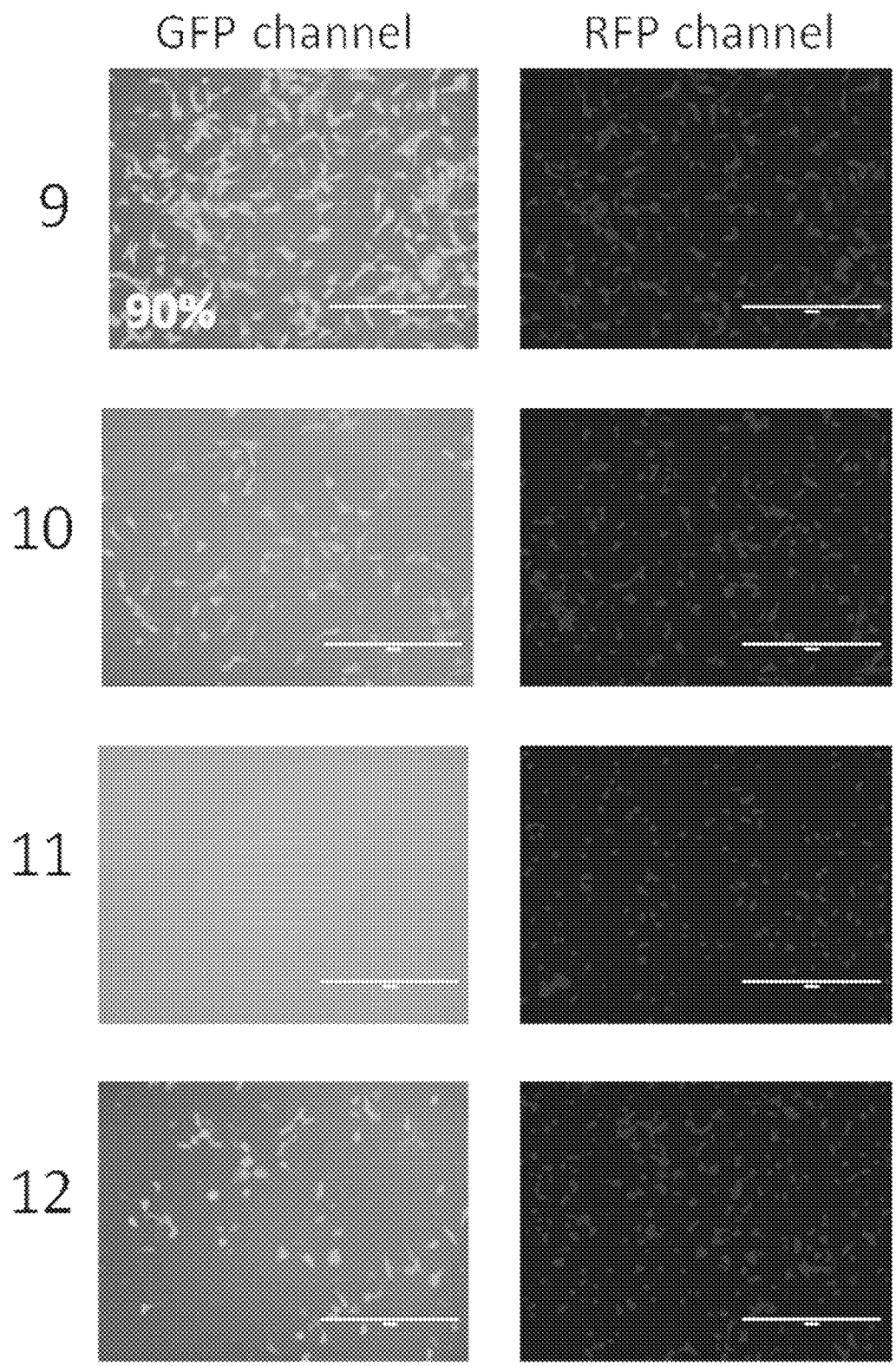

FIGS. 4A-4C: Effect of test compounds on iTOP protein transduction

Figure 1A:
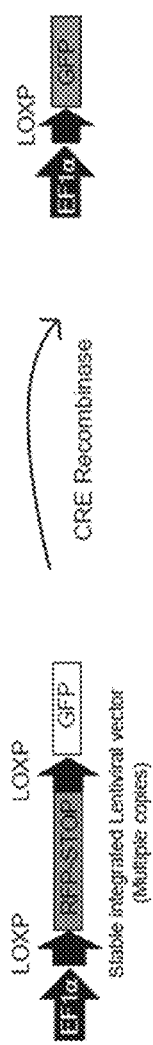
FIGS. 1A-1B: Development of Fast iTOP transduction media (FIG. 1A) Schematic representation of the CRE recombinase reporter. A lentiviral EF1a-loxP-RFP-stop-loxP-GFP/ires-PuroR construct was stably introduced into human Embryonic Stem cells (hESCs). Transduced CRE protein excises the loxP-flanked RFP-STOP cassette and switches fluorescence from red (RFP) to green (GFP).

KBM7 cells containing a CRE reporter construct (as shown in FIG. 1A) were transduced via iTOP by mixing 10 microliter 5× Transduction buffer (25 mM $NaH_2PO_4$, pH8.0, 500 mM NaCl, 250 mM NDSB-201, 150 mM Glycerol, 75 mM Glycine, 1.25 mM $MgCl_2$, 1 mM Beta-mercapto-ethanol and 10 microgram/microliter CRE recombinase protein) with 30 microliter iTOP enhancer buffer (Opti-MEM media (Life Technologies) supplemented with 542 mM NaCl, 333 mM GABA, ITS supplement (life technologies), 1.673 non-essential amino acids, 3.3 mM Glutamine, 167 ng/ml bFGF2, and 84 ng/ml EGF) and 10 microliter of one of the test compound solutions as listed below:

List of used test compound solutions (numbers correspond with the images in the figure): 1: $H_2O$ (control); 2: 250 mM L-Arg in $H_2O$; 3: 200 mM L-Glu in $H_2O$; 4: 250 mM L-Arg+200 mM L-Glu in $H_2O$; 5: 10% Sucrose in $H_2O$; 6: 25% Sucrose in $H_2O$; 7: 10% Sorbitol in $H_2O$; 8: 25% Sorbitol in $H_2O$; 9: 375 mM RbCl in $H_2O$; 10: 1M RbCl in $H_2O$; 11: 3.5M RbCl in $H_2O$; 12: 25% Sucrose+1M RbCl in $H_2O$.

Cells were transduced for 30 minutes, after which media was replaced. RFP and GFP fluorescence were measured by fluorescence microscopy and FACS analysis 24 hours after transduction. While high concentrations of RbCl (samples 10, 11 and 12) are toxic at the 30 minute transduction time and hence yielded few cells after transduction, all tested compounds support robust iTOP transduction. Furthermore, all compounds, alone or in combination, enhanced the efficiency of iTOP transduction as indicated by the percentage of GFP-positive cells in the left panels.

Figure 5:
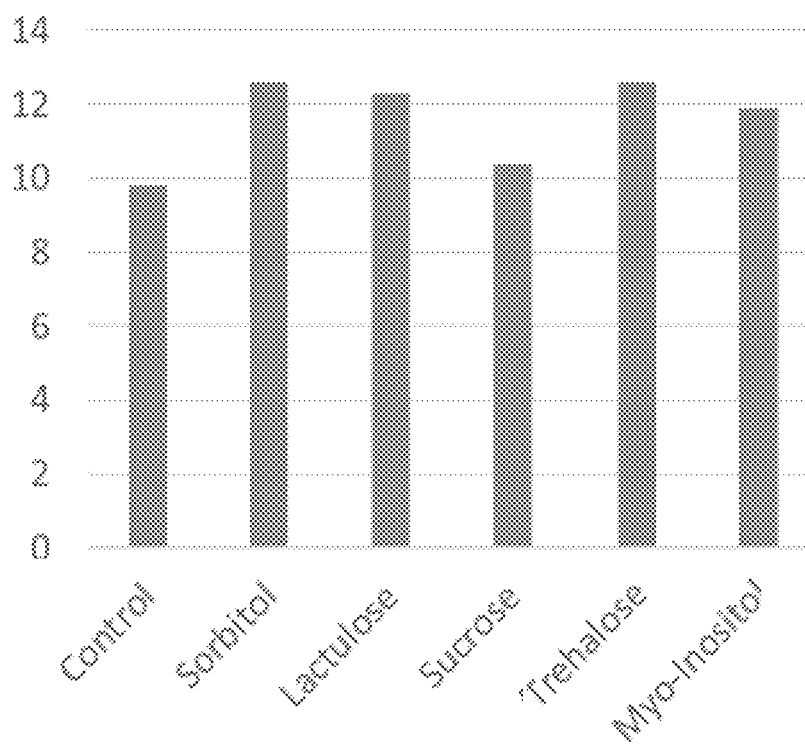
Figure 6D:
Figure 6D:
Figure 6D:
Figure 6D:
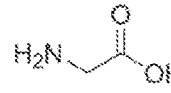
Figure 6D:
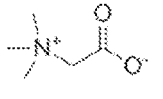
Figure 6D:
Figure 6D:
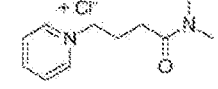

FIG. 5: Effect of carbohydrate supplements on transduction efficiency

KBM7 cells carrying an out-of-frame tdTomato reporter were transduced for 40 minutes with recombinant Cas9 protein and sgRNA targeting the out-of-frame region in the tdTomato reporter. Transductions were carried out in 1× iTOP transduction buffer, supplemented with 327 mM NaCl and 200 mM GABA. Indicated carbohydrates were added at 0.8% w/v final concentration. Two days after transduction, tdTomato fluorescence was determined by flow cytometry analysis. The γ-axis shows level of tdTomato fluorescence and is indicative of transduction efficiency.

FIGS. 6A-6D:

List of transduction compounds their protein transduction activity and effect on cell proliferation in transduction buffer. First column: transduction compound number; Second column: chemical structure of the transduction compound. Third column: Relative β-lactamase protein transduction activity; Fourth column: Relative BrdU incorporation 24 hrs after β-lactamase transduction. MEFs were transduced for 3 hours with 1 µM β-lactamase protein at a NaCl adjusted osmolality of 700 mOsm/Kg in transduction buffer containing 30 mM of Glycerol and 15 mM of Glycine and 25 mM of the indicated transduction compounds. β-lactamase incorporation of the reference compound (NDSB201, #01) was set at 100%. Open circles indicate relative BrdU incorporation by the transduced cells. BrdU incorporation of untransduced cells was set at 100% and BrdU incorporation of mitomycin C-treated cells was set at 0%.

Example 1

The ability to introduce small- or macromolecules into cells finds important applications in research and medicine. Unfortunately, the cell membrane presents a major obstacle for the introduction of many biologically active molecules. We recently demonstrated how a combination of salt-induced hypertonicity, a propanebetaine compound and osmoprotectants induces the uptake and intracellular release of native proteins into primary (stem) cells. We named this transduction process 'iTOP', for induced transduction by osmocytosis and propanebetaine. An unexpected observation was that the nature of the hypertonic signal was critical for iTOP transduction to occur. Sodium-related salts were shown to be efficient inducers of iTOP transduction, but other compounds that create a hypertonic environment, such as sucrose or sorbitol, had no protein transducing effect. In addition, we observed that the speed and efficiency of the iTOP transduction process depends on the extracellularly applied salt concentration, with higher osmolarities resulting in faster and more efficient uptake. We demonstrated that iTOP mediated intracellular delivery of recombinant Cas9 protein and an in-vitro transcribed guideRNA allows efficient gene editing, demonstrating that the iTOP-CRISPR/Cas9 transduction platform can be an effective tool for the repair of genetic defects. At the applied osmolarity of 1250 mOsm/Kg, the iTOP transduction process takes approximately 45-120 minutes, depending on cell type. This incubation time can sometimes be too long, for example in situations where prolonged in vitro maintenance of primary cells is not possible, due to the length of a medical procedure, problems with ex vivo cell survival or situations of in vivo iTOP transduction, where it difficult to maintain local concentrations of the iTOP components for sufficiently long time. Here we describe how a modified version of our iTOP transduction buffer vastly enhances both the speed of the transduction process and demonstrate how this buffer allows effective and uniform transduction of primary (stem) cells, both in vitro and in vivo.

As mentioned, the speed and efficiency of the iTOP transduction process depends on the extracellularly applied salt concentration, with higher osmolarities resulting in faster and more efficient uptake. At 1250 mOsm/Kg, efficient protein transduction takes between 45 and 200 minutes. Further elevation of salt-induced hypertonicity can in theory enhance the transduction rate, but the maximum transduction rate is of course limited by the tolerance of the cells or tissues to the hypertonicity. In addition, protein folding, activity and solubility are very much dependent on salt concentration. Too low or too high salt concentrations can have a detrimental effect on protein stability or solubility. Thus, it is critically important to optimize the transduction conditions to both the properties of the target cell type or tissue as well as to the properties of the transducted protein.

Osmolarity can also be raised by other compounds, including for example sorbitol or sucrose, but we had observed that these compounds cannot replace sodium, or sodium-related salts in inducing protein transduction. We have now observed however, that combining different sodium related salts, or combining different sodium related salts and other hypertonicity-inducing compounds, such as for example sucrose, to raise osmolality further without generating too high a salt concentration, accelerates protein transduction, significantly shortening the time needed for uniform transduction of a cell population, both in vitro and in vivo. Below we describe the composition of the modified transduction buffers, compared to the previously reported iTOP-1250 buffer.

Materials and Methods

|  | iTOP-1250 buffer composition: | iTOP-2500 buffer composition: | iTOP-3250 buffer composition: |
|---|---|---|---|
| Transduction compounds Osmoprotectants | 200 mM GABA 50 mM NDSB-201 15 mM Glycine 30 mM Glycerol | 200 mM GABA 50 mM NDSB-201 15 mM Glycine 30 mM Glycerol | 200 mM GABA 50 mM NDSB-201 15 mM Glycine 30 mM Glycerol |
| Sodium-related salt(s) | 425 mM NaCl* | 862 mM NaCl* 125 mM RbCl | 1125 mM NaCl* 200 mM RbCl |
| Further osmolality-inducing component | — | 63 mM Sucrose | 100 mM Sucrose |
| Other components | 0.75x Glutamine 0.75x Non-Essential amino Acids 0.75x N2 0.75x B27 100 ng/ul FGF2 100 ng/ul EGF 10 uM of protein of interest (e.g CRE recombinase) Optimem (Final Osmolality: 1250 mOsmol/Kg) | 0.75x Glutamine 0.75x Non-Essential amino Acids 0.75x N2 0.75x B27 100 ng/ul FGF2 100 ng/ul EGF 10 uM of protein of interest (e.g CRE recombinase) Optimem (Final Osmolality: 2500 mOsmol/Kg) | 0.75x Glutamine 0.75x Non-Essential amino Acids 0.75x N2 0.75x B27 100 ng/ul FGF2 100 ng/ul EGF 10 uM of protein of interest (e.g CRE recombinase) Optimem (Final Osmolality: 3250 mOsmol/Kg) |

*The NaCl listed in the buffers is added in addition to NaCl present in the Optimem media.

Results

Figure 1B:
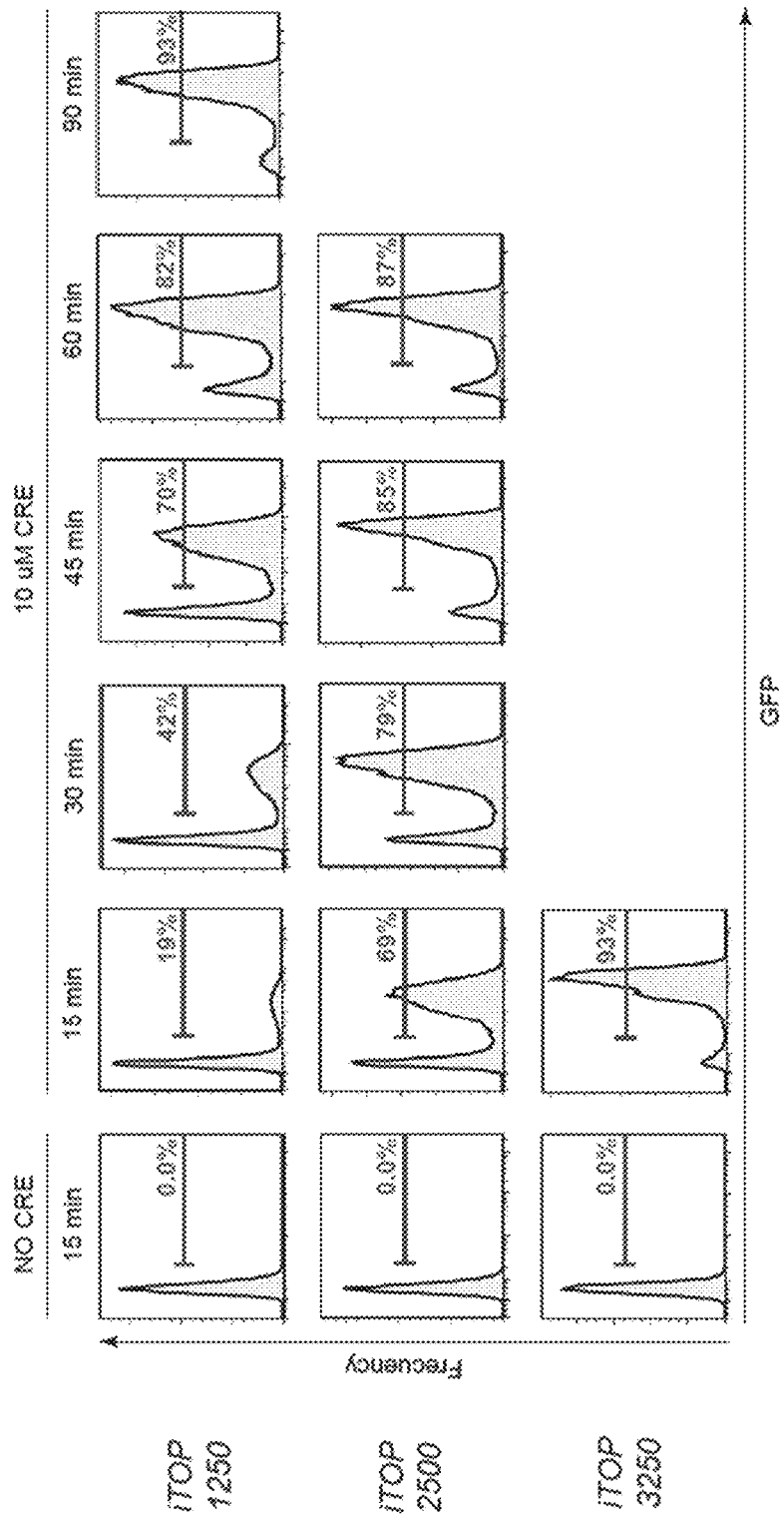

FIG. 1B shows the percentage of GFP-expressing cells, i.e. the percentage of cells which have been transduced with CRE recombinase, over time, at each of the three transduction buffer compositions shown above.

It was seen that using iTOP 1250, which contains only a single sodium salt, no further osmolality inducing compound, and which has a final osmolality of 1250 mOsmol/kg, it took approximately 60 minutes to achieve 80% transduction and at 15 minutes only 19% of cells had been transduced.

Using iTOP 2500, which contains two sodium-related salts (NaCl and RbCl), which additionally contains a further osmolality inducing compound (sucrose) and which has a final osmolality of 2500 mOsmol/kg, it took only approximately 30 mins to achieve 80% transduction, and at 15 minutes nearly 70% of cells had already been transduced.

Using iTOP 3250, which contains two sodium-related salts (NaCl and RbCl), which additionally contains a further osmolality inducing compound (sucrose) and which has a final osmolality of 3250 mOsmol/kg, it took only 15 mins to achieve 93% transduction.

Thus it was concluded that increasing the osmolality to more than 1250 mOsmol/kg, by using more than one sodium-related salt and/or by including further non-salt osmolality inducing component in the transduction buffer, the efficiency of transduction can be dramatically improved.

FIGS. 2A-2D show that iTOP3250 transduction buffer also demonstrates efficient CRE transduction in vivo.

Example 2

KBM7 cells are contacted with the iTOP-3250 transduction buffer described in example 1 and with Cas9 and a sgRNA, containing a 20 nt guide sequence conferring its target specificity and an 80 nt scaffold sequence.

Example 3

We previously observed that transduction efficiency is directly related to the concentration of the extracellularly applied protein. However, Cas9 is an example of a protein that is relatively insoluble in a hydrophilic buffer, such as the iTOP buffer. The amount of (for example) Cas9 protein that can be transduced into cells is therefore limited by the maximum concentration of the protein in the buffer. Here we describe new variations on the iTOP buffer that permit higher concentrations of protein thereby enhancing the amount of protein that can be delivered intracellularly. In addition, some of these compounds also shorten transduction time, by raising buffer osmolarity.

As mentioned, the speed and efficiency of the iTOP transduction process depends on the concentration of the extracellularly applied protein, with higher protein concentrations resulting in more efficient protein uptake and higher intracellular concentrations. We demonstrated that at 75 microMolar Cas9 protein is effectively transduced into primary (stem) cells, allowing efficient gene editing, but higher protein concentrations can in theory further enhance the gene editing efficiency. The maximum amount of protein that can be transduced is of course limited by the solubility of the cargo protein in the watery iTOP buffer. In addition, protein folding and activity and the tolerance of the target cells to the iTOP buffer are very much dependent on buffer composition. Thus, it is critically important to optimize the transduction conditions to both the properties of the target cell type or tissue as well as to the properties of the transducted protein, to allow maximization of protein concentration, as well as minimizing the effect of the transduction buffer on target cell survival, proliferation, identity and function.

Here we describe a method for the identification of iTOP-compatible solubility enhancers. In addition, we list a series of compounds which can enhance protein solubility and are compatible with, or even enhance the iTOP transduction process.

Figure 3:
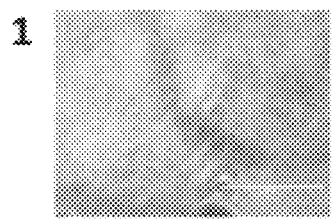
FIG. 3: Cas9 protein solubility assay The ability of test compounds to prevent protein precipitation was assessed by semiquantitative turbidimetric assay. The combination of L-Arg and L-Glu or addition of RbCl was surprisingly found to prevent Cas9 precipitation.
Figure 3:
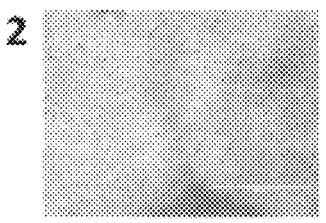
Figure 3:
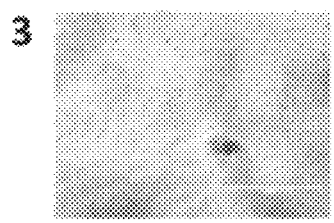
Figure 3:
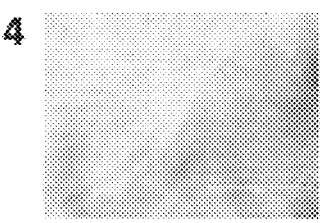
Figure 3:
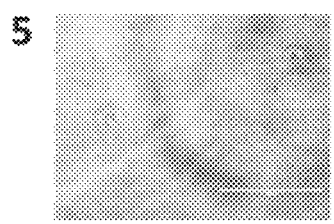
Figure 3:
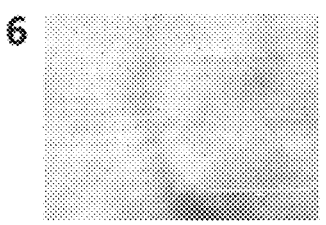
Figure 3:
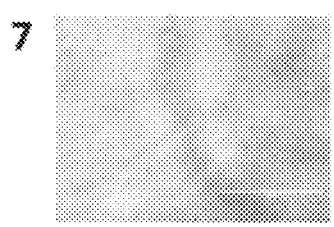
Figure 3:
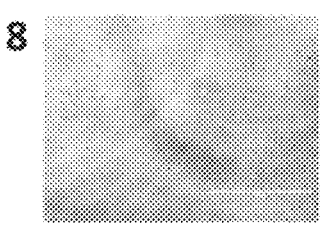
Figure 3:
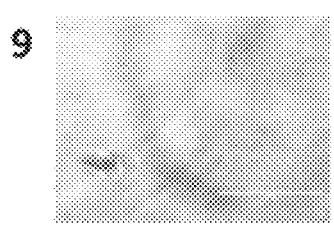
Figure 3:
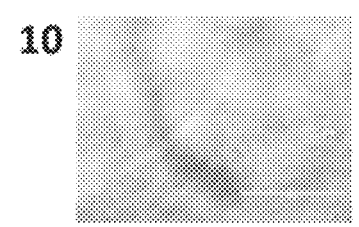
Figure 3:
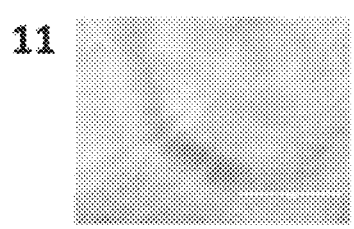
Figure 3:
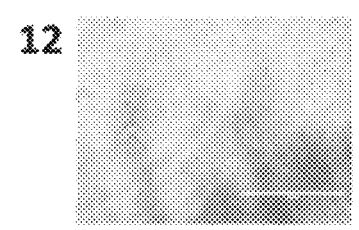

FIG. 3 shows that the addition of the combination of L-Arg and L-Glu or the addition of RbCl was surprisingly found to prevent Cas9 precipitation. In contrast, the addition of one of L-Arg, L-Glu, sucrose and sorbitol did not significantly enhance Cas9 solubilization.

Example 4

The effect of various carbohydrates on transduction efficiency was tested in the iTOP buffer. KBM7 cells carrying an out-of-frame tdTomato reporter were transduced for 40 minutes with recombinant Cas9 protein and sgRNA targeting the out-of-frame region in the tdTomato reporter. Transductions were carried out in 1× iTOP transduction buffer, supplemented with 327 mM NaCl and 200 mM GABA. Indicated carbohydrates (sorbitol, lactulose, sucrose, trehalose and myo-inositol) were added at 0.8% w/v final concentration. Two days after transduction, tdTomato fluorescence was determined by flow cytometry analysis. Higher levels of tdTomato fluorescence were indicative of greater transduction efficiency. As shown in FIG. 5, all carbohydrates tested increased transduction efficiency, with the greatest improvement seen for trehalose and sorbitol, closely followed by lactulose and myo-inositol.

Sucrose was also seen to improve transduction efficiency.

The invention claimed is:

1. A method for transducing a molecule of interest into a cell, wherein the method comprises contacting said cell with the molecule of interest and a transduction buffer, wherein the transduction buffer comprises:
   (i) a transduction compound;
   (ii) a salt selected from a sodium, rubidium, lithium, potassium, caesium salt, and any combination thereof; and
   (iii) a non-salt osmolality-inducing component selected from sucrose, lactose, maltose, trehalose, cellobiose, lactulose, glucose, fructose, galactose, ribose, sorbitol, mannitol, xylitol and erythritol, wherein the transduction buffer osmolality is between about 1250 mOsmol/kg and about 4000 mOsmol/kg, wherein the transduction compound is selected from the group consisting of:

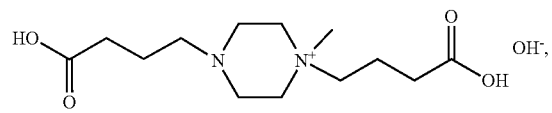

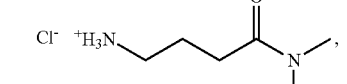

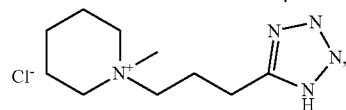

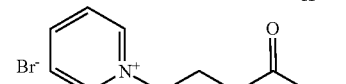

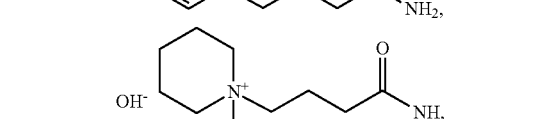

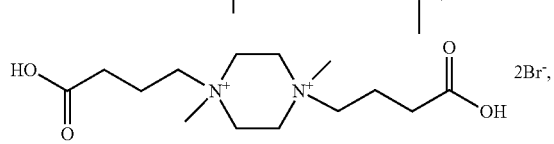

-continued

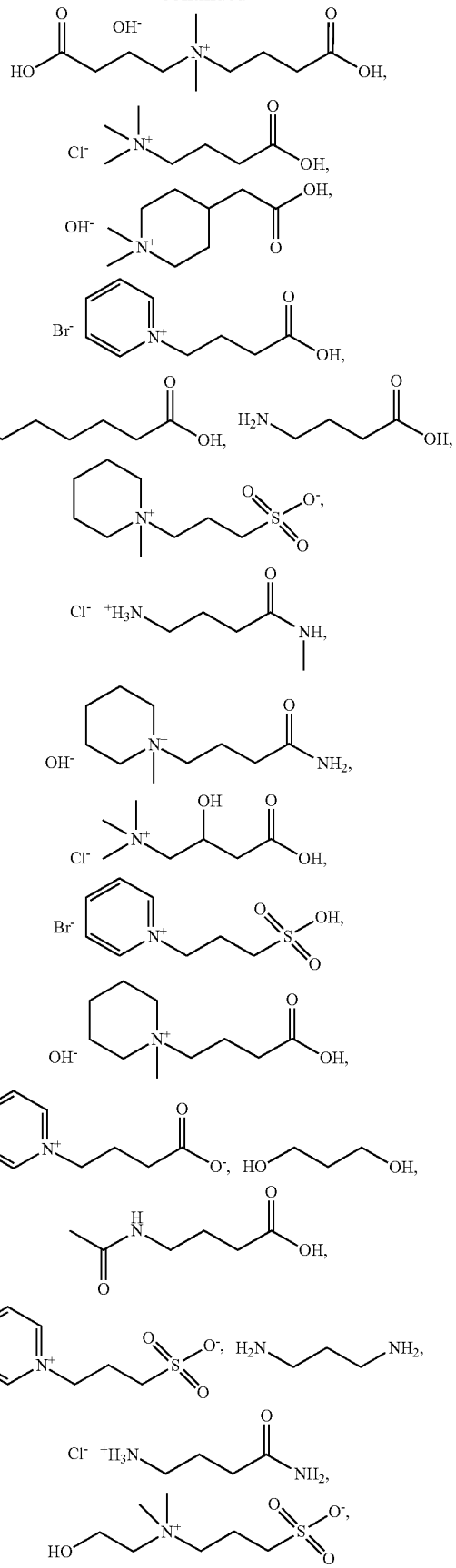

-continued

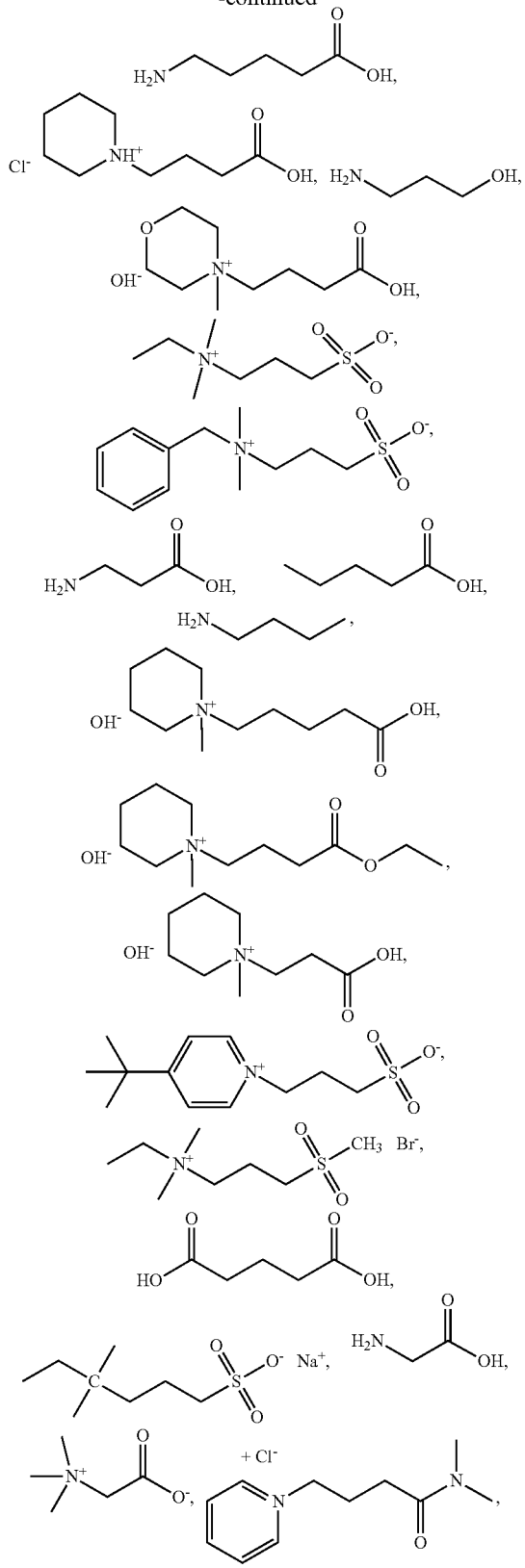

and any combination thereof.

2. The method of claim 1, wherein the non-salt osmolality-inducing component is sucrose.

3. The method of claim 1, wherein the non-salt osmolality-inducing component is sucrose at a concentration of between about 50 mM and about 150 mM.

4. The method of claim 1, wherein the transduction compound comprises NDSB-201 and GABA.

5. The method of claim 1, wherein the transduction buffer comprises
   (i) 200 mM GABA and 50 mM NDSB-201 as transduction compounds,
   (ii) sodium chloride and rubidium chloride as salts at a total concentration of between 500 mM and 1500 mM,
   (iii) sucrose as the non-salt osmolality inducing component and the final osmolality of the transduction buffer is between about 2500 mOsmol/kg and about 4000 mOsmol/kg, and
   (iv) 15 mM glycine and 30 mM glycerol as osmoprotectants.

6. The method of claim 1, wherein the molecule of interest is a protein capable of modifying a nucleic acid, and the method further comprises modifying a nucleic acid in the cell.

7. The method of claim 6, wherein the protein capable of modifying a nucleic acid is targeted to a specific target sequence through a guide sequence.

8. The method of claim 7, wherein the protein capable of modifying a nucleic acid is a zinc finger nuclease, a TALEN, Cas9, a Cas9 analog, a DNA-targeted FokI-nuclease associated protein, a Cascade complex, a TtAgo protein or other Argonaute protein.

9. The method of claim 7, wherein the protein capable of modifying a nucleic acid is targeted to a specific target sequence independent of a guide sequence.

10. The method of claim 6, wherein the protein capable of modifying a nucleic acid is a zinc finger nuclease, a TALEN, Cas9, a Cas9 analog, a DNA-targeted FokI-nuclease associated protein, a Cascade complex, a TtAgo protein or other Argonaute protein.

11. The method of claim 1, wherein the non-salt osmolality-inducing component is at a concentration of between about 10 mM and about 500 mM.

12. The method of claim 1, wherein the salt is sodium chloride.

13. The method of claim 1, wherein the transduction buffer further comprises one or more protein solubilizing agent, wherein the protein solubilizing agent is a rubidium salt and/or one or more amino acid.

14. The method of claim 1, wherein the osmolality of the transduction buffer is between about 1500 mOsmol/kg and about 4000 mOsmol/kg.

15. The method of claim 1, wherein the transduction buffer further comprises an osmoprotectant.

16. The method of claim 1, wherein the one or more salt is present at a total concentration of between about 250 mM and about 2500 mM.

* * * * *

UNITED STATES PATENT AND TRADEMARK OFFICE
CERTIFICATE OF CORRECTION

PATENT NO. : 12,209,252 B2  
APPLICATION NO. : 15/775791  
DATED : January 28, 2025  
INVENTOR(S) : Niels Geijsen et al.

Page 1 of 1

It is certified that error appears in the above-identified patent and that said Letters Patent is hereby corrected as shown below:

In the Claims

In Claim 1, Column 57, Line 50, delete:

""

And replace with:

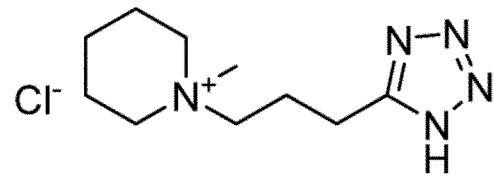

In Claim 1, Column 59, Line 45, delete:

""

And replace with:

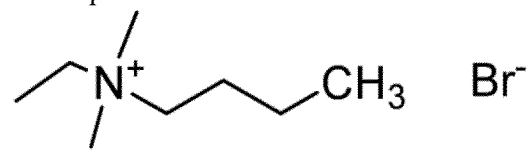

Signed and Sealed this  
Twentieth Day of May, 2025

Coke Morgan Stewart  
*Acting Director of the United States Patent and Trademark Office*